United States Patent
Lee et al.

(10) Patent No.: US 8,742,075 B2
(45) Date of Patent: *Jun. 3, 2014

(54) MONOCLONAL ANTIBODIES AGAINST ANGPTL3

(75) Inventors: E-Chiang Lee, The Woodlands, TX (US); Gregory Landes, San Bruno, CA (US); Seokjoo Hong, Kilgore, TX (US); Urvi Desai, The Woodlands, TX (US); David Powell, Houston, TX (US); Xiao Feng, The Woodlands, TX (US)

(73) Assignee: Lexicon Pharmaceuticals, Inc., The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/073,617

(22) Filed: Mar. 28, 2011

(65) Prior Publication Data

US 2011/0243948 A1 Oct. 6, 2011

Related U.S. Application Data

(63) Continuation of application No. 12/001,012, filed on Dec. 6, 2007, now Pat. No. 7,935,796.

(60) Provisional application No. 60/873,834, filed on Dec. 8, 2006.

(51) Int. Cl.
*C07K 16/26* (2006.01)
*C07K 16/00* (2006.01)
*A61K 39/395* (2006.01)

(52) U.S. Cl.
USPC ............... 530/388.24; 530/388.1; 530/387.9; 424/145.1; 424/141.1; 424/130.1

(58) Field of Classification Search
CPC . A61K 38/00; A61K 2039/505; C07K 16/18; C07K 16/22; C07K 16/26
See application file for complete search history.

(56) References Cited

U.S. PATENT DOCUMENTS

| | | | |
|---|---|---|---|
| 6,074,873 A | 6/2000 | Fong et al. | |
| 7,935,796 B2 * | 5/2011 | Lee et al. ............... | 530/388.24 |
| 2003/0100051 A1 | 5/2003 | Ruben et al. | |
| 2003/0215451 A1 | 11/2003 | Ferrara et al. | |

FOREIGN PATENT DOCUMENTS

| | | |
|---|---|---|
| EP | 1239050 A1 | 9/2002 |
| EP | 1403367 A1 | 3/2004 |
| MX | PA/a/2004/004609 | 9/2004 |
| WO | 9967382 A2 | 12/1999 |
| WO | 02101039 A1 | 12/2002 |
| WO | 03/044172 A2 | 5/2003 |

OTHER PUBLICATIONS

Supplementary European Search Report mailed Dec. 8, 2011, in European Patent Application No. 07862629.8.

NCBI Reference Sequence XP_001159650; Predicted: anglopoietin-like 3 isoform 2 [Pan troglodytes]; http://www.ncbi.nlm.nihgov/protein/xp_001159650, 2006.
Eurasia Research Report; 200970556; issued Feb. 3, 2010.
Ando et al., "A deceased expression of angiopoietin-like 3 is protective against atherosclerosis in apoE-deficient mice," J. Libid Res., 44: 1216-1223 (2003).
Conklin et al., "Identification of a mammalian angiopoietin-related protein expressed specifically in liver," Genomics, 62: 477-482 (1999).
Fugier et al., "The lipoprotein lipase inhibitor ANGPTL3 is negatively regulated by thyroid hormone," J. Biol. Chem., 281: 11553-11559 (2006).
Fujimoto et al., "Angptl3-null mice show low plasma lipid concentrations by enhanced lipoprotein lipase activity." Exp. Anim., 55: 27-34 (2006).
Ge et al., "Differential regulation and properties of angiopoietin-like proteins 3 and 4," J. Lipid Res., 46:1484-1490 (2005).
Hatsuda et al., "Association between plasma angiopoietin-like protein 3 and arterial wall thickness in healthy subjects," J. Vasc. Res., 44: 61-66 (2007).
Kathiresan et al., "Six new loci associated with blood low-density lipoprotein cholesterol, high-density lipoprotein cholesterol or triglycerides in humans," Nat. Genet., 40:189-197 (2008).
Kersten, "Regulation of lipid metabolism via angiopoietin-like proteins," Biochem. Soc. Trans., 33: 1059-1062 (2005).
Kim et al., "Molecular cloning, expression, and characterization of angiopoietin-related protein," J. Biol. Chem., 274: 26523-26528 (1999).
Koishi et al., "Angptl3 regulates lipid metabolism in mice," Nat. Genet., 30: 151-157 (2002).
Korstanje et al., "Locating Ath8, a locus for murine atherosclerosis susceptibility and testing several of its candidate genes in mice and humans," Atherosclerosis, 177: 443-450 (2004).
Koster et al., "Transgenic angiopoietin-like (Angptl) overexpression and targeted disruption of Angptl4 and Angptl3: regulation of triglyceride metabolism," Endocrynology, 146: 4943-4950 (2005).
Li, "Genetics and regulation of angiopoietin-like proteins 3 and 4," Curr. Opin. Lipidol., 17: 152-156 (2006).
Oike et al., "Angiopoietin-like proteins: potential new targets for metabolic syndrome therapy," Trends Mol. Med., 11: 473-479 (2005).
Ono et al., "Protein region important for regulation of lipid metabolism in angiopoietin-like 3 (ANGPTL3)," J. Biol. Chem., 278: 41804-41809 (2003).
Shimamura et al., "Angiopoietin-like protein 3, a hepatic secretory factor, activates lipolysis in adipocytes," Biochem. Biophys. Res. Comm., 301: 604-609 (2003).
Shimamura et al., "Leptin and insulin down-regulate angiopoietin-like protein 3, a plasma triglyceride-increasing factor," Biochem. Biophys. Res. Comm., 322: 1080-1085 (2004).
Shimizugawa et al., "ANGPTL3 decreases very low density lipoprotein triglyceride clearance by inhibition of lipoprotein lipase," J. Biol. Chem., 277: 33742-33748 (2002).
Willer at al., "Newly identified loci that influence lipid concentrations and risk of coronary artery disease," Nat. Genet., 40: 161-169 (2008).

(Continued)

*Primary Examiner* — Sharon Wen
(74) *Attorney, Agent, or Firm* — Casimir Jones, S.C.

(57) ABSTRACT

Monoclonal antibodies that specifically bind to ANGPTL3 are provided. Monoclonal antibodies that neutralize at least one activity of ANGPTL3 are provided. Methods of treating a disorder of lipid metabolism using neutralizing monoclonal antibodies are provided.

17 Claims, 19 Drawing Sheets

(56) References Cited

OTHER PUBLICATIONS

Yoshida et al., "Angiopoietin-like protein 4 is a potent hyperlipidemia-inducing factor in mice and inhibitor of lipoprotein lipase," J. Lipid Res., 43: 1770-1772 (2002).

Buranda et al., Detection of epitope tagged proteins in flow cytometry; fluorescence resonance energy transfer based assays on beads with femtomole resolution, Anal Biochem, 2001, 298(2): 151-62; Abstract.

International Search Report and Written Opinion for Applications No. PCT/US2007/025080 dated Nov. 4, 2009 (13 pages).

Sonnenburg et al., Glycosylphosphatidylinositol-anchored HDL-binding protein stabilizes lipoprotein lipase and prevents its inhibition by angiopoietin-like 3 and angiopoietin-like 4, Lipid Res., downloaded Oct. 21, 2009, pp. 1-41.

* cited by examiner

MONOCLONAL ANTIBODIES AGAINST ANGPTL3

This application is a continuation of U.S. patent application Ser. No. 12/001,012, filed Dec. 6, 2007, U.S. Pat. No. 7,935,796 which claims the benefit of U.S. Provisional Application No. 60/873,834, filed Dec. 8, 2006. U.S. patent application Ser. No. 12/001,012 and U.S. Provisional Application No. 60/873,834 are incorporated by reference herein for any purpose.

I. TECHNICAL FIELD

Monoclonal antibodies that specifically bind to angiopoietin-like protein 3 (ANGPTL3) are provided. Methods of using monoclonal antibodies that specifically bind to angiopoietin-like protein 3 (ANGPTL3) are provided. Pharmaceutical compositions comprising monoclonal antibodies that specifically bind to angiopoietin-like protein 3 (ANGPTL3) are provided.

II. INTRODUCTION

Angiopoietin-like protein 3 (ANGPTL3) is conserved among several mammalian species. Li, C. (2006) *Curr. Opin. Lipidol.* 17(2):152-156. ANGPTL3 contains an N-terminal coiled-coil domain and a C-terminal fibrinogen-like domain. Conklin, D. et al. (1999) *Genomics* 62:477-482. The N-terminal coiled-coil domain mediates oligomerization of ANGPTL3. Ge, H. et al. (2005) *J. Lipid Res.* 46(7):1484-1490. Oligomerized ANGPTL3 undergoes proteolytic processing in vivo, resulting in the cleavage of the fibrinogen-like domain. Ono M. et al. (2003) *J. Biol. Chem.* 278(43):41804-41809.

ANGPTL3 is expressed primarily in the liver. Koishi, R. et al. (2002) *Nat. Genet.* 30(2):151-157. ANGPTL3 appears to inhibit lipoprotein lipase (LPL) activity and decreases very low density lipoprotein (VLDL) clearance. Shimizugawa T. et al. (2002) *J. Biol. Chem.* 277(37):33742-33748. The KK/San spontaneous mutant mouse contains an insertion in exon 6 of the Angptl3 gene and shows notable serum hypolipidemia. Koishi et al. (2002) *Nat. Genet.*, 30(2):151-157. Adenoviral-mediated expression of ANGPTL3 or direct administration of ANGPTL3 reversed the hypolipidemia in KK/San mice. Koishi et al. (2002) *Nat. Genet.* 30(2):151-157. An Angptl3 knockout mouse has been shown to have reduced triglyceride levels in fed male mice and in fed or fasted female mice. Koster, A. et al., (2005) *Endocrinol.* 146:4943-4950. Those mice have also been shown to have reduced cholesterol levels in both fed and fasted male and female mice. Koster, A. et al., (2005) Endocrinol. 146:4943-4950. Angptl3 expression has been shown to be increased in both streptozotocin diabetic mice, in db/db mice, and in ob/ob mice. Inukai, K. et al., (2004) *Biochem. Biophys. Res. Comm.* 317(4):10751079; Shimamura, M. et al. (2004) *Biochem. Biophys. Res. Comm.* 322(3):1080-1085.

III. SUMMARY

In certain embodiments, a monoclonal antibody that binds to ANGPTL3 and neutralizes at least one activity of ANGPTL3 is provided. In certain embodiments, the monoclonal antibody is a mouse monoclonal antibody. In certain embodiments, the monoclonal antibody is a humanized monoclonal antibody. In certain embodiments, the monoclonal antibody is a human monoclonal antibody. In certain embodiments, the monoclonal antibody decreases the level of at least one serum lipid in vivo.

In certain embodiments, the monoclonal antibody binds to an epitope of ANGPTL3 having the amino acid sequence of SEQ ID NO: 59. In certain embodiments, the monoclonal antibody binds to an epitope of ANGPTL3 having the amino acid sequence of SEQ ID NO: 60. In certain embodiments, the monoclonal antibody binds to an epitope of ANGPTL3 having the amino acid sequence of SEQ ID NO: 9. In certain embodiments, the monoclonal antibody binds to an epitope of ANGPTL3 having the amino acid sequence of SEQ ID NO: 10.

In certain embodiments, the monoclonal antibody comprises a heavy chain variable region comprising the amino acid sequence of SEQ ID NO: 20 and a light chain variable region comprising the amino acid sequence of SEQ ID NO: 28. In certain embodiments, the monoclonal antibody comprises a heavy chain variable region comprising the amino acid sequence of SEQ ID NO: 22 and a light chain variable region comprising the amino acid sequence of SEQ ID NO: 30. In certain embodiments, the monoclonal antibody comprises a heavy chain variable region comprising the amino acid sequence of SEQ ID NO: 24 and a light chain variable region comprising the amino acid sequence of SEQ ID NO: 32. In certain embodiments, the monoclonal antibody comprises a heavy chain variable region comprising the amino acid sequence of SEQ ID NO: 64 and a light chain variable region comprising the amino acid sequence of SEQ ID NO: 68. In certain embodiments, the monoclonal antibody comprises a heavy chain variable region comprising the amino acid sequence of SEQ ID NO: 66 and a light chain variable region comprising the amino acid sequence of SEQ ID NO: 70.

In certain embodiments, the monoclonal antibody specifically binds to the same epitope as antibody 4.7.1. In certain embodiments, the monoclonal antibody specifically binds to the same epitope as antibody 4.8.3. In certain embodiments, the monoclonal antibody specifically binds to the same epitope as antibody 4.9.1. In certain embodiments, the monoclonal antibody specifically binds to the same epitope as antibody 1.315.1. In certain embodiments, the monoclonal antibody specifically binds to the same epitope as antibody 5.35. In certain embodiments, the monoclonal antibody specifically binds to the same epitope as antibody 5.50.

In certain embodiments, the monoclonal antibody is an antibody fragment. In certain embodiments, the monoclonal antibody is a scFv fragment. In certain embodiments, the monoclonal antibody is a Fab fragment. In certain embodiments, the monoclonal antibody is a F(ab')$_2$ fragment. In certain embodiments, the monoclonal antibody is a Fab' fragment.

In certain embodiments, an isolated antibody that specifically binds to ANGPTL3 is provided, comprising a heavy chain and a light chain, wherein the heavy chain comprises: a) an amino acid sequence as set forth in any one of SEQ ID NOs: 19 to 26 and 63 to 66; b) at least one amino acid sequence as set forth in SEQ ID NOs: 35, 36, and 37; c) at least one amino acid sequence set forth in SEQ ID NOs: 38, 39, and 40; d) at least one amino acid sequence as set forth in SEQ ID NOs: 41, 42, or 43; e) at least one amino acid sequence as set forth in SEQ ID NOs: 53, 54, and 55; f) at least one amino acid sequence as set forth in SEQ ID NOs: 71, 72, and 73; or g) at least one amino acid sequence as set forth in SEQ ID NOs: 74, 75, and 76; wherein the antibody neutralizes at least one activity of ANGPTL3. In certain embodiments, the heavy chain of the antibody comprises a CDR1 as set forth in SEQ ID NO: 35, a CDR2 as set forth in SEQ ID NO: 36, and a CDR3 as set forth in SEQ ID NO: 37. In certain embodiments, the heavy chain of the antibody comprises a CDR1 as set forth in SEQ ID NO: 38, a CDR2 as set forth in SEQ ID NO: 39, and a CDR3 as set forth in SEQ ID NO: 40. In certain embodiments, the heavy chain of the antibody comprises a CDR1 as set forth in SEQ ID NO: 41, a CDR2 as set forth in SEQ ID NO: 42, and a CDR3 as set forth in SEQ ID NO: 43. In certain embodiments, the heavy chain of the antibody comprises a CDR1 as set forth in SEQ ID NO: 53, a CDR2 as set forth in SEQ ID NO: 54, and a CDR3 as set forth in SEQ ID NO: 55. In certain embodiments, the heavy chain of the antibody comprises a CDR1 as set forth in SEQ ID NO: 71, a CDR2 as set forth in SEQ ID NO: 72, and a CDR3 as set forth in SEQ ID NO: 73. In certain embodiments, the heavy chain of the antibody comprises a CDR1 as set forth in SEQ ID NO: 74, a CDR2 as set forth in SEQ ID NO: 75, and a CDR3 as set forth in SEQ ID NO: 76.

In certain embodiments, an isolated antibody that specifically binds to ANGPTL3 is provided, comprising a heavy chain and a light chain, wherein the heavy chain comprises: a) an amino acid sequence as set forth in any one of SEQ ID NOs: 19 to 26 and 63 to 66; b) at least one amino acid sequence as set forth in SEQ ID NOs: 35, 36, and 37; c) at least one amino acid sequence set forth in SEQ ID NOs: 38, 39, and 40; d) at least one amino acid sequence as set forth in SEQ ID NOs: 41, 42, or 43; e) at least one amino acid sequence as set forth in SEQ ID NOs: 53, 54, and 55; f) at least one amino acid sequence as set forth in SEQ ID NOs: 71, 72, and 73; or g) at least one amino acid sequence as set forth in SEQ ID NOs: 74, 75, and 76; wherein the antibody neutralizes at least one activity of ANGPTL3; and wherein the light chain comprises: a) an amino acid sequence as set forth in any one of SEQ ID NOs: 27 to 34 and 67 to 70; b) at least one amino acid sequence as set forth in SEQ ID NOs: 44, 45, and 46; c) at least one amino acid sequence set forth in SEQ ID NOs: 47, 48, and 49; d) at least one amino acid sequence as set forth in SEQ ID NOs: 50, 51, or 52; e) at least one amino acid sequence as set forth in SEQ ID NOs: 56, 57, and 58; f) at least one amino acid sequence as set forth in SEQ ID NOs: 77, 78, and 79; or g) at least one amino acid sequence as set forth in SEQ ID NOs: 80, 81, and 82. In certain embodiments, the heavy chain of the antibody comprises a CDR1 as set forth in SEQ ID NO: 35, a CDR2 as set forth in SEQ ID NO: 36, and a CDR3 as set forth in SEQ ID NO: 37; and the light chain of the antibody comprises a CDR1 as set forth in SEQ ID NO: 44, a CDR2 as set forth in SEQ ID NO: 45, and a CDR3 as set forth in SEQ ID NO: 46. In certain embodiments, the heavy chain of the antibody comprises a CDR1 as set forth in SEQ ID NO: 38, a CDR2 as set forth in SEQ ID NO: 39, and a CDR3 as set forth in SEQ ID NO: 40; and the light chain of the antibody comprises a CDR1 as set forth in SEQ ID NO: 47, a CDR2 as set forth in SEQ ID NO: 48, and a CDR3 as set forth in SEQ ID NO: 49. In certain embodiments, the heavy chain of the antibody comprises a CDR1 as set forth in SEQ ID NO: 41, a CDR2 as set forth in SEQ ID NO: 42, and a CDR3 as set forth in SEQ ID NO: 43; and the light chain of the antibody comprises a CDR1 as set forth in SEQ ID NO: 50, a CDR2 as set forth in SEQ ID NO: 51, and a CDR3 as set forth in SEQ ID NO: 52. In certain embodiments, the heavy chain of the antibody comprises a CDR1 as set forth in SEQ ID NO: 53, a CDR2 as set forth in SEQ ID NO: 54, and a CDR3 as set forth in SEQ ID NO: 55, and the light chain of the antibody comprises a CDR1 as set forth in SEQ ID NO: 56, a CDR2 as set forth in SEQ ID NO: 57, and a CDR3 as set forth in SEQ ID NO: 58. In certain embodiments, the heavy chain of the antibody comprises a CDR1 as set forth in SEQ ID NO: 71, a CDR2 as set forth in SEQ ID NO: 72, and a CDR3 as set forth in SEQ ID NO: 73, and the light chain of the antibody comprises a CDR1 as set forth in SEQ ID NO: 77, a CDR2 as set forth in SEQ ID NO: 78, and a CDR3 as set forth in SEQ ID NO: 79. In certain embodiments, the heavy chain of the antibody comprises a CDR1 as set forth in SEQ ID NO: 74, a CDR2 as set forth in SEQ ID NO: 75, and a CDR3 as set forth in SEQ ID NO: 76, and the light chain of the antibody comprises a CDR1 as set forth in SEQ ID NO: 80, a CDR2 as set forth in SEQ ID NO: 81, and a CDR3 as set forth in SEQ ID NO: 82.

In certain embodiments, an isolated antibody that specifically binds to ANGPTL3 is provided, comprising a heavy chain and a light chain, wherein the light chain comprises: a) an amino acid sequence as set forth in any one of SEQ ID NOs: 27 to 34 and 67 to 70; b) at least one amino acid sequence as set forth in SEQ ID NOs: 44, 45, and 46; c) at least one amino acid sequence set forth in SEQ ID NOs: 47, 48, and 49; d) at least one amino acid sequence as set forth in SEQ ID NOs: 50, 51, or 52; e) at least one amino acid sequence as set forth in SEQ ID NOs: 56, 57, and 58; f) at least one amino acid sequence as set forth in SEQ ID NOs: 77, 78, and 79; or g) at least one amino acid sequence as set forth in SEQ ID NOs: 80, 81, and 82; wherein the antibody neutralizes at least one activity of ANGPTL3. In certain embodiments, the light chain of the antibody comprises a CDR1 as set forth in SEQ ID NO: 44, a CDR2 as set forth in SEQ ID NO: 45, and a CDR3 as set forth in SEQ ID NO: 46. In certain embodiments, the light chain of the antibody comprises a CDR1 as set forth in SEQ ID NO: 47, a CDR2 as set forth in SEQ ID NO: 48, and a CDR3 as set forth in SEQ ID NO: 49. In certain embodiments, the light chain comprises a CDR1 as set forth in SEQ ID NO: 50, a CDR2 as set forth in SEQ ID NO: 51, and a CDR3 as set forth in SEQ ID NO: 52. In certain embodiments, the light chain comprises a CDR1 as set forth in SEQ ID NO: 56, a CDR2 as set forth in SEQ ID NO: 57, and a CDR3 as set forth in SEQ ID NO: 58. In certain embodiments, the light chain comprises a CDR1 as set forth in SEQ ID NO: 77, a CDR2 as set forth in SEQ ID NO: 78, and a CDR3 as set forth in SEQ ID NO: 79. In certain embodiments, the light chain comprises a CDR1 as set forth in SEQ ID NO: 80, a CDR2 as set forth in SEQ ID NO: 81, and a CDR3 as set forth in SEQ ID NO: 82.

In certain embodiments, a monoclonal antibody that bind to ANGPTL3 and neutralizes at least one activity of ANGPTL3 is provided, wherein the affinity of the antibody for a peptide having an amino acid sequence of SEQ ID NO: 9 is at least at least 3-fold greater than the affinity of the antibody for a peptide having an amino acid sequence of any one of SEQ ID NO: 84, SEQ ID NO: 85, SEQ ID NO: 86, SEQ ID NO: 87, SEQ ID NO: 88, SEQ ID NO: 90, and SEQ ID NO: 92. In certain embodiments, the affinity of the antibody for a peptide having an amino acid sequence of SEQ ID NO: 9 is at least at least 3-fold greater than the affinity of the antibody for each of SEQ ID NO: 85, SEQ ID NO: 86, SEQ ID NO: 87, SEQ ID NO: 88, and SEQ ID NO: 90. In certain embodiments, a monoclonal antibody that bind to ANGPTL3 and neutralizes at least one activity of ANGPTL3 is provided, wherein the antibody binds to a peptide having the amino acid sequence of SEQ ID NO: 9 with a $K_D$ of less than 50 nM. In certain embodiments, the antibody binds to a peptide having the amino acid sequence of SEQ ID NO: 9 with a $K_D$ of less than 30 nM. In certain embodiments, the antibody binds to a peptide having the amino acid sequence of SEQ ID NO: 9 with a $K_D$ of less than 10 nM. In certain embodiments, the antibody binds to a peptide having the amino acid sequence of SEQ ID NO: 9 with a $K_D$ of less than 5 nM.

In certain embodiments, a pharmaceutical composition is provided comprising an antibody as described above. In certain embodiments, a method of treating a disorder of lipid metabolism is provided, wherein the method comprises administering to a patient an effective amount of the pharmaceutical composition. In certain embodiments, a method of decreasing the level of one or more serum lipids is provided, wherein the method comprises administering to a patient an effective amount of the pharmaceutical composition. In certain embodiments, a method of treating hypertriglyceridemia is provided, wherein the method comprises administering to a patient an effective amount of the pharmaceutical composition. In certain embodiments, a method of treating hypercholesterolemia is provided, wherein the method comprises administering to a patient an effective amount of the pharmaceutical composition. In certain embodiments, a method of treating obesity is provided, wherein the method comprises administering to a patient an effective amount of the pharmaceutical composition. In certain embodiments, a method of treating diabetes is provided, wherein the method comprises administering to a patient an effective amount of the pharmaceutical composition. In certain embodiments, a method of treating ischaemic heart disease is provided, wherein the method comprises administering to a patient an effective amount of the pharmaceutical composition. In certain embodiments, a method of treating metabolic syndrome is provided, wherein the method comprises administering to a patient an effective amount of the pharmaceutical composition.

IV. BRIEF DESCRIPTION OF THE FIGURES

Figure 7:
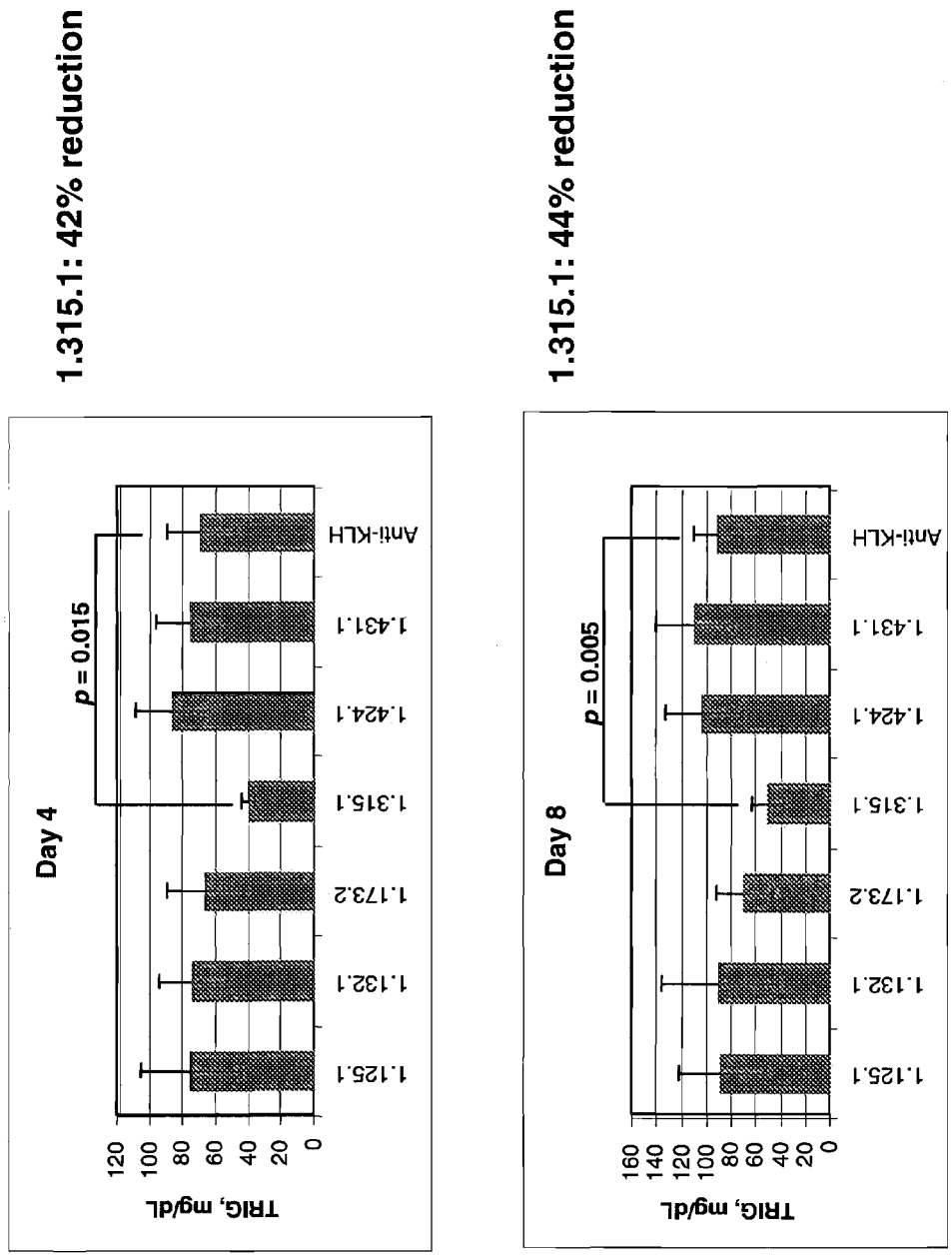

FIG. 7 shows serum triglyceride levels in mice 4 days (top panel) and 8 days (bottom panel) after injection with antibodies 1.125.1, 1.132.1, 1.173.2, 1.315.1, 1.424.1, 1.431.1, and control antibody anti-KLH, as described in Example J.

Figure 8:
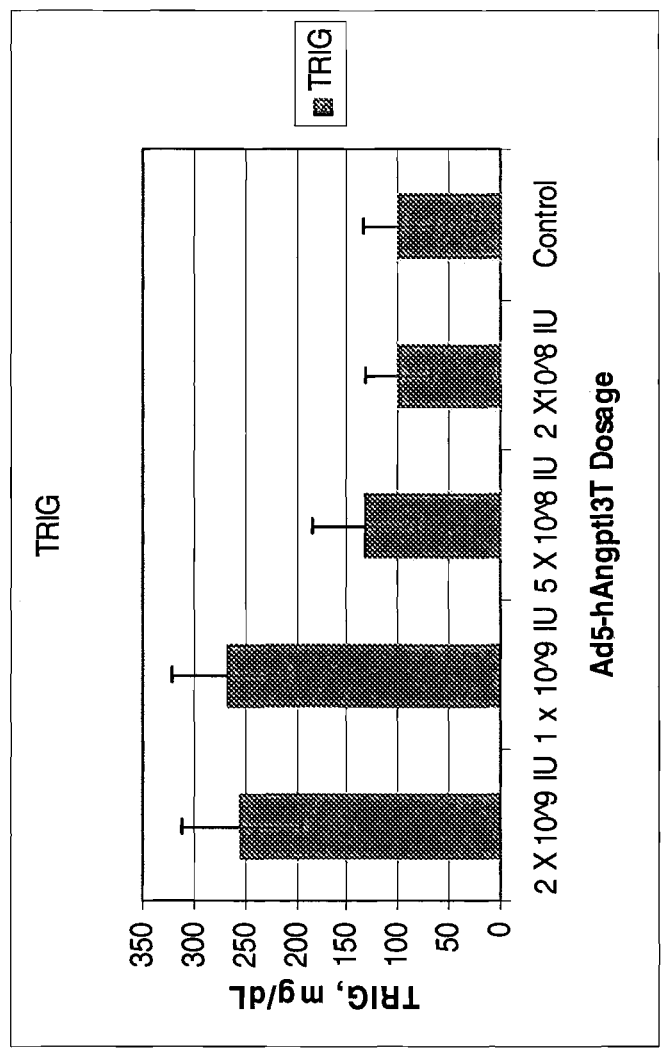

FIG. 8 shows serum triglyceride levels in mice after injection with various dosages of Ad5-hAngptl3T virus or $2\times10^9$ vp of control virus, as described in Example B.

Figure 9:
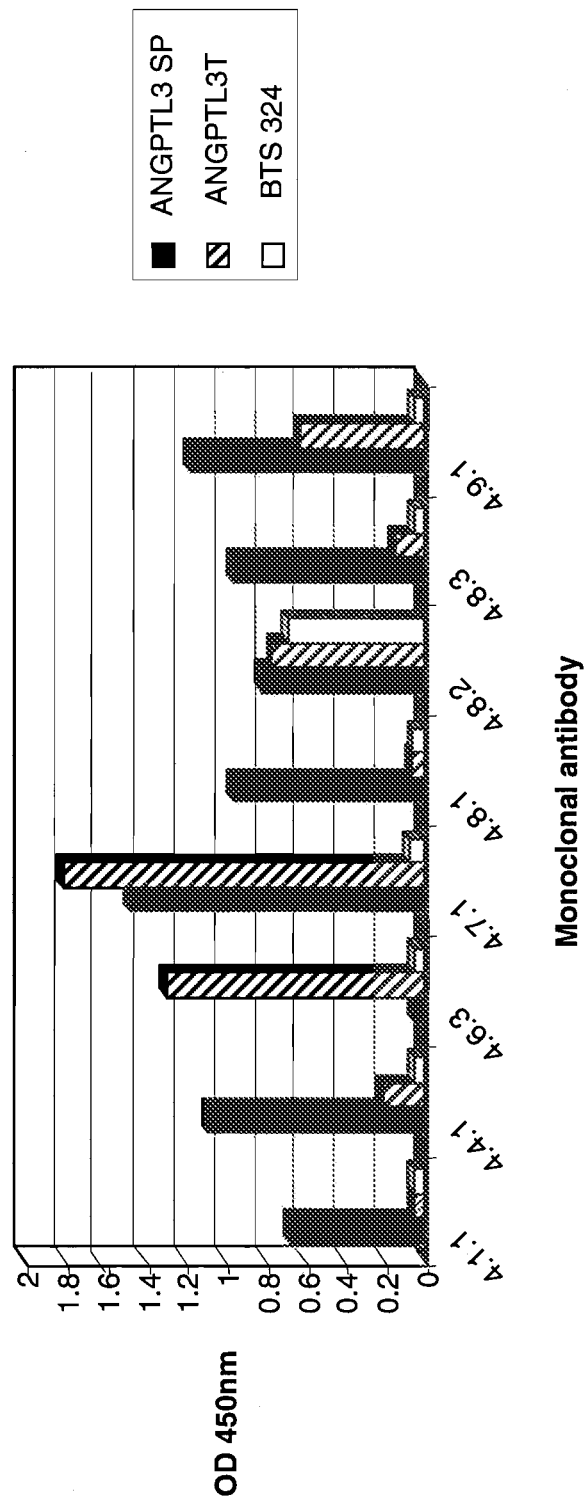

FIG. 9 shows binding of antibodies 4.1.1, 4.4.1, 4.6.3, 4.7.1, 4.8.1, 4.8.2, 4.8.3, and 4.9.1 to ANGPTL3 SP1, ANGPTL3T, and control protein BTS324, as described in Example H.

Figure 10:
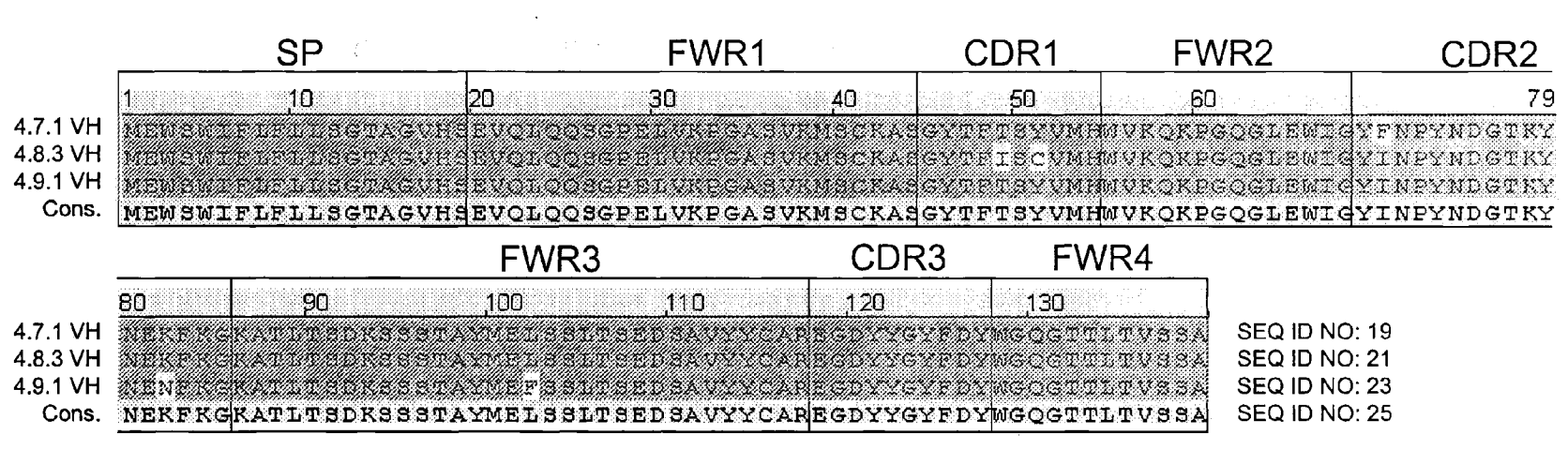

FIG. 10 shows an alignment of the heavy chain variable regions of antibodies 4.7.1 (SEQ ID NO: 19), 4.8.3 (SEQ ID NO: 21), and 4.9.1 (SEQ ID NO: 23). The heavy chain consensus sequence is also shown (SEQ ID NO: 25), as well as the regions of the heavy chain sequences corresponding to the signal peptide (SP), framework region 1 (FWR1), complementarity-determining region 1 (CDR1), framework region 2 (FWR2), complementarity-determining region 2 (CDR2), framework region 3 (FWR3), complementarity-determining region 3 (CDR3), and framework region 4 (FWR4).

Figure 11:
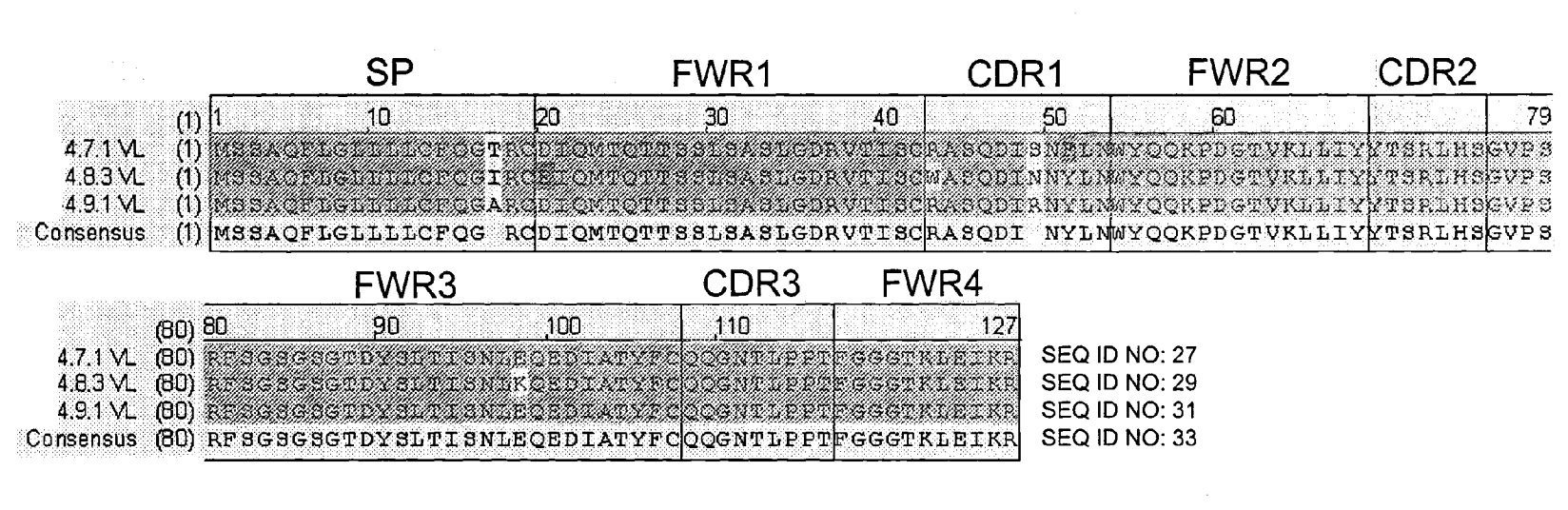

FIG. 11 shows an alignment of the light chain variable regions of antibodies 4.7.1 (SEQ ID NO: 27), 4.8.3 (SEQ ID NO: 29), and 4.9.1 (SEQ ID NO: 31). The light chain consensus sequence is also shown (SEQ ID NO: 33), as well as the regions of the light chain sequences corresponding to the signal peptide (SP), framework region 1 (FWR1), complementarity-determining region 1 (CDR1), framework region 2 (FWR2), complementarity-determining region 2 (CDR2), framework region 3 (FWR3), complementarity-determining region 3 (CDR3), and framework region 4 (FWR4).

Figure 12:
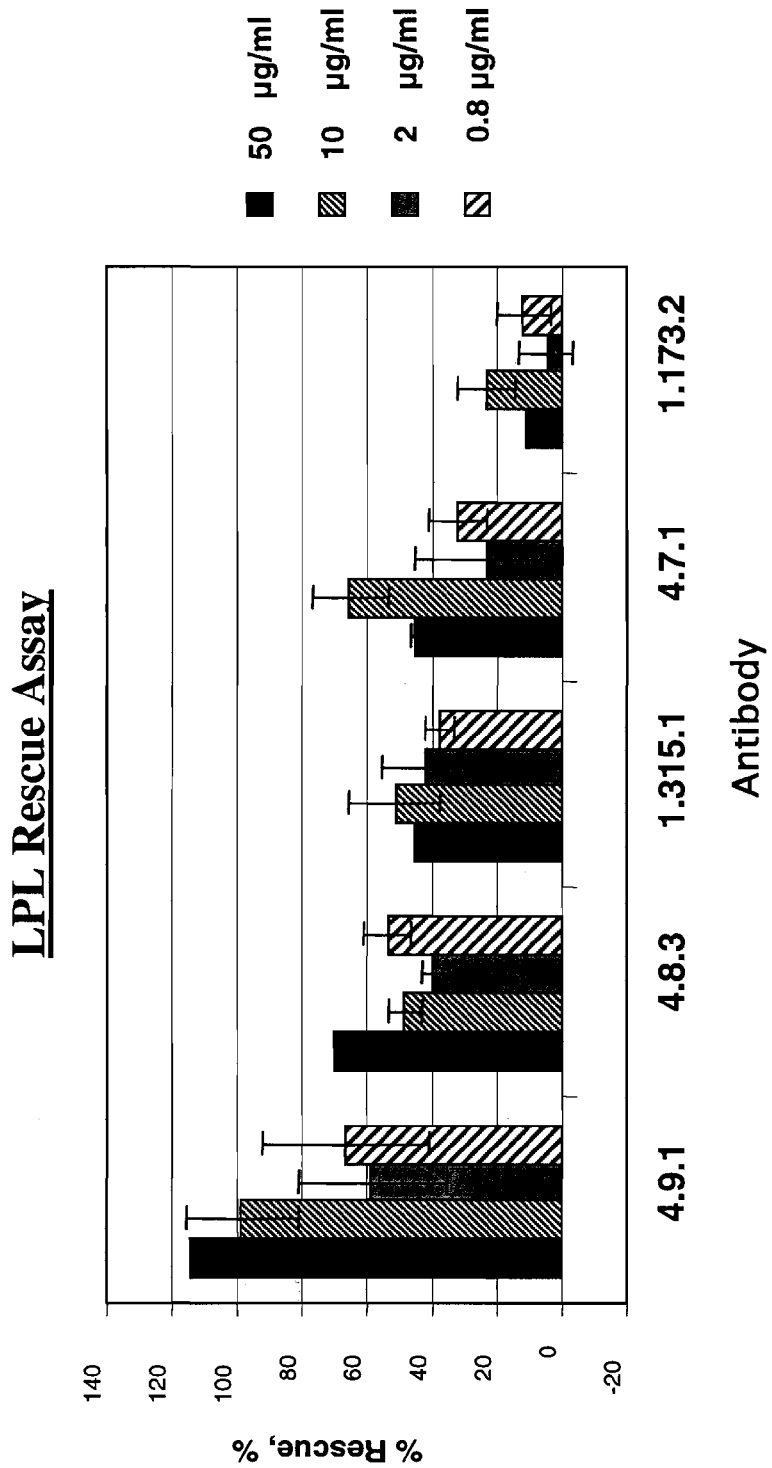

FIG. 12 shows LPL activity in vitro after treatment with mouse monoclonal anti-ANGPTL3 antibodies 4.9.1, 4.8.3, 1.315.1, 4.7.1, and 1.173.2, as described in Example L.

Figure 13:
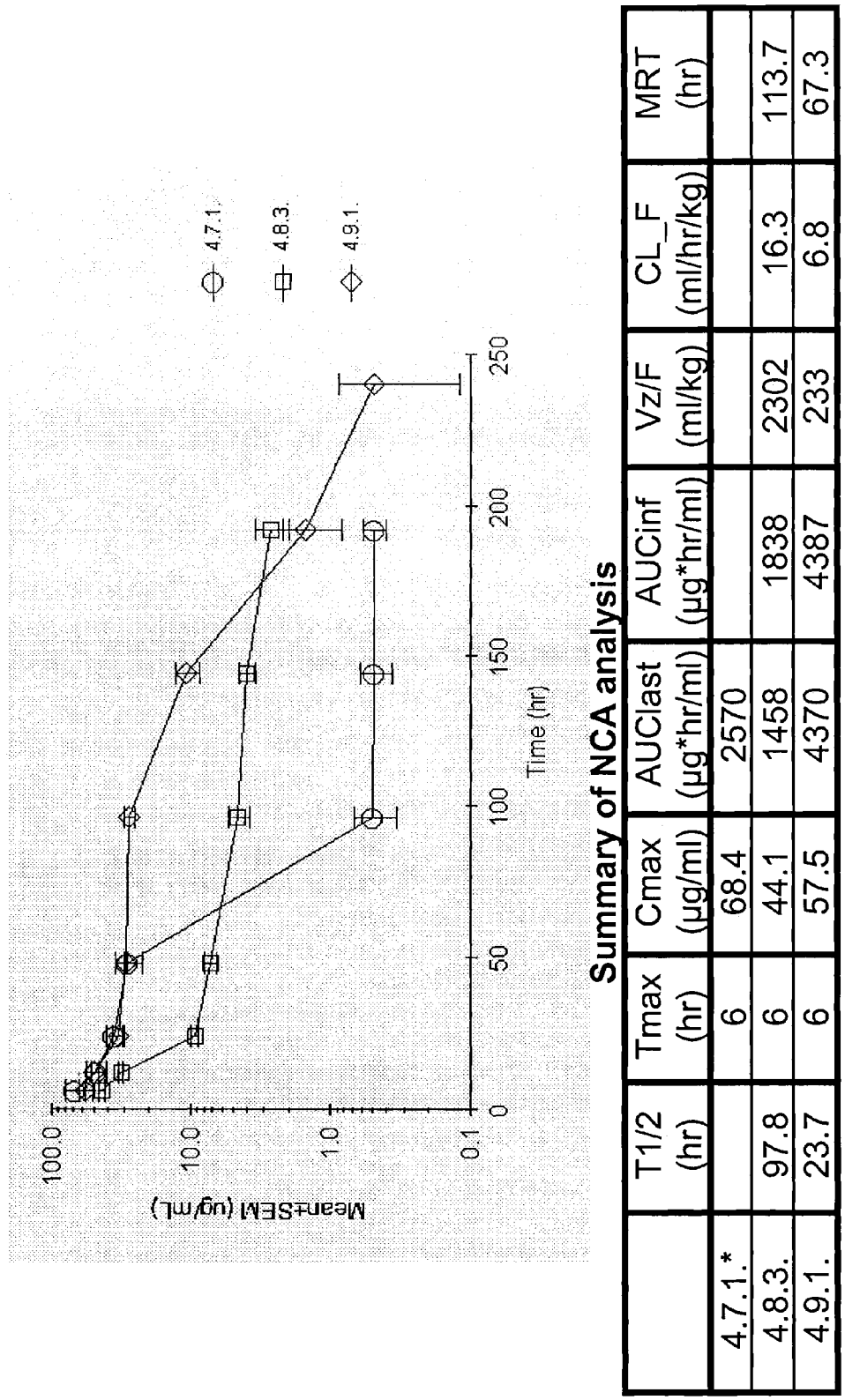

FIG. 13 shows the in vivo pharmacokinetics of certain mouse monoclonal anti-ANGPTL3 antibodies, as described in Example N.

Figure 14:
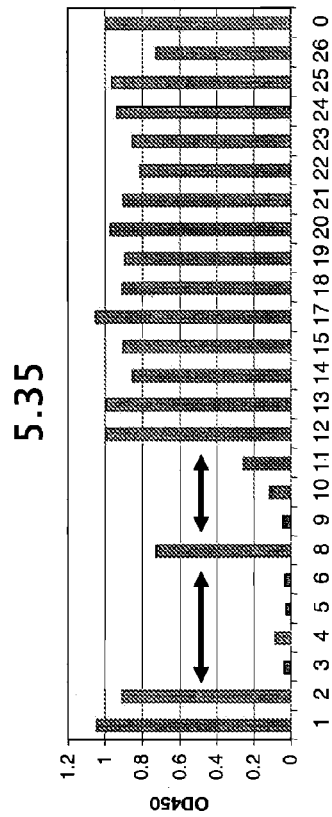
Figure 14:
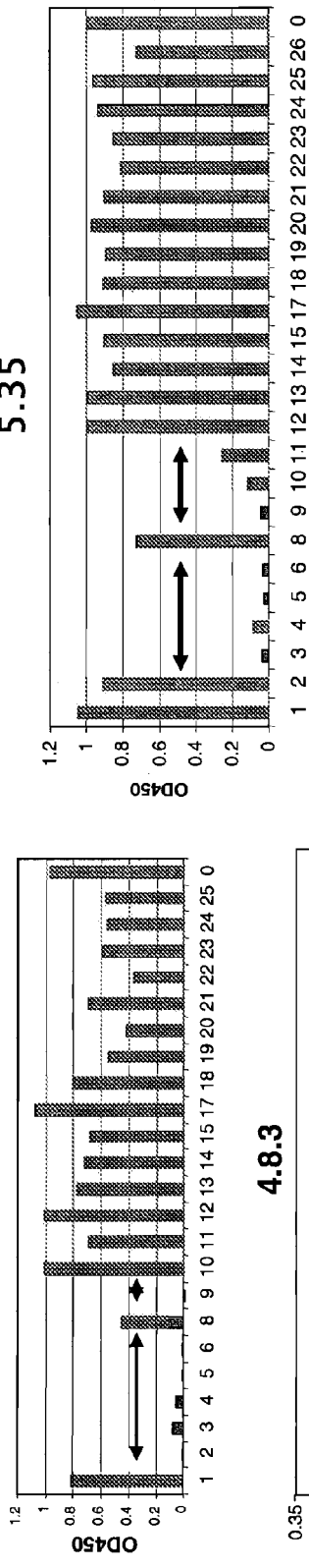
Figure 14:
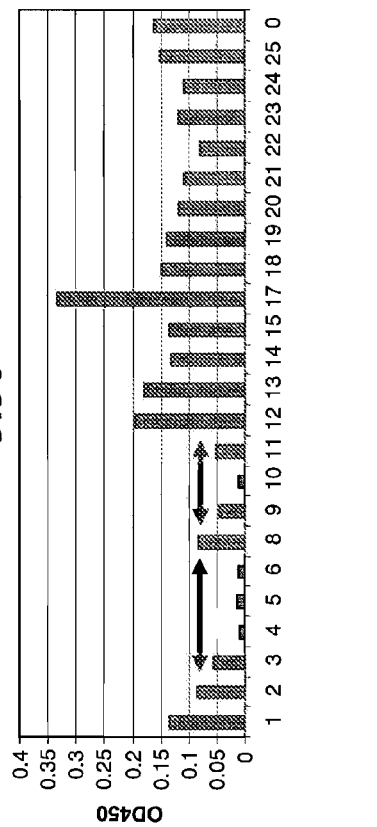
Figure 14:
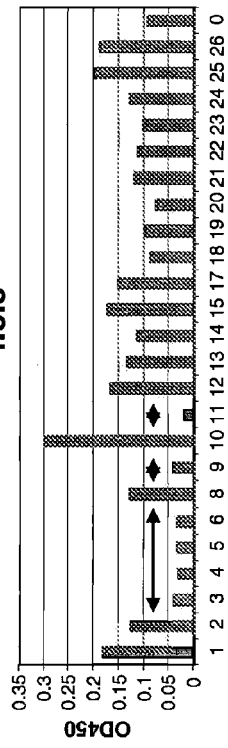
Figure 14:
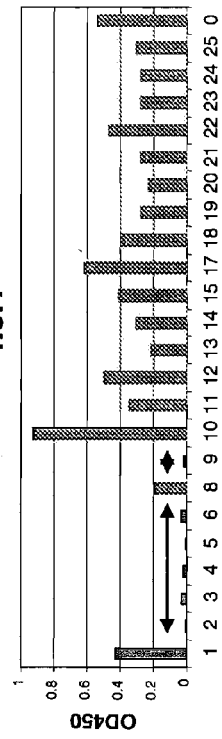

FIG. 14 shows binding of antibodies 4.7.1, 4.8.3, 4.9.1, 5.35, and 5.50 to the alanine-scanning mutants of the SP1 peptide, as described in Example H.

Figure 15:
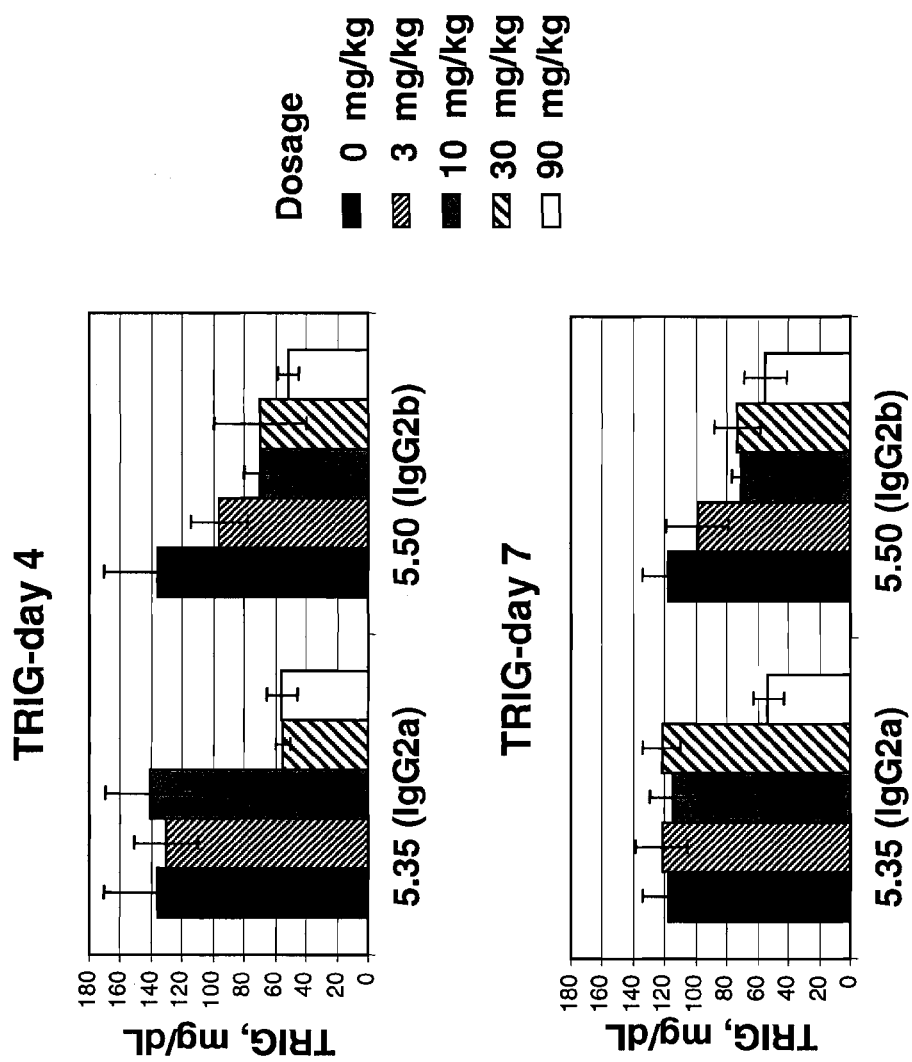

FIG. 15 shows serum triglyceride levels in mice 4 days (top panel) and 7 days (bottom panel) after injection with antibody 5.35 or 5.50, as described in Example J.

Figure 16:
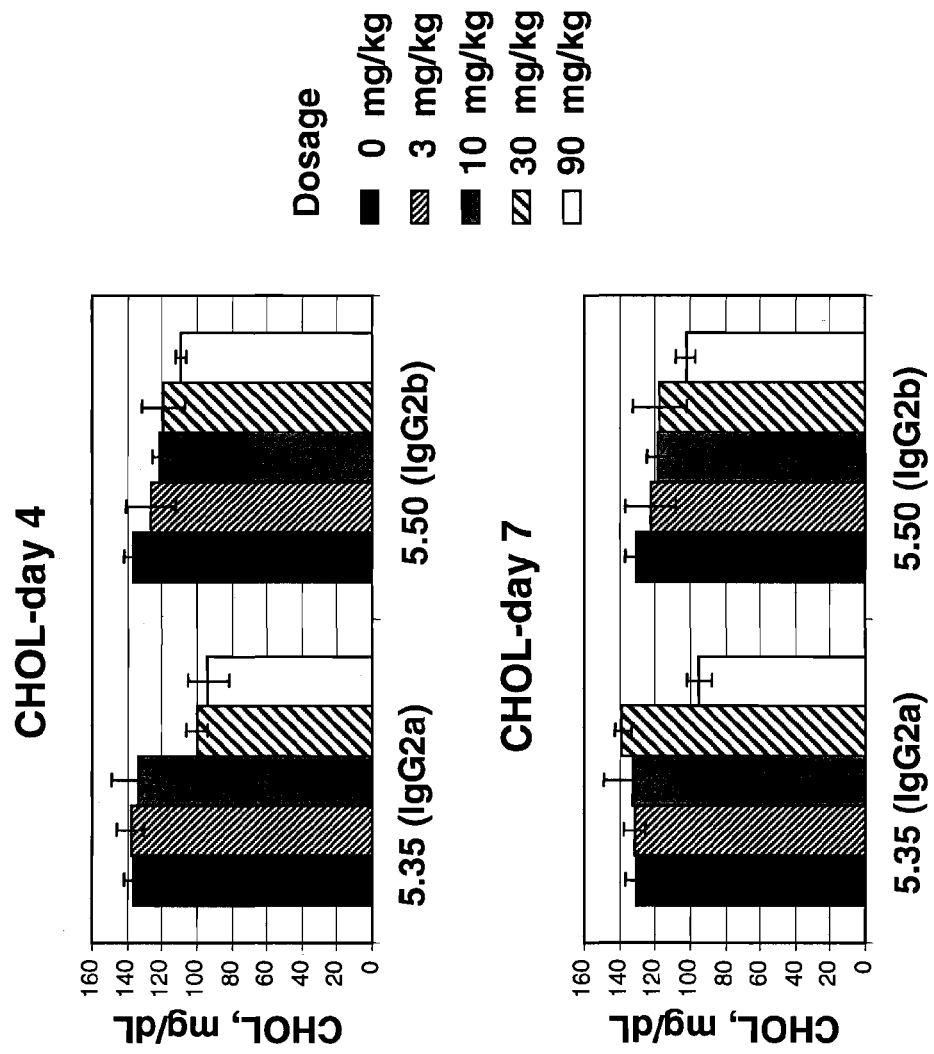

FIG. 16 shows serum cholesterol levels in mice 4 days (top panel) and 7 days (bottom panel) after injection with antibody 5.35 or 5.50, as described in Example J.

Figure 17:
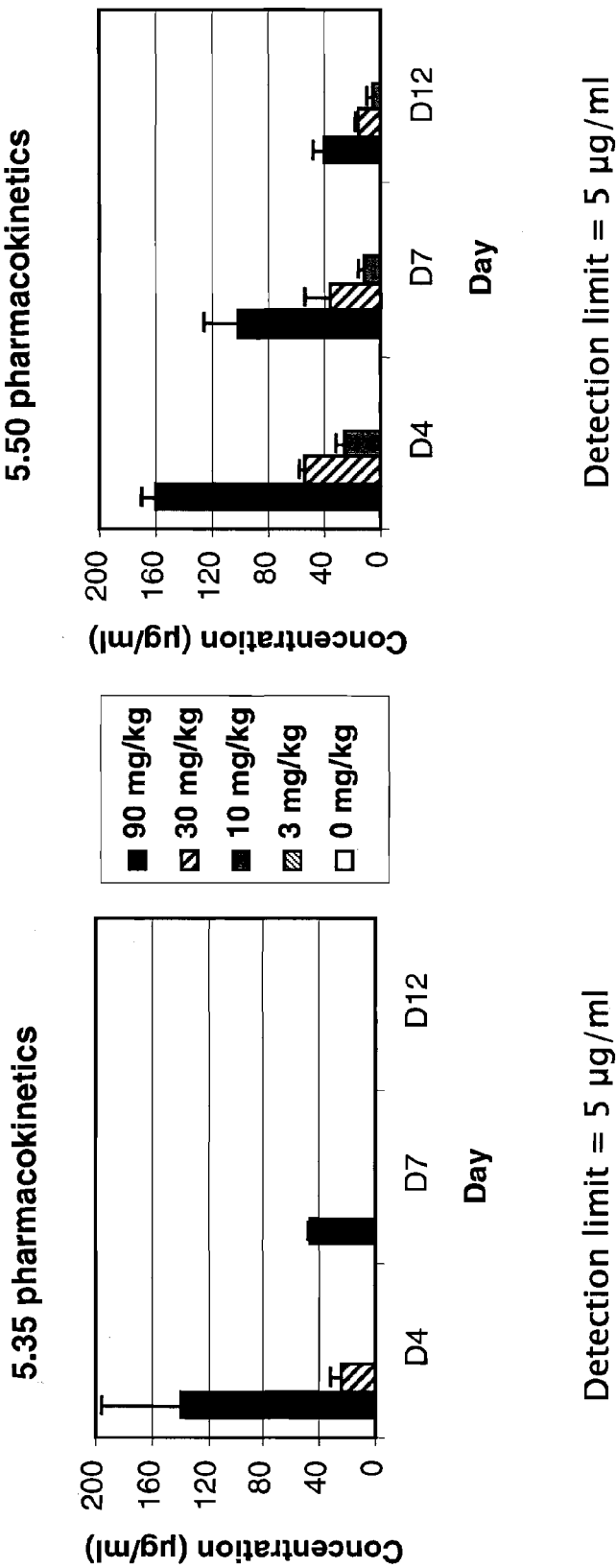

FIG. 17 shows the in vivo pharmacokinetics of antibodies 5.35 and 5.50, as described in Example N.

Figure 18:
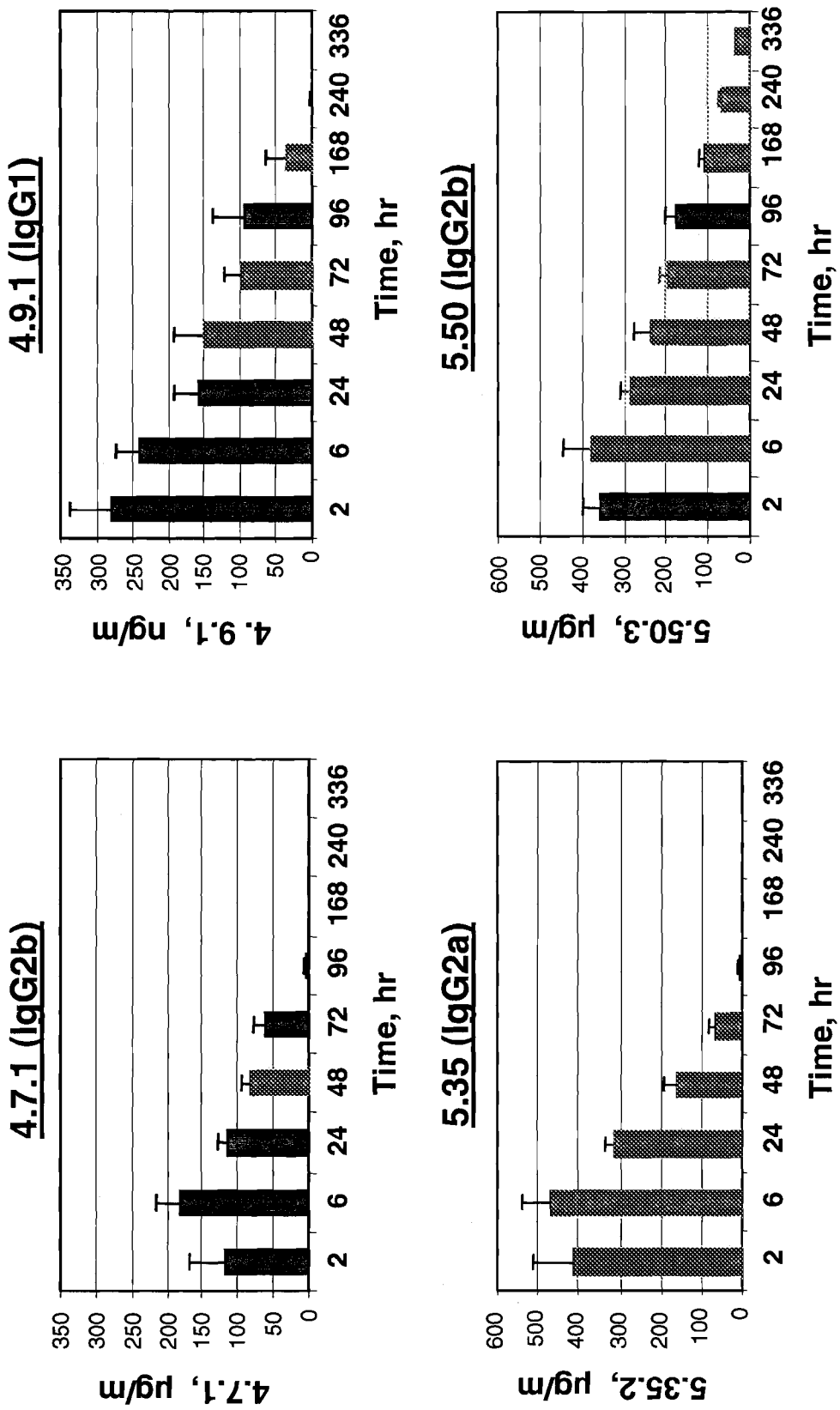

FIG. 18 shows the in vivo pharmacokinetics of antibodies 4.7.1, 4.9.1, 5.35, and 5.50, as described in Example N.

Figure 19:
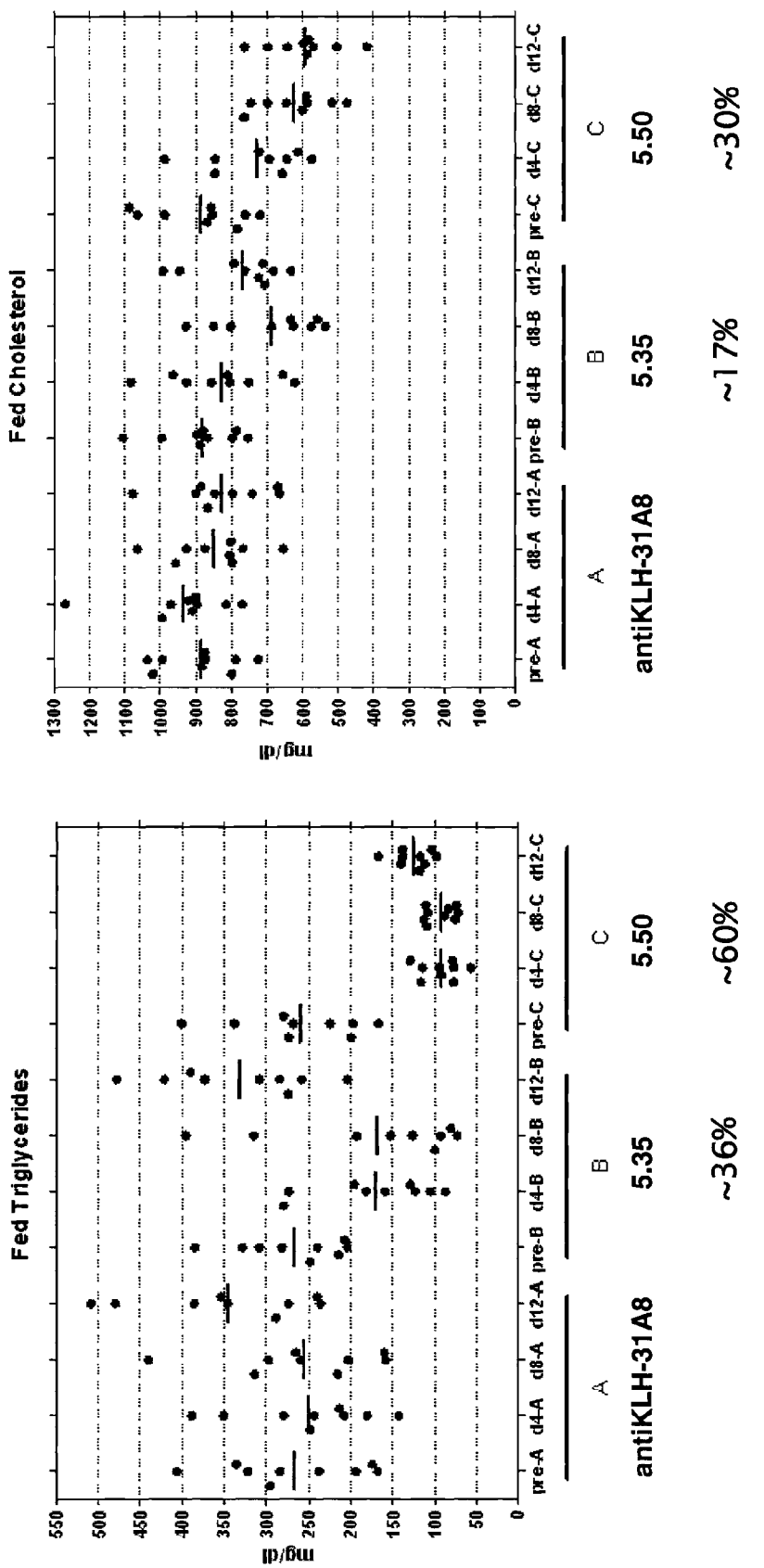

FIG. 19 shows the reduction in serum triglycerides and serum cholesterol in ApoE mice injected with antibodies 5.35 and 5.50 and control antibody anti-KLH.

V. DETAILED DESCRIPTION OF VARIOUS EMBODIMENTS

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated literature and similar materials defines a term that contradicts that term's definition in this application, this application controls.

A. Certain definitions

The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

The term "antibody," as used herein, refers to an intact antibody or a fragment of an antibody that competes with the intact antibody for antigen binding. Antibody fragments include, but are not limited to, Fab, Fab', F(ab')$_2$, Fv, scFv, Fd, diabodies, and other antibody fragments that retain at least a portion of the variable region of an intact antibody. See, e.g., Hudson et al. (2003) *Nat. Med.* 9:129-134. In certain embodiments, antibody fragments are produced by enzymatic or chemical cleavage of intact antibodies. In certain embodiments, antibody fragments are produced by recombinant DNA techniques.

The term "native polypeptide" refers to a naturally occurring polypeptide. The term "native antibody" refers to a naturally occurring antibody.

The term "monoclonal antibody" refers to an antibody from a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) *Nature* 256: 495-499. In certain embodiments, a monoclonal antibody is produced using recombinant DNA methods (see, e.g., U.S. Pat. No. 4,816,567). In certain embodiments, a monoclonal antibody refers to an antibody fragment isolated from a phage display library. See, e.g., Clackson et al. (1991) *Nature* 352: 624-628, and Marks et al. (1991) *J. Mol. Biol.* 222: 581-597. For various other monoclonal antibody production techniques, see, e.g., Harlow and Lane (1988) *Antibodies: A Laboratory Manual* (Cold Spring Harbor Laboratory, Cold Spring Harbor, N.Y.).

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope. In certain instances, for example, homologous proteins from different species may comprise the same epitope. In certain embodiments, an antibody is said to specifically bind an antigen when the dissociation constant ($K_D$) is $\leq 1$ µM, in certain embodiments, when the dissociation constant is $\leq 100$ nM, and in certain embodiments, when the dissociation constant is $\leq 10$ nM.

The term "ANGPTL3" refers to an angiopoietin like protein 3 having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native ANGPTL3 that maintain at least one in vivo or in vitro activity of a native ANGPTL3. The term encompasses full-length unprocessed precursor forms of ANGPTL3 as well as mature forms resulting from post-translational cleavage of the signal peptide and forms resulting from proteolytic processing of the fibrinogen domain. In certain embodiments, a full-length, unprocessed mouse ANGPTL3 has the amino acid sequence set forth in SEQ ID NO: 1 (Genbank accession no. NP_038941). In certain embodiments, a full-length, unprocessed human ANGPTL3 has the amino acid sequence set forth in SEQ ID NO: 3 (Genbank accession no. NP_055310).

The term "Angptl3" refers to a nucleic acid encoding ANGPTL3.

The term "LPL" refers to a lipoprotein lipase having an amino acid sequence from any vertebrate or mammalian source, including, but not limited to, human, bovine, chicken, rodent, mouse, rat, porcine, ovine, primate, monkey, and guinea pig. In certain embodiments, a lipoprotein lipase catalyzes the hydrolysis of triacylglycerol in chylomicrons and very low density lipoproteins (VLDLs) into diacylglycerol and a free fatty acid anion. In certain embodiments, a lipoprotein lipase is also able to hydrolyze diacylglycerol.

The term "agent" refers to a chemical compound, a mixture of chemical compounds, a biological macromolecule, or an extract made from biological materials.

The term "antagonist of ANGPTL3" refers to an agent that reduces an activity of ANGPTL3.

The term "agonist of ANGPTL3" refers to an agent that increases an activity of ANGPTL3.

The term "patient" includes human and animal subjects. In certain embodiments, a patient is a mammal. In certain such embodiments, a patient is a human.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide.

A "conservative" amino acid substitution refers to the substitution of an amino acid in a polypeptide with another amino acid having similar properties, such as size or charge. In certain embodiments, a polypeptide comprising a conservative amino acid substitution maintains at least one activity of the unsubstituted polypeptide. A conservative amino acid substitution may encompass non-naturally occurring amino acid residues, which are typically incorporated by chemical peptide synthesis rather than by synthesis in biological systems. These include, but are not limited to, peptidomimetics and other reversed or inverted forms of amino acid moieties.

Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of a human antibody that are homologous with non-human antibodies, or into the non-homologous regions of the molecule.

In making substitutions, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein, in certain instances, is understood in the art. Kyte et al., *J. Mol. Biol.*, 157:105-131 (1982). It is known that in certain instances, certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residue | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

A skilled artisan will be able to determine suitable variants of a polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity or structure. In view of such a comparison, in certain embodiments, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In certain embodiments, in view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, in certain embodiments, based on information gathered from such routine experiments, one skilled in the art can readily determine the amino acids where further substitutions should be avoided either alone or in combination with other mutations.

A number of scientific publications have been devoted to the prediction of secondary structure. See, e.g., Moult J., *Curr. Opin. Biotechnol.* (1996) 7(4):422-427; Chou et al., (1974) *Biochemistry*, 13(2):222-245; Chou et al. (1974) *Biochemistry* 113(2):211-222; Chou et al. (1978); *Adv. Enzymol. Relat. Areas Mol. Biol.* 47:45-148; Chou et al. (1976) *Ann. Rev. Biochem.* 47:251-276; and Chou et al. (1979) *Biophys. J.* 26:367-384. Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The growth of the protein structural database (PDB) has provided enhanced predictability of secondary structure, including the potential number of folds within a polypeptide's structure. See, e.g., Holm et al. (1999) *Nucl. Acid. Res.* 27(1):244-247. It has been suggested (Brenner et al., (1997) *Curr. Op. Struct. Biol.* 7(3):369-376) that there are a limited number of folds in a given polypeptide or protein and that once a critical number of structures have been resolved, structural prediction will become dramatically more accurate.

Additional methods of predicting secondary structure include "threading" (see, e.g., Jones, D. (1997) *Curr. Opin. Struct. Biol.* 7(3):377-387; Sippl et al. (1996) *Structure* 4(1): 15-19), "profile analysis" (see, e.g., Bowie et al., (1991) *Science* 253:164-170; Gribskov et al., (1990) *Meth. Enzym.* 183: 146-159; Gribskov et al. (1987) *Proc. Nat. Acad. Sci. USA* 84(13):4355-4358), and "evolutionary linkage" (see, e.g., Holm et al. (1999) *Nucl. Acid. Res.* 27(1):244-247; and Brenner et al. (1997) *Curr. Op. Struct. Biol.* 7(3):369-376 (1997)).

In certain embodiments, a variant of a reference antibody includes a glycosylation variant wherein the number and/or type of glycosylation sites have been altered relative to the amino acid sequence of the reference antibody. In certain embodiments, a variant of a polypeptide comprises a greater or a lesser number of N-linked glycosylation sites relative to a native polypeptide. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. In certain embodiments, a rearrangement of N-linked carbohydrate chains is provided, wherein one or more N-linked glycosylation sites (typically those that are naturally occurring) are eliminated and one or more new N-linked sites are created. Exemplary antibody variants include cysteine variants wherein one or more cysteine residues are deleted from or substituted for another amino acid (e.g., serine) relative to the amino acid sequence of the reference antibody. In certain embodiments, cysteine variants may be useful when antibodies must be refolded into a biologically active conformation such as after the isolation of insoluble inclusion bodies. In certain embodiments, cysteine variants have fewer cysteine residues than the native polypeptide. In certain embodiments, cysteine variants have an even number of cysteine residues to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in a naturally-occurring sequence (in certain embodiments, in the portion of the polypeptide outside the domain(s) forming intermolecular contacts). In certain embodiments, a conservative amino acid substitution typically may not substantially change the structural characteristics of the reference sequence (e.g., in certain embodiments, a replacement amino acid should not tend to break a helix that occurs in the reference sequence, or disrupt other types of secondary structure that characterizes the reference sequence). Examples of certain art-recognized polypeptide secondary and tertiary structures are described, for example, in *Proteins, Structures and Molecular Principles* (Creighton, Ed., W. H. Freeman and Company, New York (1984)); Introduction to Protein Structure (C. Branden and J. Tooze, eds., Garland Publishing, New York, N.Y. (1991)); and Thornton, J. M. et al. (1991) *Nature* 354:105-106.

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) *FEMS Microbiol. Lett.* 174:247-250. The BLAST engine (version 2.2.10) is provided to the public by the National Center for Biotechnology Information (NCBI), Bethesda, Md. To align two polynucleotide sequences, the "Blast 2 Sequences" tool is used, which employs the "blastn" program with parameters set at default values as follows:

Matrix: not applicable
Reward for match: 1
Penalty for mismatch: −2
Open gap: 5 penalties
Extension gap: 2 penalties
Gap_x dropoff: 50
Expect: 10.0
Word size: 11
Filter: on "Percent identity" or "% identity," with reference to polypeptide sequences, refers to the percentage of identical amino acids between at least two polypeptide sequences aligned using the Basic Local Alignment Search Tool (BLAST) engine. See Tatusova et al. (1999) *FEMS Microbiol. Lett.* 174:247-250. The BLAST engine (version 2.2.10) is provided to the public by the National Center for Biotechnology Information (NCBI), Bethesda, Md. To align two polypeptide sequences, the "Blast 2 Sequences" tool is used, which employs the "blastp" program with parameters set at default values as follows:

Matrix: BLOSUM62
Open gap: 11 penalties
Extension gap: 1 penalty
Gap_x dropoff: 50
Expect: 10.0
Word size: 3
Filter: on The term "effective dose" or "effective amount" refers to an amount of an agent, e.g., a neutralizing antibody, that results in the reduction of symptoms in a patient or results in a desired biological outcome. In certain embodiments, an effective dose or effective amount is sufficient to reduce at least one activity of ANGPTL3. In certain embodiments, an effective dose or effective amount is determined as described below, Part V.G.

The term "treatment" encompasses both therapeutic and prophylactic/preventative measures unless otherwise indicated. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic agent" refers to an agent that may be administered in vivo to bring about a therapeutic and/or prophylactic/preventative effect.

A "therapeutic antibody" refers to an antibody that may be administered in vivo to bring about a therapeutic and/or prophylactic/preventative effect.

The terms "isolated nucleic acid" and "isolated polynucleotide" are used interchangeably. Exemplary isolated polynucleotides include, but are not limited to, genomic DNA, RNA, cDNA, synthetic DNA or RNA or some combination thereof. An "isolated polynucleotide" (1) is not associated with all or a portion of a polynucleotide in which the "isolated polynucleotide" is found in nature, (2) is linked to a polynucleotide to which it is not linked in nature, or (3) does not occur in nature as part of a larger sequence.

B. Structure of native antibodies and certain antibody fragments

A native antibody typically has a tetrameric structure. A tetramer typically comprises two identical pairs of polypeptide chains, each pair having one light chain (in certain embodiments, about 25 kDa) and one heavy chain (in certain embodiments, about 50-70 kDa). In a native antibody, a heavy chain comprises a variable region, $V_H$, and three constant regions, $C_H1$, $C_H2$, and $C_H3$. The $V_H$ domain is at the amino-terminus of the heavy chain, and the $C_H3$ domain is at the carboxy-terminus. In a native antibody, a light chain comprises a variable region, $V_L$, and a constant region, $C_L$. The variable region of the light chain is at the amino-terminus of the light chain. In a native antibody, the variable regions of each light/heavy chain pair typically form the antigen binding site. The constant regions are typically responsible for effector function.

Native human light chains are typically classified as kappa and lambda light chains. Native human heavy chains are typically classified as mu, delta, gamma, alpha, or epsilon, and define the antibody's isotype as IgM, IgD, IgG, IgA, and IgE, respectively. IgG has subclasses, including, but not limited to, IgG1, IgG2, IgG3, and IgG4. IgM has subclasses including, but not limited to, IgM1 and IgM2. IgA has subclasses including, but not limited to, IgA1 and IgA2. Within native human light and heavy chains, the variable and constant regions are typically joined by a "J" region of about 12 or more amino acids, with the heavy chain also including a "D" region of about 10 more amino acids. See, e.g., *Fundamental Immunology* (1989) Ch. 7 (Paul, W., ed., 2nd ed. Raven Press, N.Y.).

In a native antibody, the variable regions typically exhibit the same general structure in which relatively conserved framework regions (FRs) are joined by three hypervariable regions, also called complementarity determining regions (CDRs). The CDRs from the two chains of each pair typically are aligned by the framework regions, which may enable binding to a specific epitope. From N-terminus to C-terminus, both light and heavy chain variable regions typically comprise the domains FR1, CDR1, FR2, CDR2, FR3, CDR3 and FR4. The CDRs on the heavy chain are referred to as H1, H2, and H3, while the CDRs on the light chain are referred to as L1, L2, and L3. Typically, CDR3 is the greatest source of molecular diversity within the antigen-binding site. H3, for example, in certain instances, can be as short as two amino acid residues or greater than 26. The assignment of amino acids to each domain is typically in accordance with the definitions of Kabat et al. (1991) *Sequences of Proteins of Immunological Interest* (National Institutes of Health, Publication No. 91-3242, vols. 1-3, Bethesda, Md.); Chothia, C., and Lesk, A. M. (1987) *J. Mol. Biol.* 196:901-917; or Chothia, C. et al. *Nature* 342:878-883 (1989). In the present application, the term "CDR" refers to a CDR from either the light or heavy chain, unless otherwise specified.

A "Fab" fragment comprises one light chain and the $C_H1$ and variable region of one heavy chain. The heavy chain of a Fab molecule cannot form a disulfide bond with another heavy chain molecule. A "Fab'" fragment comprises one light chain and one heavy chain that comprises additional constant region, extending between the $C_H1$ and $C_H2$ domains. An interchain disulfide bond can be formed between two heavy chains of a Fab' fragment to form a "F(ab')$_2$" molecule.

An "Fv" fragment comprises the variable regions from both the heavy and light chains, but lacks the constant regions. A single-chain Fv (scFv) fragment comprises heavy and light chain variable regions connected by a flexible linker to form a single polypeptide chain with an antigen-binding region. Exemplary single chain antibodies are discussed in detail in WO 88/01649 and U.S. Pat. Nos. 4,946,778 and 5,260,203. In certain instances, a single variable region (i.e., a heavy chain variable region or a light chain variable region) may have the ability to recognize and bind antigen.

As used herein, the term "heavy chain" refers to a polypeptide comprising sufficient heavy chain variable region sequence to confer antigen specificity either alone or in combination with a light chain.

As used herein, the term "light chain" refers to a polypeptide comprising sufficient light chain variable region sequence to confer antigen specificity either alone or in combination with a heavy chain.

C. Certain antibodies

In certain embodiments, monoclonal antibodies that specifically bind to ANGPTL3 are provided. In certain such embodiments, the monoclonal antibodies are neutralizing monoclonal antibodies that reduce at least one activity of ANGPTL3 in vivo and/or in vitro.

In certain embodiments, a neutralizing monoclonal antibody against ANGPTL3 reduces at least one serum lipid level in vivo. In certain embodiments, a neutralizing monoclonal antibody against ANGPTL3 reduces serum triglyceride levels in vivo. In certain embodiments, a neutralizing monoclonal antibody reduces total cholesterol levels in vivo. In certain embodiments, a neutralizing monoclonal antibody against ANGPTL3 reduces free fatty acid (FFA) levels in vivo. In certain embodiments, a neutralizing monoclonal antibody against ANGPTL3 reduces at least two of those levels in vivo. In certain embodiments, a neutralizing monoclonal antibody against ANGPTL3 reduces at least three of those levels in vivo.

In certain embodiments, a neutralizing monoclonal antibody against ANGPTL3 reduces serum triglycerides in LDLr knockout mice in vivo. In certain embodiments, a neutralizing monoclonal antibody against ANGPTL3 reduces total cholesterol in LDLr knockout mice in vivo. In certain embodiments, a neutralizing monoclonal antibody against ANGPTL3 reduces serum triglycerides in ApoE knockout mice in vivo. In certain embodiments, a neutralizing monoclonal antibody against ANGPTL3 reduces total cholesterol in ApoE knockout mice in vivo. In certain embodiments, a neutralizing monoclonal antibody against ANGPTL3 reduces serum triglycerides in db/db mice in vivo. In certain embodiments, a neutralizing monoclonal antibody against ANGPTL3 reduces total cholesterol in db/db mice in vivo.

In certain embodiments, neutralizing monoclonal antibodies that specifically bind to mouse ANGPTL3 are provided. In certain embodiments, neutralizing monoclonal antibodies that specifically bind to human ANGPTL3 are provided. In certain embodiments, neutralizing monoclonal antibodies that specifically bind to the same epitope in ANGPTL3 from different species (i.e., antibodies that demonstrate cross-reactivity) are provided. In certain such embodiments, the antibodies specifically bind to both mouse ANGPTL3 and human ANGPTL3.

In certain embodiments, neutralizing monoclonal antibodies that specifically bind to an epitope within the N-terminal coiled-coil domain of ANGPTL3 are provided. In certain embodiments, neutralizing monoclonal antibodies that specifically bind to an epitope within the N-terminal coiled-coil domain of mouse ANGPTL3 are provided. In certain embodiments, neutralizing monoclonal antibodies specifically bind to an epitope within a region of mouse ANGPTL3 from residue 17 to residue 240 of SEQ ID NO: 1 (SEQ ID NO: 59). In certain embodiments, neutralizing monoclonal antibodies specifically bind to the SP1 region of mouse ANGPTL3 from residue 32 to residue 57 of SEQ ID NO: 1 (SEQ ID NO: 9). In certain embodiments, neutralizing monoclonal antibodies specifically bind to an epitope within the SP1 region of mouse ANGPTL3 that includes amino acids 34 to 37 and 40 of SEQ ID NO: 1 (amino acids 3 to 6 and 9 of SEQ ID NO: 9). In certain embodiments, neutralizing monoclonal antibodies specifically bind to an epitope within the SP1 region of mouse ANGPTL3 that includes amino acids 33 to 37 and 40 of SEQ ID NO: 1 (amino acids 2 to 6 and 9 of SEQ ID NO: 9). In certain embodiments, neutralizing monoclonal antibodies specifically bind to an epitope within the SP1 region of mouse ANGPTL3 that includes amino acids 34 to 37, 40, and 42 of SEQ ID NO: 1 (amino acids 3 to 6, 9, and 11 of SEQ ID NO: 9). In certain embodiments, neutralizing monoclonal antibodies specifically bind to an epitope within the SP1 region of mouse ANGPTL3 that includes amino acids 34 to 37 and 40 to 42 of SEQ ID NO: 1 (amino acids 3 to 6 and 9 to 11 of SEQ ID NO: 9).

In certain embodiments, neutralizing monoclonal antibodies that specifically bind to an epitope within the N-terminal coiled-coil domain of human ANGPTL3 are provided. In certain embodiments, neutralizing monoclonal antibodies specifically bind to an epitope within a region of human ANGPTL3 from residue 20 to residue 143 of SEQ ID NO: 3 (SEQ ID NO: 60). In certain embodiments, neutralizing monoclonal antibodies specifically bind to the SP1 region of human ANGPTL3 from residue 32 to residue 57 of SEQ ID NO: 3 (SEQ ID NO: 10). In certain embodiments, neutralizing monoclonal antibodies specifically bind to an epitope within the SP1 region of mouse ANGPTL3 that includes amino acids 34 to 37 and 40 of SEQ ID NO: 3 (amino acids 3 to 6 and 9 of SEQ ID NO: 10). In certain embodiments, neutralizing monoclonal antibodies specifically bind to an epitope within the SP1 region of mouse ANGPTL3 that includes amino acids 33 to 37 and 40 of SEQ ID NO: 3 (amino acids 2 to 6 and 9 of SEQ ID NO: 10). In certain embodiments, neutralizing monoclonal antibodies specifically bind to an epitope within the SP1 region of mouse ANGPTL3 that includes amino acids 34 to 37, 40, and 42 of SEQ ID NO: 3 (amino acids 3 to 6, 9, and 11 of SEQ ID NO: 10). In certain embodiments, neutralizing monoclonal antibodies specifically bind to an epitope within the SP1 region of mouse ANGPTL3 that includes amino acids 34 to 37 and 40 to 42 of SEQ ID NO: 3 (amino acids 3 to 6 and 9 to 11 of SEQ ID NO: 10).

In various embodiments, a neutralizing monoclonal antibody binds to a peptide having an amino acid sequence of SEQ ID NO: 9 with at least 2-fold, at least 3-fold, at least 4-fold, at least 5-fold, at least 7-fold, or at least 10-fold greater affinity than the neutralizing monoclonal antibody binds to a peptide having an amino acid sequence of any one of SEQ ID NO: 84, SEQ ID NO: 85, SEQ ID NO: 86, SEQ ID NO: 87, SEQ ID NO: 88, SEQ ID NO: 90, and SEQ ID NO: 92. In various embodiments, a neutralizing monoclonal antibody binds to a peptide having an amino acid sequence of SEQ ID NO: 9 with at least 2-fold, at least 3-fold, at least 4-fold, at least 5-fold, at least 7-fold, or at least 10-fold greater affinity than the neutralizing monoclonal antibody binds to each of SEQ ID NO: 84, SEQ ID NO: 85, SEQ ID NO: 86, SEQ ID NO: 87, SEQ ID NO: 88, SEQ ID NO: 90, and SEQ ID NO: 92. In certain embodiments, affinity is determined as described in Example H(2).

In certain embodiments, neutralizing monoclonal antibodies are non-human monoclonal antibodies. In certain such embodiments, neutralizing monoclonal antibodies are rodent monoclonal antibodies. In certain such embodiments, neutralizing monoclonal antibodies are mouse monoclonal antibodies. In certain embodiments, neutralizing monoclonal antibodies are chimeric monoclonal antibodies. In certain embodiments, neutralizing monoclonal antibodies are humanized monoclonal antibodies. In certain embodiments, neutralizing monoclonal antibodies are human monoclonal antibodies. In certain embodiments, chimeric, humanized, and/or human monoclonal antibodies are useful as therapeutic antibodies in humans.

In certain embodiments, neutralizing monoclonal antibodies are antibody fragments. Exemplary antibody fragments include, but are not limited to, Fab, Fab', F(ab')$_2$, Fv, scFv, Fd, diabodies, and other antibody fragments.

In various embodiments, a neutralizing monoclonal antibody binds to human ANGPTL3 with a $K_D$ of less than 1 µM, less than 500 nM, less than 300 nM, less than 200 nM, less than 100 nM, less than 75 nM, less than 50 nM, less than 30 nM, less than 25 nM, less than 20 nM, less than 15 nM, less than 10 nM, less than 5 nM, less than 4 nM, less than 3 nM, or less than 2 nM. In various embodiments, a neutralizing monoclonal antibody binds to a human SP1 peptide with a $K_D$ of less than 1 µM, less than 500 nM, less than 300 nM, less than 200 nM, less than 100 nM, less than 75 nM, less than 50 nM, less than 30 nM, less than 25 nM, less than 20 nM, less than 15 nM, less than 10 nM, less than 5 nM, less than 4 nM, less than 3 nM, or less than 2 nM. In various embodiments, a neutralizing monoclonal antibody binds to a peptide having an amino acid sequence of SEQ ID NO: 9 with a $K_D$ of less than 1 µM, less than 500 nM, less than 300 nM, less than 200 nM, less than 100 nM, less than 75 nM, less than 50 nM, less than 30 nM, less than 25 nM, less than 20 nM, less than 15 nM, less than 10 nM, less than 5 nM, less than 4 nM, less than 3 nM, or less than 2 nM. In various embodiments, a neutralizing monoclonal antibody binds to a peptide having an amino acid sequence of SEQ ID NO: 10 with a $K_D$ of less than 1 µM, less than 500 nM, less than 300 nM, less than 200 nM, less than 100 nM, less than 75 nM, less than 50 nM, less than 30 nM, less than 25 nM, less than 20 nM, less than 15 nM, less than 10 nM, less than 5 nM, less than 4 nM, less than 3 nM, or less than 2 nM.

In various embodiments, a neutralizing monoclonal antibody against ANGPTL3 binds to mouse ANGPTL3 (SEQ ID NO: 1) with at least 10-fold greater affinity, at least 15-fold greater affinity, at least 20-fold greater affinity, at least 25-fold greater affinity, at least 30-fold greater affinity, at least 40-fold greater affinity, at least 50-fold greater affinity, at least 100-fold greater affinity, or at least 200-fold greater affinity than it binds to mouse ANGPTL4 (SEQ ID NO: 107). In various embodiments, a neutralizing monoclonal antibody against ANGPTL3 binds to human ANGPTL3 (SEQ ID NO: 3) with at least 10-fold greater affinity, at least 15-fold greater affinity, at least 20-fold greater affinity, at least 25-fold greater affinity, at least 30-fold greater affinity, at least 40-fold greater affinity, at least 50-fold greater affinity, at least 100-fold greater affinity, or at least 200-fold greater affinity than it binds to human ANGPTL4 (SEQ ID NO: 108). In various embodiments, a neutralizing monoclonal antibody against ANGPTL3 binds to a peptide having the amino acid sequence of the mouse ANGPTL3 SP1 region (SEQ ID NO: 9) with at least 10-fold greater affinity, at least 15-fold greater affinity, at least 20-fold greater affinity, at least 25-fold greater affinity, at least 30-fold greater affinity, at least 40-fold greater affinity, at least 50-fold greater affinity, at least 100-fold greater affinity, or at least 200-fold greater affinity than it binds to a peptide having the amino acid sequence of the mouse ANGPTL4 SP1 region (SEQ ID NO: 109). In various embodiments, a neutralizing monoclonal antibody against ANGPTL3 binds to a peptide having the amino acid sequence of the human ANGPTL3 SP1 region (SEQ ID NO: 10) with at least 10-fold greater affinity, at least 15-fold greater affinity, at least 20-fold greater affinity, at least 25-fold greater affinity, at least 30-fold greater affinity, at least 40-fold greater affinity, at least 50-fold greater affinity, at least 100-fold greater affinity, or at least 200-fold greater affinity than it binds to a peptide having the amino acid sequence of the human ANGPTL4 SP1 region (SEQ ID NO: 110).

Exemplary neutralizing monoclonal antibodies, designated 4.7.1, 4.8.3, 4.9.1, 1.315.1, 5.35, and 5.50 are provided. Antibodies 4.7.1, 4.8.3, 4.9.1, 5.35, and 5.50 bind to an epitope within residues 32 to 57 of mouse ANGPTL3 or human ANGPTL3 (SEQ ID NOs: 9 and 10). In certain embodiments, antibodies 4.7.1 and 4.9.1 bind to an epitope within the SP1 region of mouse ANGPTL3 or human ANGPTL3 that includes amino acids 33 to 37 and 40 of SEQ ID NO: 2 or SEQ ID NO: 3 (amino acids 2 to 6 and 9 of SEQ ID NO: 9 or SEQ ID NO: 10). In certain embodiments, antibodies 5.35 and 5.50 bind to an epitope within the SP1 region of mouse ANGPTL3 or human ANGPTL3 that includes amino acids 34 to 37 and 40 to 42 of SEQ ID NO: 2 or SEQ ID NO: 3 (amino acids 3 to 6 and 9 to 11 of SEQ ID NO: 9 or SEQ ID NO: 10). In certain embodiments, antibody 4.8.3 binds to an epitope within the SP1 region of mouse ANGPTL3 or human ANGPTL3 that includes amino acids 34 to 37, 40, and 42 of SEQ ID NO: 2 or SEQ ID NO: 3 (amino acids 3 to 6, 9, and 11 of SEQ ID NO: 9 or SEQ ID NO: 10). Antibody 1.315.1 binds to an epitope within residues 42 to 116 of mouse ANGPTL3 (SEQ ID NO: 61).

Antibodies 4.7.1, 4.8.3, 4.9.1, 1.315.1, 5.35, and 5.50 neutralize at least one ANGPTL3 activity. Thus, antibodies that bind an epitope bound by at least one of antibodies 4.7.1, 4.8.3, 4.9.1, 1.315.1, 5.35, and 5.50 (e.g., in either human or mouse ANGPTL3) would be expected to also possess neutralizing activity. Certain neutralizing monoclonal antibodies against ANGPTL3 bind to one or more peptides chosen from SEQ ID NOs: 9, 10, 12, 13, and 61. Certain neutralizing monoclonal antibodies against ANGPTL3 bind to one or more peptides chosen from SEQ ID NOs: 9 and 10. In certain embodiments, a neutralizing monoclonal antibody against ANGPTL3 binds to a peptide having the sequence of SEQ ID NO: 61. In certain embodiments, a neutralizing monoclonal antibody against ANGPTL3 binds to a peptide having the sequence of SEQ ID NO: 12 and a peptide having the sequence of SEQ ID NO: 13.

In certain embodiments, neutralizing monoclonal antibodies are provided that bind to the same epitope to which monoclonal antibody 4.7.1 binds. In certain embodiments, neutralizing monoclonal antibodies are provided that bind to the same epitope to which monoclonal antibody 4.8.3 binds. In certain embodiments, neutralizing monoclonal antibodies are provided that bind to the same epitope to which monoclonal antibody 4.9.1 binds. In certain embodiments, neutralizing monoclonal antibodies are provided that bind to the same epitope to which monoclonal antibody 5.35 binds. In certain embodiments, neutralizing monoclonal antibodies are provided that bind to the same epitope to which monoclonal antibody 5.50 binds. In certain embodiments, neutralizing monoclonal antibodies are provided that bind to the same epitope to which monoclonal antibody 1.315.1 binds.

Certain neutralizing antibodies comprise a heavy chain comprising an amino acid sequence as set forth in SEQ ID NO: 20. Certain neutralizing antibodies comprise a heavy chain comprising an amino acid sequence as set forth in SEQ ID NO: 22. Certain neutralizing antibodies comprise a heavy chain comprising an amino acid sequence as set forth in SEQ ID NO: 24. Certain neutralizing antibodies comprise a light chain comprising an amino acid sequence as set forth in SEQ ID NO: 28. Certain neutralizing antibodies comprise a light chain comprising an amino acid sequence as set forth in SEQ ID NO: 30. Certain neutralizing antibodies comprise a light chain comprising an amino acid sequence as set forth in SEQ ID NO: 32.

Certain neutralizing antibodies comprise a heavy chain comprising an amino acid sequence as set forth in SEQ ID NO: 20 and a light chain comprising an amino acid sequence as set forth in SEQ ID NO: 28. Certain neutralizing antibodies comprise a heavy chain comprising an amino acid sequence as set forth in SEQ ID NO: 22 and a light chain comprising an amino acid sequence as set forth in SEQ ID NO: 30. Certain neutralizing antibodies comprise a heavy chain comprising an amino acid sequence as set forth in SEQ ID NO: 24 and a light chain comprising an amino acid sequence as set forth in SEQ ID NO: 32.

1. Chimerized and humanized monoclonal antibodies

In certain embodiments, non-human antibodies are chimerized. In certain embodiments, mouse monoclonal antibodies that specifically bind human ANGPTL3 are chimerized. Certain exemplary methods for making chimeric antibodies are provided, for example, in Morrison et al. (1984) *Proc. Nat'l Acad. Sci. USA* 81:6851-6855; Neuberger et al. (1984) *Nature* 312:604-608; Takeda et al. (1985) *Nature* 314:452-454; and U.S. Pat. Nos. 6,075,181 and 5,877,397.

In certain embodiments, non-human antibodies are "humanized." In certain embodiments, mouse monoclonal antibodies that specifically bind human ANGPTL3 are humanized. In certain embodiments, mouse monoclonal antibodies raised against mouse ANGPTL3, but which specifically bind (i.e., cross react) with human ANGPTL3, are humanized. In certain embodiments, humanized antibodies retain their binding specificity and have reduced immunogenicity (e.g., reduced human anti-mouse antibody (HAMA) response) when administered to a human. In certain embodiments, humanization is achieved by methods including, but not limited to, CDR grafting and human engineering, as described in detail below.

In certain embodiments of humanized antibodies, one or more complementarity determining regions (CDRs) from the light and heavy chain variable regions of an antibody with the desired binding specificity (the "donor" antibody) are grafted onto human framework regions (FRs) in an "acceptor" antibody. Exemplary CDR grafting is described, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In certain embodiments, one or more CDRs from the light and heavy chain variable regions are grafted onto consensus human FRs in an acceptor antibody. To create consensus human FRs, in certain embodiments, FRs from several human heavy chain or light chain amino acid sequences are aligned to identify a consensus amino acid sequence.

In certain embodiments, certain FR amino acids in the acceptor antibody are replaced with FR amino acids from the donor antibody. In certain such embodiments, FR amino acids from the donor antibody are amino acids that contribute to the affinity of the donor antibody for the target antigen. See, e.g., in U.S. Pat. Nos. 6,180,370, 5,693,762, 5,693,761, 5,585,089, and 5,530,101; Queen et al. (1989) *Proc. Nat'l Acad. Sci. USA* 86:10029-10033. In certain embodiments, computer programs are used for modeling donor and/or acceptor antibodies to identify residues that are likely to be involved in binding antigen and/or to contribute to the structure of the antigen binding site, thus assisting in the selection of residues, such as FR residues, to be replaced in the donor antibody.

In certain embodiments, CDRs from a donor antibody are grafted onto an acceptor antibody comprising a human constant region. In certain such embodiments, FRs are also grafted onto the acceptor. In certain embodiments, CDRs from a donor antibody are derived from a single chain Fv antibody. In certain embodiments, FRs from a donor antibody are derived from a single chain Fv antibody. In certain embodiments, grafted CDRs in a humanized antibody are further modified (e.g., by amino acid substitutions, deletions, or insertions) to increase the affinity of the humanized antibody for the target antigen. In certain embodiments, grafted FRs in a humanized antibody are further modified (e.g., by amino acid substitutions, deletions, or insertions) to increase the affinity of the humanized antibody for the target antigen.

In certain embodiments, non-human antibodies may be humanized using a "human engineering" method. See, e.g., U.S. Pat. Nos. 5,766,886 and 5,869,619. In certain embodiments of human engineering, information on the structure of antibody variable domains (e.g., information obtained from crystal structures and/or molecular modeling) is used to assess the likelihood that a given amino acid residue in a variable region is (a) involved in antigen binding, (b) exposed on the antibody surface (i.e., accessible to solvent), or (c) buried within the antibody variable region (i.e., involved in maintaining the structure of the variable region). Furthermore, in certain embodiments, human variable region consensus sequences are generated to identify residues that are conserved among human variable regions. In certain embodiments, that information provides guidance as to whether an amino acid residue in the variable region of a non-human antibody should be substituted.

Certain neutralizing antibodies comprise a heavy chain comprising CDR1, CDR2, and CDR3 of 4.7.1. Certain neutralizing antibodies comprise a heavy chain comprising CDR1, CDR2, and CDR3 of 4.8.3. Certain neutralizing antibodies comprise a heavy chain comprising CDR1, CDR2, and CDR3 of 4.9.1. Certain neutralizing antibodies comprise a heavy chain comprising CDR1, CDR2, and CDR3 of 5.35. Certain neutralizing antibodies comprise a heavy chain comprising CDR1, CDR2, and CDR3 of 5.50. Certain neutralizing antibodies comprise a heavy chain comprising CDR1, CDR2, and CDR3 of 1.315.1. Certain neutralizing antibodies comprise a heavy chain comprising at least one CDR of 4.7.1. Certain neutralizing antibodies comprise a heavy chain comprising at least one CDR of 4.8.3. Certain neutralizing antibodies comprise a heavy chain comprising at least one CDR of 4.9.1. Certain neutralizing antibodies comprise a heavy chain comprising at least one CDR of 5.35. Certain neutralizing antibodies comprise a heavy chain comprising at least one CDR of 5.50. Certain neutralizing antibodies comprise a heavy chain comprising at least one CDR of 1.315.1. Certain neutralizing antibodies comprise a heavy chain comprising at least two CDRs of 4.7.1. Certain neutralizing antibodies comprise a heavy chain comprising at least two CDRs of 4.8.3. Certain neutralizing antibodies comprise a heavy chain comprising at least two CDRs of 4.9.1. Certain neutralizing antibodies comprise a heavy chain comprising at least two CDRs of 5.35. Certain neutralizing antibodies comprise a heavy chain comprising at least two CDRs of 5.50. Certain neutralizing antibodies comprise a heavy chain comprising at least two CDRs of 1.315.1.

Certain neutralizing antibodies comprise a light chain comprising CDR1, CDR2, and CDR3 of 4.7.1. Certain neutralizing antibodies comprise a light chain comprising CDR1, CDR2, and CDR3 of 4.8.3. Certain neutralizing antibodies comprise a light chain comprising CDR1, CDR2, and CDR3 of 4.9.1. Certain neutralizing antibodies comprise a light chain comprising CDR1, CDR2, and CDR3 of 5.35. Certain neutralizing antibodies comprise a light chain comprising CDR1, CDR2, and CDR3 of 5.50. Certain neutralizing antibodies comprise a light chain comprising CDR1, CDR2, and CDR3 of 1.315.1. Certain neutralizing antibodies comprise a light chain comprising at least one CDR of 4.7.1. Certain neutralizing antibodies comprise a light chain comprising at least one CDR of 4.8.3. Certain neutralizing antibodies comprise a light chain comprising at least one CDR of 4.9.1. Certain neutralizing antibodies comprise a light chain comprising at least one CDR of 5.35. Certain neutralizing antibodies comprise a light chain comprising at least one CDR of 5.50. Certain neutralizing antibodies comprise a light chain comprising at least one CDR of 1.315.1. Certain neutralizing antibodies comprise a light chain comprising at least two CDRs of 4.7.1. Certain neutralizing antibodies comprise a light chain comprising at least two CDRs of 4.8.3. Certain neutralizing antibodies comprise a light chain comprising at least two CDRs of 4.9.1. Certain neutralizing antibodies comprise a light chain comprising at least two CDRs of 5.35. Certain neutralizing antibodies comprise a light chain comprising at least two CDRs of 5.50. Certain neutralizing antibodies comprise a light chain comprising at least two CDRs of 1.315.1.

2. Antibody isotypes

In certain embodiments, an antibody against ANGPTL3 is of any isotype selected from IgM, IgD, IgG, IgA, and IgE. In certain embodiments, an antibody against ANGPTL3 is of the IgG isotype. In certain such embodiments, an antibody is of the subclass IgG1, IgG2, IgG3, or IgG4. In certain embodiments, an antibody against ANGPTL3 is of the IgM isotype. In certain such embodiments, an antibody is of the subclass IgM1 or IgM2. In certain embodiments, an antibody against ANGPTL3 is of the IgA isotype. In certain such embodiments, an antibody is of the subclass IgA1 or IgA2. In certain embodiments, an antibody against ANGPTL3 comprises a human kappa light chain and a human IgG1 or IgG2 heavy chain. In certain embodiments, an antibody against ANGPTL3 comprises a mouse kappa light chain and a mouse IgG1 or IgG2 heavy chain.

3. Modified antibodies

In various embodiments, an antibody is modified to alter one or more of its properties. In certain embodiments, a modified antibody may possess advantages over an unmodified antibody, such as increased stability, increased time in circulation, or decreased immunogenicity (see, e.g., U.S. Pat. No. 4,179,337). In certain embodiments, an antibody is modified by linking it to a nonproteinaceous moiety. In certain embodiments, an antibody is modified by altering the glycosylation state of the antibody, e.g., by altering the number, type, linkage, and/or position of carbohydrate chains on the antibody. In certain embodiments, an antibody is altered so that it is not glycosylated.

In certain embodiments, one or more chemical moieties are linked to the amino acid backbone and/or carbohydrate residues of the antibody. Certain exemplary methods for linking a chemical moiety to an antibody are known to those skilled in the art. Such methods include, but are not limited to, acylation reactions or alkylation reactions. See, e.g., EP 0 401 384; Malik et al. (1992), *Exp. Hematol.*, 20:1028-1035; Francis (1992) *Focus on Growth Factors* 3(2):4-10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459. In certain embodiments, any of these reactions are used to generate an antibody that is chemically modified at its amino-terminus.

In certain embodiments, an antibody is linked to a detectable label, such as an enzymatic, fluorescent, isotopic or affinity label. In certain such embodiments, a detectable label allows for the detection or isolation of the antibody. In certain embodiments, a detectable label allows for the detection of an antigen bound by the antibody.

In certain embodiments, an antibody is modified by linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

Certain exemplary clinically acceptable, water-soluble polymers include, but are not limited to, polyethylene glycol (PEG); polyethylene glycol propionaldehyde; copolymers of ethylene glycol/propylene glycol; monomethoxy-polyethylene glycol; carboxymethylcellulose; dextran; polyvinyl alcohol (PVA); polyvinyl pyrrolidone, poly-1,3-dioxolane; poly-1,3,6-trioxane; ethylene/maleic anhydride copolymer; poly-β-amino acids (either homopolymers or random copolymers); poly(n-vinyl pyrrolidone)polyethylene glycol; polypropylene glycol homopolymers (PPG) and other polyalkylene oxides; polypropylene oxide/ethylene oxide copolymers; polyoxyethylated polyols (POG) (e.g., glycerol) and other polyoxyethylated polyols; polyoxyethylated sorbitol, polyoxyethylated glucose, colonic acids or other carbohydrate polymers; and Ficoll, dextran, or mixtures thereof. Certain exemplary PEGs include, but are not limited to, certain forms known in the art to be useful in antibody modification, such as mono-$(C_1-C_{10})$ alkoxy- or aryloxy-PEG. In certain embodiments, PEG propionaldehyde may have advantages in manufacturing due to its stability in water.

In certain embodiments, a water-soluble polymer is of any molecular weight. In certain embodiments, a water-soluble polymer is branched or unbranched. In certain embodiments, a water-soluble polymer has an average molecular weight of about 2 kDa to about 100 kDa, including all points between the end points of the range. In certain embodiments, a water-soluble polymer has an average molecular weight of about 5 kDa to about 40 kDa. In certain embodiments, a water-soluble polymer has an average molecular weight of about 10 kDa to about 35 kDa. In certain embodiments, a water-soluble polymer has an average molecular weight of about 15 kDa to about 30 kDa.

In certain embodiments, an antibody is linked to PEG (i.e., an antibody is "pegylated"). In various embodiments, PEG has low toxicity in mammals. See Carpenter et al. (1971) *Toxicol. Appl. Pharmacol.*, 18:35-40. Notably, a PEG adduct of adenosine deaminase was approved in the United States for use in humans for the treatment of severe combined immunodeficiency syndrome. In various embodiments, PEG may reduce the immunogenicity of antibodies. For example, in certain embodiments, linkage of PEG to an antibody having non-human sequences may reduce the antigenicity of that antibody when administered to a human.

In certain embodiments, a polymer is linked to one or more reactive amino acid residues in an antibody. Certain exemplary reactive amino acid residues include, but are not limited to, the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, and activated glycosyl chains linked to certain asparagine, serine or threonine residues. Certain exemplary activated forms of PEG ("PEG reagents") suitable for direct reaction with proteins are known to those skilled in the art. For example, in certain embodiments, PEG reagents suitable for linkage to amino groups include, but are not limited to, active esters of carboxylic acid or carbonate derivatives of PEG, for example, those in which the leaving groups are N-hydroxysuccinimide, p-nitrophenol, imidazole or 1-hydroxy-2-nitrobenzene-4-sulfonate. In certain embodiments, PEG reagents containing maleimido or haloacetyl groups are used to modify sulfhydryl groups. In certain embodiments, PEG reagents containing amino, hydrazine and/or hydrazide groups may be used in reactions with aldehydes generated by periodate oxidation of carbohydrate groups in proteins.

In certain embodiments, a water-soluble polymer has at least one reactive group. In certain embodiments, an activated derivative of a water-soluble polymer, such as PEG, is created by reacting the water-soluble polymer with an activating group. In certain embodiments, an activating group may be monofunctional, bifunctional, or multifunctional. Certain exemplary activating groups that can be used to link a water-soluble polymer to two or more antibodies include, but are not limited to, the following groups: sulfone (e.g., chlorosulfone, vinylsulfone and divinylsulfone), maleimide, sulfhydryl, thiol, triflate, tresylate, azidirine, oxirane and 5-pyridyl. In certain embodiments, a PEG derivative is typically stable against hydrolysis for extended periods in aqueous environments at pHs of about 11 or less. In certain embodiments, a PEG derivative linked to another molecule, such as an antibody, confers stability from hydrolysis on that molecule. Certain exemplary homobifunctional PEG derivatives include, but are not limited to, PEG-bis-chlorosulfone and PEG-bis-vinylsulfone (see WO 95/13312).

D. Certain methods of making monoclonal antibodies

1. Certain hybridoma methods

In certain embodiments, monoclonal antibodies are produced by standard techniques. In certain embodiments, monoclonal antibodies are produced by hybridoma-based methods. Certain such methods are known to those skilled in the art. See, e.g., Kohler et al. (1975) *Nature* 256:495-497; Harlow and Lane (1988) *Antibodies: A Laboratory Manual* Ch. 6 (Cold Spring Harbor Laboratory, Cold Spring Harbor, N.Y.). In certain such embodiments, a suitable animal, such as a mouse, rat, hamster, monkey, or other mammal, is immunized with an immunogen to produce antibody-secreting cells. In certain embodiments, the antibody-secreting cells are B-cells, such as lymphocytes or splenocytes. In certain embodiments, lymphocytes (e.g., human lymphocytes) are immunized in vitro to generate antibody-secreting cells. See, e.g., Borreback et al. (1988) *Proc. Nat'l Acad. Sci. USA* 85:3995-3999.

In certain embodiments, antibody secreting cells are fused with an "immortalized" cell line, such as a myeloid-type cell line, to produce hybridoma cells. In certain embodiments, hybridoma cells that produce the desired antibodies are identified, for example, by ELISA. In certain embodiments, such cells can then be subcloned and cultured using standard methods. In certain embodiments, such cells can also be grown in vivo as ascites tumors in a suitable animal host. In certain embodiments, monoclonal antibodies are isolated from hybridoma culture medium, serum, or ascites fluid using standard separation procedures, such as affinity chromatography. Guidance for the production of hybridomas and the purification of monoclonal antibodies according to certain embodiments is provided, for example, in Harlow and Lane (1988) *Antibodies: A Laboratory Manual* Ch. 8 (Cold Spring Harbor Laboratory, Cold Spring Harbor, N.Y.).

In certain embodiments, mouse monoclonal antibodies are produced by immunizing genetically altered mice with an immunogen. In certain such embodiments, the mice are ANGPTL3-deficient mice, which partially or completely lack ANGPTL3 function. In certain such embodiments, the mice are "knockout" mice that lack all or part of a gene encoding ANGPTL3. In certain embodiments, such knockout mice are immunized with mouse ANGPTL3. In certain embodiments, such knockout mice are immunized with human ANGPTL3.

In certain embodiments, human monoclonal antibodies are raised in transgenic animals (e.g., mice) that are capable of producing human antibodies. See, e.g., U.S. Pat. Nos. 6,075, 181 A and 6,114,598 A; and WO 98/24893 A2. For example, in certain embodiments, human immunoglobulin genes are introduced (e.g., using yeast artificial chromosomes, human chromosome fragments, or germline integration) into mice in which the endogenous Ig genes have been inactivated. See, e.g., Jakobovits et al. (1993) *Nature* 362:255-258; Tomizuka et al. (2000) *Proc. Nat'l Acad. Sci. USA* 97:722-727; and Mendez et al. (1997) *Nat. Genet.* 15:146-156 (describing the XenoMouse II® line of transgenic mice).

In certain embodiments, such transgenic mice are immunized with an immunogen. In certain such embodiments, lymphatic cells (such as B-cells) from mice that express antibodies are obtained. In certain such embodiments, such recovered cells are fused with an "immortalized" cell line, such as a myeloid-type cell line, to produce hybridoma cells. In certain such embodiments, hybridoma cells are screened and selected to identify those that produce antibodies specific to the antigen of interest. Certain exemplary methods and transgenic mice suitable for the production of human monoclonal antibodies are described, e.g., in Jakobovits et al. (1993) *Nature* 362:255-258; Jakobovits (1995) *Curr. Opin. Biotechnol.* 6:561-566; Lonberg et al. (1995) *Intl Rev. Immunol.* 13:65-93; Fishwild et al. (1996) *Nat. Biotechnol.* 14:845-851; Mendez et al. (1997) *Nat. Genet.* 15:146-156; Green (1999) *J. Immunol. Methods* 231:11-23; Tomizuka et al. (2000) *Proc. Nat'l Acad. Sci. USA* 97:722-727; and reviewed in Little et al. (2000) *Immunol. Today* 21:364-370; and WO 98/24893. In certain embodiments, human monoclonal antibodies against ANGPTL3 are suitable for use as therapeutic antibodies. See Part V.G., below.

2. Certain display-based methods

In certain embodiments, human monoclonal antibodies are produced using a display-based method, such as, for example, any of those described below.

In certain embodiments, a monoclonal antibody is produced using phage display techniques. Certain exemplary antibody phage display methods are known to those skilled in the art and are described, for example, in Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). For example, in certain embodiments, a library of antibodies are displayed on the surface of a filamentous phage, such as the nonlytic filamentous phage fd or M13. In certain embodiments, the antibodies are antibody fragments, such as scFvs, Fabs, Fvs with an engineered intermolecular disulfide bond to stabilize the $V_H$-$V_L$ pair, and diabodies. In certain embodiments, antibodies with the desired binding specificity can then be selected. Certain exemplary embodiments of antibody phage display methods are described in further detail below.

In certain embodiments, an antibody phage-display library can be prepared using certain methods known to those skilled in the art. See, e.g., Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.). In certain embodiments, variable gene repertoires are prepared by PCR amplification of genomic DNA or cDNA derived from the mRNA of antibody-secreting cells. For example, in certain embodiments, cDNA is prepared from mRNA of B-cells. In certain embodiments, cDNA encoding the variable regions of heavy and light chains is amplified, for example, by PCR.

In certain embodiments, heavy chain cDNA and light chain cDNA are cloned into a suitable vector. In certain embodiments, heavy chain cDNA and light chain cDNA are randomly combined during the cloning process, thereby resulting in the assembly of a cDNA library encoding diverse scFvs or Fabs. In certain embodiments, heavy chain cDNA and light chain cDNA are ligated before being cloned into a suitable vector. In certain embodiments, heavy chain cDNA and light chain cDNA are ligated by stepwise cloning into a suitable vector.

In certain embodiments, cDNA is cloned into a phage display vector, such as a phagemid vector. Certain exemplary phagemid vectors, such as pCES1, are known to those skilled in the art. In certain embodiments, cDNA encoding both heavy and light chains is present on the same vector. For example, in certain embodiments, cDNA encoding scFvs are cloned in frame with all or a portion of gene III, which encodes the minor phage coat protein pIII. In certain such embodiments, the phagemid directs the expression of the scFv-pIII fusion on the phage surface. Alternatively, in certain embodiments, cDNA encoding heavy chain (or light chain) is cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments. Alternatively, in certain embodiments, cDNA encoding heavy chain and cDNA encoding light chain are present on separate vectors. In certain such embodiments, heavy chain and light chain cDNA is cloned separately, one into a phagemid and the other into a phage vector, which both contain signals for in vivo recombination in the host cell.

In certain embodiments, recombinant phagemid or phage vectors are introduced into a suitable bacterial host, such as *E. coli*. In certain embodiments using phagemid, the host is infected with helper phage to supply phage structural proteins, thereby allowing expression of phage particles carrying the antibody-pIII fusion protein on the phage surface.

In certain embodiments, "synthetic" antibody libraries are constructed using repertoires of variable genes that are rearranged in vitro. For example, in certain embodiments, individual gene segments encoding heavy or light chains (V-D-J or V-J, respectively) are randomly combined using PCR. In certain such embodiments, additional sequence diversity can be introduced into the CDRs, and possibly FRs, e.g., by error prone PCR. In certain such embodiments, additional sequence diversity is introduced into CDR3, e.g., H3 of the heavy chain.

In certain embodiments, "naïve" or "universal" phage display libraries are constructed as described above using nucleic acid from an unimmunized animal. In certain embodiments, the unimmunized animal is a human. In certain embodiments, "immunized" phage display libraries are constructed as described above using nucleic acid from an immunized animal. In certain embodiments, the immunized animal is a human, rat, mouse, hamster, or monkey. In certain such embodiments, the animals are immunized with any of the immunogens described below.

Certain exemplary universal human antibody phage display libraries are available from commercial sources. Certain exemplary libraries include, but are not limited to, the HuCAL® series of libraries from MorphoSys AG (Martinstreid/Munich, Germany); libraries from Crucell (Leiden, the Netherlands) using MAbstract® technology; the n-CoDeR™ Fab library from BioInvent (Lund, Sweden); and libraries available from Cambridge Antibody Technology (Cambridge, UK).

In certain embodiments, the selection of antibodies having the desired binding specificity from a phage display library is achieved by successive panning steps. In certain embodiments of panning, library phage preparations are exposed to antigen. In certain such embodiments, the phage-antigen complexes are washed, and unbound phage are discarded. In certain such embodiments, bound phage are recovered and subsequently amplified by infecting *E. coli*. In certain such embodiments, monoclonal antibody-producing phage may be cloned by picking single plaques. In certain embodiments, the above process is repeated.

In certain embodiments, the antigen used in panning is any of the immunogens described below. In certain embodiments, the antigen is immobilized on a solid support to allow purification of antigen-binding phage by affinity chromatography. In certain embodiments, the antigen is biotinylated, thereby allowing the separation of bound phage from unbound phage using streptavidin-coated magnetic beads. In certain embodiments, the antigen may be immobilized on cells (for direct panning), in tissue cryosections, or on membranes (e.g., nylon or nitrocellulose membranes). Other variations of certain panning procedures may be routinely determined by one skilled in the art.

In certain embodiments, a yeast display system is used to produce monoclonal antibodies. In certain such systems, an antibody is expressed as a fusion protein with all or a portion of the yeast AGA2 protein, which becomes displayed on the surface of the yeast cell wall. In certain such embodiments, yeast cells expressing antibodies with the desired binding specificity can then be identified by exposing the cells to fluorescently labeled antigen. In certain such embodiments, yeast cells that bind the antigen can then be isolated by flow cytometry. See, e.g., Boder et al. (1997) *Nat. Biotechnol.* 15:553-557.

3. Certain affinity maturation methods

In certain embodiments, the affinity of an antibody for a particular antigen is increased by subjecting the antibody to affinity maturation (or "directed evolution") in vitro. In vivo, native antibodies undergo affinity maturation through somatic hypermutation followed by selection. Certain in vitro methods mimic that in vivo process, thereby allowing the production of antibodies having affinities that equal or surpass that of native antibodies.

In certain embodiments of affinity maturation, mutations are introduced into a nucleic acid sequence encoding the variable region of an antibody having the desired binding specificity. See, e.g., Hudson et al. (2003) *Nat. Med.* 9:129-134; Brekke et al. (2002) *Nat. Reviews* 2:52-62. In certain embodiments, mutations are introduced into the variable region of the heavy chain, light chain, or both. In certain embodiments, mutations are introduced into one or more CDRs. In certain such embodiments, mutations are introduced into H3, L3, or both. In certain embodiments, mutations are introduced into one or more FRs. In certain embodiments, a library of mutations is created, for example, in a phage, ribosome, or yeast display library, so that antibodies with increased affinity may be identified by standard screening methods. See, e.g., Boder et al. (2000) *Proc. Nat'l Acad. Sci. USA* 97:10701-10705; Foote et al. (2000) *Proc. Nat'l Acad. Sci. USA* 97:10679-10681; Hoogenboom, *Overview of Antibody Phage-Display Technology and Its Applications*, from *Methods in Molecular Biology: Antibody Phage Display: Methods and Protocols* (2002) 178:1-37 (O'Brien and Aitken, eds., Human Press, Totowa, N.J.); and Hanes et al. (1998) *Proc. Nat'l Acad. Sci. USA* 95:14130-14135.

In certain embodiments, mutations are introduced by site-specific mutagenesis based on information on the antibody's structure, e.g., the antigen binding site. In certain embodiments, mutations are introduced using combinatorial mutagenesis of CDRs. In certain embodiments, all or a portion of the variable region coding sequence is randomly mutagenized, e.g., using *E. coli* mutator cells, homologous gene rearrangement, or error prone PCR. In certain embodiments, mutations are introduced using "DNA shuffling." See, e.g., Crameri et al. (1996) *Nat. Med.* 2:100-102; Fermer et al. (2004) *Tumor Biol.* 25:7-13.

In certain embodiments, "chain shuffling" is used to generate antibodies with increased affinity. In certain embodiments of chain shuffling, one of the chains, e.g., the light chain, is replaced with a repertoire of light chains, while the other chain, e.g., the heavy chain, is unchanged, thus providing specificity. In certain such embodiments, a library of chain shuffled antibodies is created, wherein the unchanged heavy chain is expressed in combination with each light chain from the repertoire of light chains. In certain embodiments, such libraries may then be screened for antibodies with increased affinity. In certain embodiments, both the heavy and light chains are sequentially replaced. In certain embodiments, only the variable regions of the heavy and/or light chains are replaced. In certain embodiments, only a portion of the variable regions, e.g., CDRs, of the heavy and/or light chains are replaced. See, e.g., Hudson et al. (2003) *Nat. Med.* 9:129-134; Brekke et al. (2002) *Nat. Reviews* 2:52-62; Kang et al. (1991) *Proc. Nat'l Acad. Sci. USA* 88:11120-11123; Marks et al. (1992) *Biotechnol.* 10:779-83.

In certain embodiments, mouse monoclonal antibodies that specifically bind human ANGPTL3 (including, but not limited to, mouse monoclonal antibodies raised against mouse ANGPTL3 but which specifically bind (i.e., cross react) with human ANGPTL3) are subject to sequential chain shuffling. In certain embodiments, for example, the heavy chain of a given mouse monoclonal antibody is combined with a new repertoire of human light chains, and antibodies with the desired affinity are selected. In certain such embodiments, the light chains of the selected antibodies are then combined with a new repertoire of human heavy chains, and antibodies with the desired affinity are selected. Thus, in certain embodiments, human antibodies having the desired antigen binding specificity and affinity are selected.

Alternatively, in certain embodiments, the heavy chain of a given mouse monoclonal antibody is combined with a new repertoire of human light chains, and antibodies with the desired affinity are selected from this first round of shuffling. In certain embodiments, the light chain of the original mouse monoclonal antibody is combined with a new repertoire of human heavy chains, and antibodies with the desired affinity are selected from this second round of shuffling. In certain embodiments, human light chains from the antibodies selected in the first round of shuffling are then combined with human heavy chains from the antibodies selected in the second round of shuffling. Thus, in certain embodiments, human antibodies having the desired antigen binding specificity and affinity are selected.

In certain embodiments, a "ribosome display" method is used that alternates antibody selection with affinity maturation. In certain embodiments of a ribosome display method, antibody-encoding nucleic acid is amplified by RT-PCR between the selection steps. Thus, in certain embodiments, error prone polymerases may be used to introduce mutations into the nucleic acid. A nonlimiting example of such a method is described in detail in Hanes et al. (1998) *Proc. Nat'l Acad. Sci. USA* 95:14130-14135.

4. Certain recombinant methods

In certain embodiments, a monoclonal antibody is produced by recombinant techniques. See, e.g., U.S. Pat. No. 4,816,567. In certain such embodiments, nucleic acid encoding monoclonal antibody chains are cloned and expressed in a suitable host cell. For example, in certain embodiments, RNA can be prepared from cells expressing the desired antibody, such as mature B-cells or hybridoma cells, using standard methods. In certain embodiments, the RNA can then be used to make cDNA using standard methods. In certain embodiments, cDNA encoding a heavy or light chain polypeptide is amplified, for example, by PCR, using specific oligonucleotide primers. In certain embodiments, the cDNA is cloned into a suitable expression vector. In certain embodiments, the expression vector is then transformed or transfected into a suitable host cell, such as a host cell that does not endogenously produce antibody. Certain exemplary host cells include, but are not limited to, *E. coli*, COS cells, Chinese hamster ovary (CHO) cells, and myeloma cells. In certain embodiments, wherein heavy and light chains are coexpressed in the same host, reconstituted antibody may be isolated.

In certain embodiments, cDNA encoding a heavy or light chain can be modified. For example, in certain embodiments, the constant region of a mouse heavy or light chain can be replaced with the constant region of a human heavy or light chain. In this manner, in certain embodiments, a chimeric antibody can be produced which possesses human antibody constant regions but retains the binding specificity of a mouse antibody.

In certain embodiments, recombinant antibodies can be expressed in certain cell lines. In certain embodiments, sequences encoding particular antibodies can be used for transformation of a suitable mammalian host cell. According to certain embodiments, transformation can be by any known method for introducing polynucleotides into a host cell. Certain exemplary methods include, but are not limited to, packaging the polynucleotide in a virus (or into a viral vector) and transducing a host cell with the virus (or vector) and using certain transfection procedures known in the art, as exemplified by U.S. Pat. Nos. 4,399,216, 4,912,040, 4,740,461, and 4,959,455. In certain embodiments, the transformation procedure used may depend upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected by determining which cell lines produce high levels of antibodies that specifically bind ANGPTL3.

E. Certain polypeptide immunogens

In certain embodiments, to generate antibodies, an animal is immunized with an immunogen. In certain embodiments, an immunogen is a polypeptide comprising ANGPTL3. In certain embodiments, an immunogen is a polypeptide comprising a fragment of ANGPTL3. In certain embodiments, an immunogen is a polypeptide comprising the N-terminal coiled-coil domain of ANGPTL3. In certain embodiments, an immunogen is a polypeptide comprising the SP1 region of ANGPTL3.

In certain embodiments, an immunogen comprises a mouse ANGPTL3. In certain embodiments, an immunogen comprises a human ANGPTL3. In certain embodiments, an immunogen comprises a mouse ANGPTL3 comprising the amino acid sequence of SEQ ID NO: 1. In certain embodiments, an immunogen comprises a human ANGPTL3 comprising the amino acid sequence of SEQ ID NO: 3. In certain embodiments, an immunogen comprises a fragment of mouse ANGPTL3. In certain embodiments, an immunogen comprises a fragment of SEQ ID NO: 1 from residue 17 to residue 240. In certain embodiments, an immunogen comprises the amino acid sequence of SEQ ID NO: 59. In certain embodiments, an immunogen comprises a fragment of SEQ ID NO: 1 from residue 32 to residue 57. In certain embodiments, an immunogen comprises the amino acid sequence of SEQ ID NO: 9. In certain embodiments, an immunogen comprises the amino acid sequence of SEQ ID NO: 61. In certain embodiments, an immunogen comprises a fragment of human ANGPTL3. In certain embodiments, an immunogen comprises a fragment of SEQ ID NO: 3 from residue 20 to residue 243. In certain embodiments, an immunogen comprises the amino acid sequence of SEQ ID NO: 60. In certain embodiments, an immunogen comprises a fragment of SEQ ID NO: 1 from residue 32 to residue 57. In certain embodiments, an immunogen comprises the amino acid sequence of SEQ ID NO: 10.

In certain embodiments, an immunogen comprises any peptide of about 10-20 contiguous amino acids from residue 17 to residue 240 of SEQ ID NO: 1. In certain embodiments, an immunogen comprises any peptide of about 10-20 contiguous amino acids from residue 20 to residue 243 of SEQ ID NO: 3. In certain embodiments, an immunogen comprises one or more peptides selected from SEQ ID NOs: 9, 10, 12, 13, 59, 60, and 61. In certain embodiments, an immunogen comprises a peptide selected from SEQ ID NOs: 9 and 10. In certain embodiments, an immunogen comprises a peptide comprising one or more amino acid sequences selected from SEQ ID NOs: 59 and 60. In certain embodiments, an immunogen comprises a peptide comprising SEQ ID NOs: 12, 13, and 61. In certain such embodiments, a peptide is selected that is likely to be immunogenic. In certain such embodiments, a peptide is selected that is predicted to be hydrophilic and/or likely to be exposed on the surface of native ANGPTL3 in its folded state. Exemplary guidance for selecting suitable immunogenic peptides is provided, for example, in Ausubel et al. (1989) *Current Protocols in Molecular Biology* Ch. 11.14 (John Wiley & Sons, NY); and Harlow and Lane (1988) *Antibodies: A Laboratory Manual* Ch. 5 (Cold Spring Harbor Laboratory, Cold Spring Harbor, N.Y.).

Certain exemplary algorithms are known to those skilled in the art for predicting whether a peptide segment of a protein is hydrophilic and therefore likely to be exposed on the surface of the protein. Certain such algorithms use the primary sequence information of a protein to make such predictions. Certain such algorithms are based on the method of, for example, Hopp and Woods (1981) *Proc. Nat'l Acad. Sci. USA* 78:3824-3828, or Kyte and Doolittle (1982) *J. Mol. Biol.* 157:105-132. Certain exemplary algorithms are known to those skilled in the art for predicting the secondary structure of a protein based on the primary amino acid sequence of the protein. See, e.g., Corrigan et al. (1982) *Comput. Programs Biomed.* 3:163-168. Certain such algorithms are based on the method of, for example, Chou and Fasman (1978) *Ann. Rev. Biochem.* 47:25-276. In certain embodiments, peptide segments that are predicted to form β-turns, and are therefore likely to be exposed on the surface of a protein, may be selected as immunogens.

In certain embodiments, an animal is immunized with an immunogen and one or more adjuvants. In certain embodiments, an adjuvant is used to increase the immunological response, depending on the host species. Certain exemplary adjuvants include, but are not limited to, Freund's adjuvant (complete and incomplete), mineral salts such as aluminum hydroxide or aluminum phosphate, surface active substances, chitosan, lysolecithin, pluronic polyols, polyanions, peptides, oil emulsions, and potentially useful human adjuvants such as BCG (bacille Calmette-Guerin) and *Corynebacterium parvum*. In certain embodiments, the immune response to an immunogen, e.g., a peptide immunogen, is enhanced by coupling the immunogen to another immunogenic molecule or "carrier protein." Certain exemplary carrier proteins include, but are not limited to, keyhole limpet hemocyanin (KLH), tetanus toxoid, diphtheria toxoid, ovalbumin, cholera toxoid, and immunogenic fragments thereof. For exemplary guidance in coupling peptide immunogens to carrier proteins, see, e.g., Ausubel et al. (1989) *Current Protocols in Molecular Biology* Ch. 11.15 (John Wiley & Sons, NY); and Harlow and Lane (1988) *Antibodies: A Laboratory Manual* Ch. 5 (Cold Spring Harbor Laboratory, Cold Spring Harbor, N.Y.).

In certain embodiments, any of the above immunogens can be produced using standard recombinant methods. For example, in certain embodiments, a polynucleotide encoding a mouse or human ANGPTL3 or a fragment of that polynucleotide may be cloned into a suitable expression vector. In certain embodiments, the polynucleotide comprises the nucleic acid sequence of SEQ ID NO: 5 or SEQ ID NO: 6. In certain embodiments, the recombinant vector is then introduced into a suitable host cell. In certain embodiments, the polypeptide is then isolated from the host cell by standard methods. For certain exemplary methods of recombinant protein expression, see, e.g., Ausubel et al. (1991) *Current Protocols in Molecular Biology* Ch. 16 (John Wiley & Sons, NY).

F. Certain assays

1. Certain binding assays

In certain embodiments, antibodies are screened for binding to ANGPTL3 using certain routine methods that detect binding of antibody to antigen. For example, in certain embodiments, the ability of a monoclonal antibody to bind ANGPTL3 is assayed by standard immunoblotting methods, such as Western blot. See, e.g., Ausubel et al. (1992) *Current Protocols in Molecular Biology* Ch. 10.8 (John Wiley & Sons, NY); Harlow and Lane (1988) *Antibodies: A Laboratory Manual* (Cold Spring Harbor Laboratory, Cold Spring Harbor, N.Y.). In certain embodiments, ANGPTL3 to be used in such assays may be isolated or may be present in a complex mixture of proteins and/or macromolecules.

In certain embodiments, the ability of a monoclonal antibody to bind ANGPTL3 is assayed using a competitive binding assay, which evaluates the ability of a candidate antibody to compete with a known anti-ANGPTL3 antibody for binding to ANGPTL3. In certain such embodiments, the known anti-ANGPTL3 antibody is any of the monoclonal antibodies described below in Part VI.J. In certain embodiments, a competitive binding assay is performed using ELISA. See, e.g., Harlow and Lane (1988) *Antibodies: A Laboratory Manual* Ch. 14 (Cold Spring Harbor Laboratory, Cold Spring Harbor, N.Y.).

In certain embodiments, a binding assay is used to quantify the binding kinetics (e.g., rate constant) or the binding affinity (e.g., association or dissociation constant) of an antibody against ANGPTL3. In certain embodiments, the kinetics or affinity of binding is determined in the "solid-phase" by immobilizing antigen (e.g., ANGPTL3) on a solid support. The immobilized antigen "captures" antibody from solution. In certain embodiments, the kinetics or affinity of binding is determined in the "solid-phase" by immobilizing antibody (e.g., antibody against ANGPTL3) on a solid support. The immobilized antibody "captures" antigen from solution.

In certain embodiments, binding kinetics or binding affinity is determined using ELISA-based methods. In certain embodiments, binding kinetics or binding affinity is determined using biosensor-based technology, such as Biacore surface plasmon resonance technology (Biacore, Piscataway, N.J.). Certain such methods are known to those skilled in the art. See, e.g., McCafferty et al. (eds.) (1996) *Antibody Engineering: A Practical Approach* (IRL, Oxford, UK); Goldberg et al. (1993) *Curr. Opin. Immunol.* 5:278-281; Karlsson et al. (1991) *J. Immunol. Methods* 145:229-240; Malmqvist (1993) *Curr. Opin. Immunol.* 5:282-286; for review, see Hoogenboom, *Overview of Antibody Phage-Display Technology and Its Applications*, from *Methods in Molecular Biology: Antibody Phage Display: Methods and Protocols* (2002) 178:1-37 at 19 (O'Brien and Aitken, eds., Human Press, Totowa, N.J.).

In certain embodiments, the binding kinetics or binding affinity of a Fab fragment that specifically binds to ANGPTL3 is determined. In certain instances, Fab fragments have the property of not multimerizing. Multimerization can, in certain instances, complicate the measurement of binding kinetics and binding affinity in "solid phase" methods. See, e.g., Hoogenboom, *Overview of Antibody Phage-Display Technology and Its Applications*, from *Methods in Molecular Biology: Antibody Phage Display: Methods and Protocols* (2002) 178:1-37 at 19 (O'Brien and Aitken, eds., Human Press, Totowa, N.J.). Thus, in certain embodiments, a Fab fragment that specifically binds to ANGPTL3 is suitable for use in a binding assay in which antigen is immobilized to a solid support, such as, for example, an ELISA-based assay or a Biacore assay. In certain embodiments, Fab fragments are generated from an intact antibody that specifically binds to ANGPTL3 using enzymatic methods. In certain embodiments, Fab fragments are produced by expressing nucleic acids encoding Fab fragments in a recombinant expression system, such as those described above, Part V.D.3.

In certain embodiments, the binding kinetics or binding affinity of an antibody against ANGPTL3 is determined using "solution phase" methods. In such methods, the kinetics or affinity of binding is measured for an antibody-antigen complex in solution. Certain such methods are known to those skilled in the art. A nonlimiting example of such a method is the "kinetic exclusion assay," or "KinExA." See, e.g., Blake et al. (1996) *J. Biol. Chem.* 271:27677-27685; Drake et al. (2004) *Anal. Biochem.* 328:35-43 (comparing Biacore "solid phase" and KinExA "solution phase" methods). In certain embodiments, instrumentation for performing KinExA is supplied by Sapidyne Instruments, Inc. (Boise, Id.).

In certain embodiments, the binding kinetics or binding affinity of a multivalent antibody or an antibody that multimerizes is determined using a solution phase method. In certain instances, the measurement of the binding kinetics or the binding affinity of a multivalent antibody or an antibody that multimerizes is amenable to solution phase analysis.

In certain embodiments, the binding affinity of an anti-ANGPTL3 antibody, as measured by its $K_D$, is about $10^{-6}$M or less. In certain embodiments, the binding affinity of an anti-ANGPTL3 antibody is about $10^{-7}$ M, about $10^{-8}$M, or about $10^{-9}$M or less. In certain such embodiments, an anti-ANGPTL3 antibody may be used as a therapeutic antibody. See, e.g., Hudson et al. (2003)*Nat. Med.* 9:129-134. In certain embodiments, binding affinities of less than $10^{-9}$M (e.g., binding affinities from about 500 pM to about 0.5 pM, including but not limited to, binding affinities from about 100 pM to about 5 pM) are achievable, e.g., using affinity maturation techniques. See, e.g., Boder et al. (2000) *Proc. Nat'l Acad. Sci. USA* 97:10701-10705. In certain embodiments, the binding affinity of an anti-ANGPTL3 antibody is less than about $5 \times 10^{-8}$ M.

In certain embodiments, a monoclonal antibody that was raised against mouse ANGPTL3 is screened for specific binding to human ANGPTL3 using certain routine detection methods, e.g., such as those described herein. The ability of a monoclonal antibody to bind both mouse and human ANGPTL3 (i.e., to demonstrate "cross-reactivity") indicates the presence of the same epitope in mouse and human ANGPTL3. In certain embodiments of detection methods that use denaturing conditions (e.g., Western blot), cross-reactivity indicates that a mouse monoclonal antibody binds to the same "linear" epitope in mouse and human ANGPTL3. In certain embodiments of detection methods that use non-denaturing conditions, cross-reactivity indicates that a mouse monoclonal antibody binds to the same epitope (e.g., a linear epitope or a conformational epitope) in mouse and human ANGPTL3.

2. Certain methods for epitope mapping

In various embodiments, the epitope to which a monoclonal antibody binds is identified by any of a number of assays. Certain exemplary assays are described, for example, in Morris, *Methods in Molecular Biology Vol. 66: Epitope Mapping Protocols* (1996) (Humana Press, Totowa, N.J.). For example, epitope mapping may be achieved by gene fragment expression assays or peptide-based assays. In certain embodiments of a gene fragment expression assay, for example, nucleic acids encoding fragments of ANGPTL3 are expressed in prokaryotic cells and isolated. In certain such embodiments, the ability of a monoclonal antibody to bind those fragments is then assessed, e.g., by immunoprecipitation or immunoblotting. In certain embodiments, nucleic acids encoding fragments of ANGPTL3 are transcribed and translated in vitro in the presence of radioactive amino acids. The radioactively labeled fragments of ANGPTL3 are then tested for binding to a monoclonal antibody. In certain embodiments, fragments of ANGPTL3 are generated by proteolytic fragmentation. In certain embodiments, an epitope is identified using libraries of random peptides displayed on the surface of phage or yeast. In certain embodiments, an epitope is identified by testing a library of overlapping synthetic peptide fragments of ANGPTL3 for binding to a monoclonal antibody. In certain embodiments, an epitope is identified using a competition assay, such as those described below. In certain embodiments, an epitope may be further defined using alanine-scanning mutagenesis, e.g., as described below.

3. Certain competition assays

In certain embodiments, monoclonal antibodies that bind to the same epitope of ANGPTL3 as a monoclonal antibody of interest are identified. In certain embodiments, such monoclonal antibodies are identified by epitope mapping, e.g., as described above. In certain embodiments, such monoclonal antibodies are identified by routine competition assays. See, e.g., Harlow and Lane (1988) *Antibodies: A Laboratory Manual* ch. 14 (Cold Spring Harbor Laboratory, Cold Spring Harbor, N.Y.). In a nonlimiting exemplary competition assay, ANGPTL3 or a fragment thereof is immobilized onto the wells of a multiwell plate. In certain such embodiments, the monoclonal antibody of interest is labeled with a fluorescent label (in certain embodiments, fluorescein isothiocyanate) by standard methods. In certain such embodiments, mixtures of the labeled monoclonal antibody of interest and an unlabeled test monoclonal antibody are added to the wells. In certain such embodiments, the fluorescence in each well is quantified to determine the extent to which the unlabeled test monoclonal antibody blocks the binding of the labeled monoclonal antibody of interest. In certain embodiments, monoclonal antibodies are deemed to share an epitope if each blocks the binding of the other by 50% or greater. Exemplary competition assays are also described, e.g., in Morris, *Methods in Molecular Biology Vol. 66: Epitope Mapping Protocols* (1996) (Humana Press, Totowa, N.J.). A nonlimiting exemplary competition assay is provided below, Part VI.O.

4. Certain assays for identifying neutralizing antibodies

In certain embodiments, monoclonal antibodies are screened for those that are neutralizing antibodies, i.e., those that reduce an activity of ANGPTL3 in vivo and/or in vitro. In certain embodiments, an activity of ANGPTL3 is the ability of ANGPTL3 to inhibit LPL. Thus, in certain embodiments, a neutralizing antibody is identified by its ability to increase LPL activity in the presence of ANGPTL3. In certain such embodiments, a neutralizing antibody increases LPL activity by at least about 20%, 30%, 40%, 50%, 60%, 70%, 80%, 90%, or 95%, relative to a control antibody. Certain exemplary assays for measuring LPL activity in vivo and in vitro are known in the art.

In certain embodiments, a neutralizing antibody that reduces an activity of ANGPTL3 in vivo is identified by its ability to decrease the level of at least one serum lipid. Certain exemplary serum lipids include, but are not limited to, triglycerides, cholesterol, and free fatty acids. In certain such embodiments, a neutralizing antibody decreases the level of at least one serum lipid by at least about 10%, 20%, 30%, 40%, 50%, 60%, 70%, 80%, 90%, or 95%, relative to a control antibody. In certain embodiments, a neutralizing antibody that reduces an activity of ANGPTL3 in vivo is identified by its ability to counteract or confer protection from certain effects of a fat-containing diet. Certain exemplary effects include, but are not limited to, weight gain, obesity, glucose intolerance (hyperglycemia), insulin insensitivity (hyerpinsulinemia), hepatic steatosis (fatty liver), and intramyocellular lipid accumulation.

G. Certain pharmaceutical compositions and methods of treatment using neutralizing monoclonal antibodies In certain embodiments, a neutralizing antibody may be used as a therapeutic antibody. Certain exemplary neutralizing antibodies to be used as therapeutic antibodies include, but are not limited to, chimeric antibodies, humanized antibodies, and human antibodies. Those skilled in the art are familiar with the use of certain antibodies as therapeutic agents. For example, over a dozen antibodies have been approved by the FDA for use as therapeutic agents since the mid-1980s. See, e.g., Hudson et al. (2003) *Nat. Med.* 9:129-134; Gura (2002) *Nature* 417:584-586; Brekke et al. (2002) *Nat. Reviews* 2:52-62. Certain FDA-approved antibodies include those used to treat various cancers, inflammation, and viral infections and to prevent transplant rejection. See, e.g., Gura (2002) *Nature* 417:584-586; Brekke et al. (2002) *Nat. Reviews* 2:52-62. Furthermore, over a dozen antibodies are currently in clinical trials. See, e.g., Brekke et al. (2002) *Nat. Reviews* 2:52-62.

In certain embodiments, methods are provided for treating a disorder of lipid metabolism comprising administering an effective amount of a neutralizing antibody against ANGPTL3. In certain embodiments, methods are provided for treating an acute disorder of lipid metabolism comprising administering an effective amount of a neutralizing antibody against ANGPTL3. In certain embodiments, methods are provided for treating a chronic disorder of lipid metabolism comprising administering an effective amount of a neutralizing antibody against ANGPTL3. In certain embodiments, a method for treating a disorder of lipid metabolism further comprises administering an effective amount of a neutralizing antibody against ANGPTL4. See, e.g., PCT Publication No. WO 2006/074228.

As used herein, "disorders of lipid metabolism" include, but are not limited to, disorders that can lead to secondary hyperlipidemia (including hypertriglyceridemia and hypercholesterolemia). Certain exemplary disorders of lipid metabolism include, but are not limited to, atherosclerosis, dyslipidemia, hypertriglyceridemia (including drug-induced hypertriglyceridemia, diuretic-induced hypertriglyceridemia, alcohol-induced hypertriglyceridemia, β-adrenergic blocking agent-induced hypertriglyceridemia, estrogen-induced hypertriglyceridemia, glucocorticoid-induced hypertriglyceridemia, retinoid-induced hypertriglyceridemia, cimetidine-induced hypertriglyceridemia, and familial hypertriglyceridemia), acute pancreatitis associated with hypertriglyceridemia, chylomicron syndrome, chylomicronemia, Apo-E deficiency, LPL deficiency or hypoactivity, hyperlipidemia (including familial combined hyperlipidemia), hypercholesterolemia, gout associated with hypercholesterolemia, xanthomatosis (subcutaneous cholesterol deposits), coronary artery disease (also called ischaemic heart disease), inflammation associated with coronary artery disease, restenosis, peripheral vascular diseases, and stroke. Certain exemplary disorders of lipid metabolism include, but are not limited to, disorders related to body weight, such as obesity, metabolic syndrome including independent components of metabolic syndrome (e.g., central obesity, FBG/pre-diabetes/diabetes, hypercholesterolemia, hypertriglyceridemia, and hypertension), hypothyroidism, uremia, and other conditions associated with weight gain (including rapid weight gain), weight loss, maintenance of weight loss, or risk of weight regain following weight loss. Certain exemplary disorders of lipid metabolism include, but are not limited to, related blood sugar disorders, such as diabetes, hypertension, and polycystic ovarian syndrome related to insulin resistance. Certain exemplary disorders of lipid metabolism include, but are not limited to, renal transplantation, nephrotic syndrome, Cushing's syndrome, acromegaly, systemic lupus erythematosus, dysglobulinemia, lipodystrophy, glycogenosis type I, and Addison's disease.

Disorders of lipid metabolism include, but are not limited to secondary hypertriglycerolemia (HTG, including but not limited to types I, V, and IV), including but not limited to, HTG due to diet (including, but not limited to, excessive alcohol consumption, weight gain, and obesity), drugs (including but not limited to, exogenous estrogen, tamoxifen, retinoids, thiazides, chlorthalidone, beta-clockers, protease inhibitors (including but not limited to ritonavir), propofol infusion, and parenteral lipid infusions), disorders of metabolism (including but not limited to diabetes, pregnancy, chronic renal failure, hypothyroidism, familial hyperlipidemia, and pancreatitis).

Disorders of lipid metabolism include, but are not limited to, lipid disorders associated with vascular access dysfunction, lipid disorders associated with proliferative diseases, including but not limited to, neoplasia (including but not limited to prostate, kidney, liver, breast, ovarian, lung, and pancreatic cancers), disorders that occur in response to inflammation, including but not limited to, those associated with, e.g., infectious diseases, wound healing, immunodeficiency syndromes (AIDS and others, including but not limited to those syndromes associated with aberrant development), scar formation, atherosclerosis, restenosis and transplantation rejection, autoimmune disorders, and chronic inflammatory diseases and disorders, which include but are not limited to, diseases including but not limited to rheumatoid arthritis, systemic lupus erythromatosis, and disorders including but not limited to Crohn's disease, colitis, inflammatory bowel disease, reactive arthritis, including Lyme disease, insulin dependent diabetes, organ specific autoimmunity, multiple sclerosis, Hashimoto's thyroiditis and Grave's disease, Sjogren's syndrome, contact dermatitis, psoriasis, scleroderma, graft versus host disease, sarcoidosis, malaria, sepsis, pancreatitis, atopic conditions, including but not limited to asthma and allergy, including but not limited to allergic rhinitis, gastrointestinal allergies, including but not limited to food allergies, eosinophilia, conjunctivitis and glomerular nephritis, blood coagulation disorders, endotoxic shock and other inflammation mediated disorders such as sleep apnea and sleepiness.

In certain embodiments, methods are provided for treating a disorder of lipid metabolism comprising administering an effective amount of an antibody to ANGPTL3 and at least one additional therapeutic agent. In certain such embodiments, an additional therapeutic agent is administered in an effective amount. In certain embodiments, an additional therapeutic agent is another antibody to ANGPTL3. In certain embodiments, an additional therapeutic is a neutralizing antibody against ANGPTL4. See, e.g., PCT Publication No. WO 2006/074228. In certain embodiments, an additional therapeutic agent is a non-antibody agent. In certain embodiments, an additional therapeutic agent is an agent that lowers the level of one or more serum lipids. Certain exemplary additional therapeutic agents include, but are not limited to, cholesterol synthesis inhibitors (statins), such as HMG-CoA reductase inhibitors (e.g., lovastatin, simvastatin, pravastatin, and fluvastatin); bile sequestering agents, such as cholestyramine and other resins; VLDL secretion inhibitors, such as niacin; lipophilic antioxidants, such as Probucol; acyl-CoA cholesterol acyl transferase inhibitors; farnesoid X receptor antagonists; sterol regulatory binding protein cleavage activating protein (SCAP) activators; microsomal triglyceride transfer protein (MTP) inhibitors; and ApoE-related peptide. In certain embodiments, the additional therapeutic agent is an agent that raises high density lipoprotein (HDL). Nonlimiting examples of such agents include, but are not limited to, cholesteryl ester transfer protein (CETP) inhibitors.

In certain embodiments, a pharmaceutical composition is provided that comprises an effective amount of an antibody to ANGPTL3 and a pharmaceutically acceptable diluent, carrier, solubilizer, emulsifier, preservative and/or adjuvant. In certain embodiments, a pharmaceutical composition is provided that comprises an effective amount of an antibody to ANGPTL3 and an effective amount of at least one additional therapeutic agent, together with a pharmaceutically acceptable diluent, carrier, solubilizer, emulsifier, preservative and/or adjuvant. In certain embodiments, the at least one additional therapeutic agent is selected from those described above.

In certain embodiments, formulation materials for pharmaceutical compositions are nontoxic to recipients at the dosages and concentrations employed.

In certain embodiments, the pharmaceutical composition comprises formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediamine tetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight polypeptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants. (*Remington's Pharmaceutical Sciences*, 18$^{th}$ Edition, A. R. Gennaro, ed., Mack Publishing Company (1990).

In certain embodiments, an antibody to ANGPTL3 or other therapeutic molecule is linked to a half-life extending vehicle. Certain exemplary half-life extending vehicles are known in the art. Certain such vehicles include, but are not limited to, the Fc domain, polyethylene glycol, and dextran. Certain such vehicles are described, e.g., in published PCT Application No. WO 99/25044.

In certain embodiments, an optimal pharmaceutical composition will be determined by one skilled in the art depending upon, for example, the intended route of administration, delivery format, and desired dosage. See, e.g., *Remington's Pharmaceutical Sciences*, supra. In certain embodiments, such compositions may influence the physical state, stability, rate of in vivo release, or rate of in vivo clearance of a neutralizing antibody.

In certain embodiments, a primary vehicle or carrier in a pharmaceutical composition may be either aqueous or non-aqueous in nature. For example, in certain embodiments, a suitable vehicle or carrier may be water for injection, physiological saline solution, or artificial cerebrospinal fluid, possibly supplemented with other materials common in compositions for parenteral administration. Certain exemplary vehicles include, but are not limited to, neutral buffered saline and saline mixed with serum albumin. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a composition comprising an antibody to ANGPTL3, with or without at least one additional therapeutic agents, may be prepared for storage by mixing the selected composition having the desired degree of purity with optional formulation agents (*Remington's Pharmaceutical Sciences*, supra) in the form of a lyophilized cake or an aqueous solution. In certain embodiments, a composition comprising an antibody to ANGPTL3, with or without at least one additional therapeutic agent, may be formulated as a lyophilizate using appropriate excipients such as sucrose.

In certain embodiments, a pharmaceutical composition is selected for parenteral delivery. In certain embodiments, a pharmaceutical composition is selected for inhalation or for delivery through the digestive tract, such as orally. Certain exemplary techniques for preparing pharmaceutically acceptable compositions are within the skill of one skilled in the art.

In certain embodiments, formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a pharmaceutical composition may be in the form of a pyrogen-free, parenterally acceptable aqueous solution comprising the desired antibody to ANGPTL3, with or without additional therapeutic agents, in a pharmaceutically acceptable vehicle. In certain embodiments, a vehicle for parenteral injection is sterile distilled water in which the antibody to ANGPTL3, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an antibody to ANGPTL3, with or without at least one additional therapeutic agent, may be formulated as a dry powder for inhalation. In certain embodiments, an inhalation solution comprising an antibody to ANGPTL3, with or without at least one additional therapeutic agent, may be formulated with a propellant for aerosol delivery. In certain embodiments, solutions may be nebulized.

In certain embodiments, a formulation may be administered orally. In certain embodiments, an antibody to ANGPTL3, with or without at least one additional therapeutic agent, that is administered in this fashion may be formulated with or without carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the antibody to ANGPTL3 with or without any additional therapeutic agents. In certain embodiments, diluents, flavorings, low melting point waxes, vegetable oils, lubricants, suspending agents, tablet disintegrating agents, and/or binders may also be employed.

In certain embodiments, a pharmaceutical composition comprises an effective amount of an antibody to ANGPTL3, with or without at least one additional therapeutic agent, in a mixture with non-toxic excipients which are suitable for the manufacture of tablets. In certain embodiments, by dissolving the tablets in sterile water, or another appropriate vehicle, solutions may be prepared in unit-dose form. Certain exemplary excipients include, but are not limited to, inert diluents (for example, calcium carbonate, sodium carbonate, sodium bicarbonate, lactose, and calcium phosphate); binding agents (for example, starch, gelatin, and acacia); and lubricating agents (for example, magnesium stearate, stearic acid, and talc).

Additional pharmaceutical compositions will be evident to those skilled in the art, including formulations comprising an antibody to ANGPTL3, with or without at least one additional therapeutic agent, in sustained- or controlled-delivery formulations. Certain exemplary sustained- or controlled-delivery formulations include, but are not limited to, liposome carriers, bio-erodible microparticles, porous beads, and depot injections. Certain exemplary techniques for preparing certain formulations are known to those skilled in the art. In certain embodiments, sustained-release preparations may include semipermeable polymer matrices in the form of shaped articles, e.g. films or microcapsules. Certain exemplary sustained release matrices include, but are not limited to, polyesters, hydrogels, polylactides (see, e.g., U.S. Pat. No. 3,773,919 and EP 058,481), copolymers of L-glutamic acid and gamma ethyl-L-glutamate (see, e.g., Sidman et al. (1983) *Biopolymers* 22:547-556), poly (2-hydroxyethyl-methacrylate) (see, e.g., Langer et al. (1981) *J. Biomed. Mater. Res.* 15:167-277 and Langer (1982) *Chem. Tech.* 12:98-105), ethylene vinyl acetate (Langer et al., supra), and poly-D(−)-3-hydroxybutyric acid (EP 133,988). In certain embodiments, sustained release compositions may include liposomes, which can be prepared, in certain embodiments, by any of several methods known in the art. See e.g., Eppstein et al. (1985) *Proc. Natl. Acad. Sci. USA*, 82:3688-3692; EP 036, 676; EP 088,046; and EP 143,949.

In certain embodiments, a pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., lyophilized) that is reconstituted prior to administration.

In certain embodiments, kits for producing a single-dose administration unit are provided. In certain embodiments, the kits may each contain both a first container having a dried protein and a second container having an aqueous formulation. In certain embodiments, kits containing single or multi-chambered pre-filled syringes (e.g., liquid syringes and lyo-syringes) are included.

In certain embodiments, the effective amount of a pharmaceutical composition comprising an antibody to ANGPTL3, with or without at least one additional therapeutic agent, to be employed therapeutically will depend, for example, upon the context and objectives of treatment. One skilled in the art will appreciate that the appropriate dosage levels for treatment, according to certain embodiments, will thus vary depending, in part, upon the molecule delivered, the indication for which the antibody to ANGPTL3, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg of patient body weight, up to about 100 mg/kg or more, depending on the factors mentioned above. In certain embodiments, the dosage may range from 0.1 µg/kg up to about 100 mg/kg; 1 µg/kg up to about 100 mg/kg; or 5 µg/kg up to about 100 mg/kg, including all points (including fractions) between any of the foregoing endpoints. In certain embodiments, the dosage is between about 10 mg/kg body weight and about 60 mg/kg body weight. In certain embodiments, the dosage is about 10 mg/kg body weight, about 20 mg/kg body weight, about 30 mg/kg body weight, about 40 mg/kg body weight, about 50 mg/kg body weight, or about 60 mg/kg body weight.

In certain embodiments, a human dose of a neutralizing antibody against ANGPTL3 is determined based on the efficacious dose of the same antibody in mice. In certain embodiments, a human dose of a neutralizing antibody against ANGPTL3 is determined using "Guidance for Industry: Estimating the Maximum Safe Starting Dose in Initial Clinical Trials for Therapeutics in Adult Healthy Volunteers," U.S. Department of Health and Human Services, Food and Drug Administration, and Center for Drug Evaluation and Research (CDER), Jul. 2005 (Pharmacology and Toxicology). In certain embodiments, a human dose of a neutralizing antibody against ANGPTL3 is between 0.07 mg/kg and 7 mg/kg. In certain embodiments, a human dose of a neutralizing antibody against ANGPTL3 is between 0.1 mg/kg and 5 mg/kg. In certain embodiments, a human dose of a neutralizing antibody against ANGPTL3 is between 0.1 mg/kg and 2 mg/kg. In various embodiments, a neutralizing antibody against ANGPTL3 is administered to a patient twice per week, once per week, once every two weeks, or once per month.

In certain embodiments, a suitable dosage may be determined by one skilled in the art, for example, based on animal studies.

In certain embodiments, the frequency of dosing will take into account the pharmacokinetic parameters of an antibody to ANGPTL3 and, if applicable, any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. In certain embodiments, further refinement of the appropriate dosage is routinely made by those skilled in the art and is within the ambit of tasks routinely performed by them. In certain embodiments, appropriate dosages may be ascertained through use of appropriate dose-response data. In certain embodiments, a patient receives one dose of a pharmaceutical composition comprising an antibody to ANGPTL3. In certain embodiments, a patient receives one, two, three, or four doses per day of a pharmaceutical composition comprising an antibody to ANGPTL3. In certain embodiments, a patient receives one, two, three, four, five, or six doses per week of a pharmaceutical composition comprising an antibody to ANGPTL3. In certain embodiments, a patient receives one or two doses per month of a pharmaceutical composition comprising an antibody to ANGPTL3.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an antibody to ANGPTL3, with or without at least one additional therapeutic agent, in an ex vivo manner. In certain such instances, cells, tissues and/or organs that have been removed from the patient are exposed to a pharmaceutical composition comprising an antibody to ANGPTL3, with or without at least one additional therapeutic agent, after which the cells, tissues and/or organs are subsequently implanted back into the patient.

In certain embodiments, an antibody to ANGPTL3, with or without at least one additional therapeutic agent, is delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

H. Certain methods of detection and diagnosis

In certain embodiments, antibodies against ANGPTL3 are used to detect the presence of ANGPTL3 in vivo or in vitro. In certain embodiments, the level of ANGPTL3 in vivo is correlated with a medical condition, such as a disorder of lipid metabolism, thereby allowing diagnosis of the medical condition. Certain exemplary medical conditions that may be diagnosed by an antibody against ANGPTL3 are set forth above.

Certain exemplary detection methods are known in the art and include, but are not limited to, ELISA, radioimmunoassay, immunoblot, Western blot, immunofluorescence, and immunoprecipitation. In certain embodiments, antibodies against ANGPTL3 are modified so that they may be directly detected, for example, by linking the antibody to a label. Certain exemplary labels include, but are not limited to, fluorophores, chromophores, radioactive atoms, electron-dense reagents, enzymes, and ligands. In certain embodiments, antibodies against ANGPTL3 are detected by using a labeled "secondary" antibody that binds to a class of antibodies (e.g., a goat anti-mouse antibody).

I. Certain screening methods for ANGPTL3 antagonists and agonists

In certain embodiments, a method of screening for an agent that binds to ANGPTL3 is provided. In certain embodiments, a screening method comprises exposing ANGPTL3 to one or more candidate agents under suitable conditions and assessing binding of ANGPTL3 to the one or more candidate agents. In certain embodiments, a screening method comprises using an antibody against ANGPTL3 in a competitive binding assay. In certain such embodiments, a first binding mixture comprising an antibody against ANGPTL3 and ANGPTL3 is used. The amount of binding between ANGPTL3 and the antibody in the first binding mixture ($M_0$) is measured. A second binding mixture comprising the antibody, ANGPTL3, and an agent to be screened is also used. The amount of binding between ANGPTL3 and the antibody in the second binding mixture ($M_1$) is measured. The amount of binding in the first binding mixture is compared with the amount of binding in the second binding mixture, for example, by calculating the $M_1/M_0$ ratio. An agent is considered to be capable of binding ANGPTL3 if the amount of binding of antibody to ANGPTL3 in the second binding mixture is less than the amount of binding of antibody to ANGPTL3 in the first binding mixture. In certain embodiments, an agent that binds ANGPTL3 decreases the binding of antibody to ANGPTL3 by at least about 10% (i.e., $M_1/M_0<0.9$), by at least about 30% (i.e., $M_1/M_0<0.7$), by at least about 50% (i.e., $M_1/M_0<0.5$), by at least about 70% (i.e., $M_1/M_0<0.3$), by at least about 80% (i.e., $M_1/M_0<0.2$), by at least about 90% (i.e., $M_1/M_0<0.1$), or by at least about 95% (i.e., $M_1/M_0<0.05$).

In certain embodiments, the ANGPTL3 to be used in any of the screening methods described above is the N-terminal coiled-coil domain of ANGPTL3 or a fragment thereof. Based on the applicants' observation that certain antibodies that bind within the N-terminal coiled-coil domain of ANGPTL3 can decrease serum triglyceride and serum cholesterol levels in vivo, an agent (e.g., an antibody or a non-antibody agent) identified by a screening method as binding to the N-terminal coiled-coil domain of ANGPTL3 is a candidate antagonist of ANGPTL3 activity. In certain embodiments, an agent (e.g., an antibody or a non-antibody agent) identified by a screening method as binding to the SP1 region within the N-terminal coiled-coil domain of ANGPTL3 is a candidate antagonist of ANGPTL3 activity.

In certain embodiments, antagonist activity is verified by demonstrating that the candidate antagonist neutralizes ANGPTL3 activity in an in vivo or in vitro assay. Certain exemplary assays are described herein. One skilled in the art can select and/or adapt an appropriate assay from those described herein and/or those known in the art. In certain embodiments, antagonists of ANGPTL3 are used in the treatment of disorders of lipid metabolism.

In certain embodiments, methods of screening for agents that bind to the fibrinogen domain of ANGPTL3 are provided. In certain embodiments, an agent that binds within the fibrinogen domain of ANGPTL3 may enhance ANGPTL3 activity. Thus, an agent (e.g., an antibody or a non-antibody agent) identified by a screening method as binding to the fibrinogen domain of ANGPTL3 is a candidate agonist of ANGPTL3 activity. In certain embodiments, agonist activity is verified by demonstrating that the candidate agonist enhances ANGPTL3 activity in an in vitro or an in vivo assay. One skilled in the art can select and/or adapt an appropriate assay based on the assays known in the art and/or the assays described herein. In certain embodiments, agonists of ANGPTL3 are used in the treatment of certain disorders related to excessive weight loss, such as anorexia nervosa, bulimia nervosa and the cachexia (wasting) associated with diseases such as cancer, cystic fibrosis, and AIDS.

Certain exemplary agents that can be screened for binding to ANGPTL3 include, but are not limited to, antibodies, small molecules (e.g., organic compounds, organometallic compounds, salts of organic and organometallic compounds, saccharides, amino acids, nucleosides, and nucleotides), aptamers, peptides, and peptide mimetics. Certain exemplary peptides include soluble peptides, which include, but are not limited to, members of random peptide libraries (see, e.g., Lam et al., (1991) *Nature* 354:82-84; Houghten et al., (1991) *Nature* 354:84-86) and members of combinatorial chemistry-derived molecular libraries made of D- and/or L-configuration amino acids; and phosphopeptides, which include, but are not limited to, members of random or partially degenerate, directed phosphopeptide libraries (see, e.g., Songyang (1993) *Cell* 72:767-778).

In certain embodiments, computer modeling and searching technologies permit identification of compounds, or the improvement of already identified compounds, that bind ANGPTL3. Certain exemplary molecular modeling systems include, but are not limited to, the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

J. nucleic acid antagonists of ANGPTL3

In certain embodiments, an isolated nucleic acid that decreases the expression of a nucleic acid encoding ANGPTL3 is provided. In certain embodiments, the nucleic acid encoding ANGPTL3 encodes mouse ANGPTL3. In certain embodiments, the nucleic encoding ANGPTL3 encodes human ANGPTL3. In certain embodiments, the isolated nucleic acid is an antisense nucleic acid. In certain such embodiments, the antisense nucleic acid is a single stranded DNA molecule that promotes the degradation of a target mRNA by an RNaseH-based mechanism. In certain embodiments, an antisense nucleic acid is an oligonucleotide of about 8-30 nucleotides in length (including all points between the end points). In certain embodiments, an antisense nucleic acid is an oligonucleotide of about 18-26 nucleotides in length.

In certain embodiments, an antisense nucleic acid encompasses an RNA molecule that reduces expression of a target nucleic acid by an RNA interference (RNAi)-based mechanism. Certain exemplary RNA molecules suitable for RNAi include, but are not limited to, short interfering RNAs (siRNAs), microRNAs (mRNAs), tiny non-coding RNAs (tncRNAs), and small modulatory RNA (snRNA). For review of certain exemplary RNAi mechanisms and RNA molecules for use in RNAi, see, e.g., Novina et al. (2004) *Nature* 430:161-164.

In certain embodiments, an siRNA that decreases expression of a nucleic acid encoding ANGPTL3 is provided. In certain embodiments, an siRNA is an oligonucleotide of about 18-26 nucleotides in length (including all points between the endpoints). In certain embodiments, an siRNA is an oligonucleotide of about 20-24 nucleotides in length, or an oligonucleotide of about 21-23 nucleotides in length. In certain embodiments, an siRNA is double-stranded RNA. In certain embodiments, an siRNA will induce the degradation of a target mRNA molecule that is complementary to the antisense strand of the siRNA. See, e.g., Novina et al. (2004) *Nature* 430:161-164.

The activity of an antisense nucleic acid, such as an antisense DNA molecule or an siRNA, is often affected by the secondary structure of the target mRNA. See, e.g., Vickers et al. (2003) *J. Biol. Chem.* 278:7108-7118. Thus, in certain embodiments, an antisense nucleic acid is selected that is complementary to a region of a target mRNA that is available for base-pairing. In certain embodiments, a suitable region of a target mRNA is identified by performing a "gene walk," e.g., by empirically testing a number of antisense oligonucleotides for their ability to hybridize to various regions along a target mRNA and/or to reduce target mRNA expression. See, e.g., Vickers et al. (2003) *J. Biol. Chem.* 278:7108-7118; Hill et al. (1999) *Am. J. Respir. Cell Mol. Biol.* 21:728-737. In certain embodiments, a suitable region of a target mRNA is identified using an mRNA secondary structure prediction program or related algorithm to identify regions of a target mRNA that do not hybridize to any other regions of the target mRNA. See, e.g., Hill et al. (1999) *Am. J. Respir. Cell Mol. Biol.* 21:728-737. In certain embodiments, a combination of both of the above methods is used to identify a suitable region of a target mRNA. See e.g., Hill et al. (1999) *Am. J. Respir. Cell Mol. Biol.* 21:728-737.

In certain embodiments, a method of reducing ANGPTL3 activity by reducing expression of a nucleic acid encoding ANGPTL3 is provided. In certain embodiments, the method comprises reducing expression of a nucleic acid encoding ANGPTL3 in a cell in vitro or in vivo. In certain embodiments, the method comprises administering an antisense nucleic acid that reduces expression of a nucleic acid encoding ANGPTL3 to a cell in vitro or in vivo. In certain embodiments, the nucleic acid encoding ANGPTL3 encodes human ANGPTL3. In certain embodiments, the nucleic acid encoding ANGPTL3 encodes mouse ANGPTL3.

In certain embodiments, a method of treating a disorder of lipid metabolism, such as any of those described above, is provided. In certain embodiments, the method comprises administering to a patient an effective amount of an antisense nucleic acid that reduces expression of a nucleic acid encoding ANGPTL3. In certain embodiments, antisense nucleic acid is delivered to an organ that expresses a nucleic acid encoding ANGPTL3.

ANGPTL3 is expressed primarily in the liver. Oike, Y. et al. (2005) *TRENDS Mol. Med.* 11(10):473-479. In mice, expression is apparently not affected by short-term fasting. Oike, Y. et al. (2005) *TRENDS Mol. Med.* 11(10):473-479. However, expression is increased with cholesterol feeding and in certain mouse models of obesity and diabetes (e.g., db/db and ob/ob mice), and mice with streptozotocin-induced type I diabetes), suggesting that ANGPTL3 can contribute to the dyslipidemia of diabetes and the metabolic syndrome. Oike, Y. et al. (2005) *TRENDS Mol. Med.* 11(10):473-379. Thus, in certain embodiments, antisense nucleic acid is delivered to the liver. Certain exemplary guidance for the in vivo administration of antisense nucleic acids and the sustained delivery of antisense nucleic acids in vivo, including sustained delivery to specific organs such as the liver, is provided, for example, in Khan et al. (2004) *J. Drug Targeting* 12:393-404.

In certain embodiments, sustained delivery is achieved by administering antisense nucleic acid that is encapsulated or otherwise contained by a biodegradable polymer. For example, in certain embodiments, antisense nucleic acid may be contained within poly(glycolic acid) (PLGA) microspheres (e.g., 0.5-20 µm; 3000 MW). In certain embodiments, the antisense nucleic acid is conjugated to a lipophilic moiety. See Khan et al. (2004) *J. Drug Targeting* 12:393-404.

VI. EXAMPLES

A. Mouse care and dietary studies

Mouse studies were performed according to federal guidelines. Mice were housed at 24° C. on a fixed 12 hour light/12 hour dark cycle and had ad libitum access to water and rodent chow (22% calories from fat) (product no. 5021; Purina, St. Louis, Mo.) as indicated below. Mice referred to below as being in the "fasted state" were deprived of food for 16 hours.

B. In vivo overexpression of human ANGPTL3 in mice cDNA encoding full-length human ANGPTL3 (SEQ ID NO: 6) was inserted into the Ad E1-deleted region of the adenovirus vector pFAD, thereby placing the cDNA under the control of the cytomegalovirus promoter. See Hitt et al., "Construction and propagation of human adenovirus vectors," in *Cell Biology: A Laboratory Handbook* Vol. 1, pp. 500-512 (J. E. Celis, ed., $2^{nd}$ ed. 1998). The resultant construct, Ad5-hAngptl3T, was used to infect CHO cells. Empty Ad5 virus was also used to infect CHO cells as a control. Expression of human ANGPTL3 was confirmed by Western blot of infected CHO cell extracts.

Ad5-hAngptl3T was injected into C57BL/6J mice via the tail vein at the following dosages: $2\times10^9$ vp, $1\times10^9$ vp, $5\times10^8$ vp, $2\times10^8$ vp. Empty Ad5 vector was injected into C57BL/6J mice via the tail vein at $2\times10^9$ vp as a control. There were five mice in each group. Blood samples from adenovirus-infected mice were collected after four days, during which time the mice were fed normally (not fasted). Triglyceride levels in serum were measured using the Cobas Integra 500 (Roche, Basel, Switzerland).

The results are shown in FIG. 8. In that experiment, mice injected with $2\times10^9$ vp or $1\times10^9$ vp of Ad5-hAngptl3T had significantly increased serum triglyceride levels when compared to mice injected with the empty Ad5 vector control.

C. Production and purification of mouse and human ANGPTL3

To express recombinant mouse ANGPTL3, CHO cells were infected with $1.5\times10^{11}$ vp of recombinant adenovirus Ad5-mAngptlT. Ad5-mAngptlT expresses mouse ANGPTL3 with a $His_6$ tag at the C-terminus (a glycine residue is included between ANGPTL3 and the $His_6$ tag), referred to as mANGPTL3T (SEQ ID NO: 2). The medium was changed to serum-free medium (EX-CELL 325-PF CHO medium, 14335, JRH, Lenexa, Kans.) 16-24 hours later. The conditioned medium was harvested and then replaced with fresh serum-free medium every 24-36 hours for a total of 5 harvests.

Conditioned medium (1 L) was loaded onto a 10-12 ml column of Nickel-Chelating Resin (R801-01, Invitrogen, Carlsbad, Calif.). The column was washed with 5 column volumes of wash buffer (10 mM imidazole, 20 mM Tris pH 7.8, 500 mM NaCl). Bound mANGPTL3T was eluted with elution buffer (500 mM imidazole, 20 mM Tris pH 7.8, 500 mM NaCl) and collected in a series of 1.5 ml fractions. The presence of mANGPTL3T in the collected fractions was determined by western blot and simply blue staining. Fractions containing mANGPTL3T were pooled together, aliquoted, and frozen at −70° C.

To express recombinant human ANGPTL3, CHO cells were infected with $1.5 \times 10^{11}$ vp of recombinant adenovirus Ad5-hAngptlT. Ad5-hAngptlT expresses human ANGPTL3 with a $His_6$ tag at the C-terminus (a glycine residue is included between ANGPTL3 and the $His_6$ tag), referred to as hANGPTL3T (SEQ ID NO: 4). hANGPTL3T was expressed and purified as described above for mANGPTL3T.

D. production and purification of rN'-mANGPTL3T and rN'-hANGPTL3T

A polynucleotide sequence encoding amino acids 17 to 240 of mouse ANGPTL3 was cloned into expression vector pET22b(+) (Novagen). That vector encodes an N-terminal pelB leader sequence, as well as a C-terminal His tag. The resulting expression vector is called pET-N'-mANGPTL3T. Following translation of the protein and removal of all but 11 amino acids of the pelB sequence, N'-mANGPTL3T has the sequence shown in SEQ ID NO: 7. That sequence contains 11 amino acids from the pelB sequence, followed by amino acids 17 to 240 of mouse ANGPTL3 (underlined in Table 7), followed by a 2 amino acid linker and the $His_6$ tag.

Similarly, a polynucleotide sequence encoding amino acids 20 to 243 of human ANGPTL3 was cloned into expression vector pET22b(+) (Novagen). That vector encodes an N-terminal pelB leader sequence, as well as a C-terminal His tag. The resulting expression vector is called pET-N'-hANGPTL3T. Following translation of the protein and removal of all but 11 amino acids of the pelB sequence, N'-hANGPTL3T has the sequence shown in SEQ ID NO: 8. That sequence contains 11 amino acids from the pelB sequence, followed by amino acids 20 to 243 of human ANGPTL3 (underlined in Table 7), followed by a 2 amino acid linker and the $His_6$ tag.

N'-mANGPTL3T or N'-hANGPTL3T is expressed and purified from *E. coli* as follows. Ten ml of LB containing 50 μg/ml of chloramphenicol and 100 μg/ml of carbenicillin is inoculated with one colony of *E. coli* transformed with pET-N'-mANGPTL3T. The culture is incubated at 37° C. overnight. The 10 ml culture is then transferred to 500 ml of LB without antibiotics and incubated at 37° C. until the $OD_{600}$ reaches 0.6 (about 2 hours). IPTG is added to a final concentration of 1 mM and the culture is incubated with shaking at 200 rpm at 30° C. for 4 hours. The culture is then placed on ice for 5 minutes. The cells are pelleted by centrifuging at 8000 rpm in a JLA16.25 rotor for 15 minutes. The pellet is then resuspended in 50 ml of lysis buffer (50 mM Tris, pH 7.5, 0.5 M NaCl, 1% Triton X-100, 1× protease inhibitor cocktail (Roche) and 0.25 ml PMSF (0.1 M in isopropanol)). The lysed cells are then centrifuged at 9700 rpm in a JA25.5 rotor for 30 minutes. The supernatant is removed and further clarified by centrifuging it at 28,000 rpm in an SW28 rotor for 30 minutes. Recombinant N'-mANGPTL3T or N'-hANGPTL3T can then be purified from the clarified supernatant using Probond (Ni) chromatography (Invitrogen).

To purify recombinant N'-mANGPTL3T or N'-hANGPTL3T from the insoluble pellet remaining after centrifuging the lysed cells, the pellet is washed with 30 ml lysis buffer and centrifuged at 9700 rpm in a JA25.5 rotor. The wash step is repeated twice, for a total of three washes. Insoluble protein from the pellet is then dissolved in 10 ml of denaturing buffer (50 mM Tris, pH 8.0, 6 M Guanidine HCl). The solution is then centrifuged at 28,000 rpm in a JA25.5 rotor for 30 minutes. The supernatant is then loaded onto a 5 ml Probond resin column. The column is washed with 50 ml of washing buffer (50 mM Tris, pH 8.0, 1 M NaCl, 8 M urea, 15 mM imidazole). Recombinant protein is refolded in the column with a 50 ml gradient going from washing buffer to renaturing buffer (50 mM Tris, pH 8.0, 1 M NaCl, 0.5% Tween 20). The recombinant protein is then eluted with elution buffer (renaturing buffer with 250 mM imidazole). The fractions containing recombinant protein are collected and dialyzed against storage buffer (50 mM Tris, pH 8.0, 100 mM NaCl, 0.2% Tween 20). The purified N'-mANGPTL3T or N'-hANGPTL3T is aliquoted and stored at −70° C.

E. Production and purification of SP1 and SP2-KLH

Purified SP1 (SEQ ID NOS:9 and 10) and SP2-KLH (SEQ ID NO:62) were purchased from Sigma Genosys (The Woodlands, Tex.). The sequence of the SP1 region of ANGPTL3 is the same in both mouse and human. SP2-KLH was made by adding a cysteine to the COOH-terminus of SP1, then conjugating Keyhole Limpet Hemocyanin to the peptide via the cysteine using standard methods known in the art.

F. Generation of monoclonal antibodies against ANGPTL3 in Angptl3 Knockout Mice

Monoclonal antibodies that cross-react with both human and mouse ANGPTL3 were raised in Angptl3 knockout mice using three cohorts of 5-8 mice, each receiving a different series of antigen injections. Cohort 1 was primed with mANGPTL3T (SEQ ID NO: 2), produced and purified as described above. Cohort 1 was also boosted four times with mANGPTL3T. The final boost before harvesting the lymphoid tissue was with mANGPTL3T. Cohort 2 was primed with rN'-hANGPTL3T (SEQ ID NO: 8), produced and purified as described above. Cohort 2 was boosted once with rN'-mANGPTL3T (SEQ ID NO: 7), produced and purified as described above, and then three times with mANGPTL3T (SEQ ID NO: 2). The final boost before harvesting the lymphoid tissue was with hANGPTL3T (SEQ ID NO: 4). Cohort 3 was primed with hANGPTL3T (SEQ ID NO: 4), produced and purified as described above, and then boosted once with hANGPTL3T and then boosted twice with the synthetic peptide SP2-KLH (SEQ ID NO: 62) produced and purified as described above. Two high titer animals from cohort 3 were given a final boost with SP2-KLH (SEQ ID NO: 62) before harvesting lymphoid tissue. The remaining cohort 3 animals (referred to as cohort 4) were boosted four additional times with the synthetic peptide SP2-KLH (SEQ ID NO: 62) produced and purified as described above. The final boost for cohort 4 before harvesting the lymphoid tissue was with SP2-KLH (SEQ ID NO: 62).

Each mouse was primed and boosted as follows. Each mouse was primed with 40 μg of purified antigen in Complete Freund's Adjuvant intraperitoneally. The mice were boosted after two weeks with 30 μg of purified antigen in Incomplete Freud's Adjuvant (IFA) intraperitoneally, and then boosted again after another two weeks with 20 μg purified antigen in IFA intraperitoneally. Alternatively, chitosan-based adjuvants can be used. See, e.g., U.S. Pat. Nos. 5,912,000; 5,965,144; and 5,980,912. One week after the second boost, serum titers were measured by ELISA, as described below, using mANGPTL3 as the antigen-coated plates. Two weeks after the second boost, the mice were boosted with 10 μg purified antigen in IFA intraperitoneally. One week after the third boost, serum titers were again measured by ELISA as above. For cohort 4, intraperitoneal boosting was continued until high titers were achieved. Upon generation of high titers, final boosts were done using either the priming antigen (cohorts 1 and 2) or the boosting antigen (cohorts 3 and 4). The final boost was given about two and a half weeks after the penultimate boost, and was done with 10 μg purified antigen intravenously.

Splenocytes were harvested three days after the final boost from the immunized mice and fused with myeloma cells (NSI) using PEG1500 as a fusion agent. The resulting cell fusion products were diluted into hybridoma medium and seeded into 96-well tissue culture plates. After 1 day, HAT medium was added to the hybridoma cultures. The medium was changed every three or four days as necessary.

After ten to fourteen days of selection and culture, hybridomas were screened by ELISA. The hybridomas from cohort 1 were screened using mANGPTL3T, hANGPTL3T, and N'-hANGPTL3T. The hybridomas from cohort 2 were screened using mANGPTL3T and hANGPTL3T. The hybridomas from cohorts 3 and 4 were screened using hANGPTL3T and synthetic peptide representing the SP1 region of ANGPTL3.

ELISAs were performed as described below.

G. Elisa methods

Antibodies were screened for binding to antigen using ELISA. Antibodies from each cohort were screened for binding to mANGPTL3T, hANGPTL3T, N'-hANGPTL3T, and/or hANGPTL3 SP1 peptide. Ninety-six well Nunc Maxi-Sorp ImmunoPlates™ (Nunc #446612, Roskilde, Denmark) were coated by adding 50 µl per well of a 2.5 µg/ml solution of mANGPTL3T, hANGPTL3T, N'-hANGPTL3T, and/or hANGPTL3 SP1 peptide in coating buffer (BupH™ Carbonate-Bicarbonate Buffer, Pierce #28382, Rockford, Ill.) overnight at 4° C. Coating buffer was removed and the plate was blocked by adding 250 µl per well of blocking buffer (1% Blocker™ BSA, Pierce #37525, in PBS) for two hours at room temperature. 50 µl of hybridoma supernatant (undiluted or diluted in blocking buffer) or isolated anti-ANGPTL3 antibody (undiluted or diluted in blocking buffer) were added to the wells and incubated for at least one hour at room temperature. Wells were washed four times with PBS/Tween 20. 100 µl of diluted (1:5,000 to 1:10,000) HRP-conjugated goat anti-mouse IgG (Pierce #31446) were added to the wells and incubated for one hour at 37° C. Wells were washed six times with PBS/Tween 20. Anti-ANGPTL3 antibody was detected by adding 50 µl of TMB (tetramethyl benzidine) solution (ImmunoPure® TMB Substrate Kit, Pierce #34021) to the wells for 5 to 10 minutes. Plates were read spectrophotometrically at 450 nm using a microplate reader (Molecular Devices, Sunnyvale, Calif.).

H. Epitope mapping of monoclonal antibodies

1. Antibody binding to certain ANGPTL3 peptides

Six antibodies from cohort 1 were tested by antibody capture ELISA for binding to three different 50 amino acid peptides from the N-terminus of mouse ANGPTL3 and to N'-mANGPTL3T. The antibodies tested were designated 1.251.1, 1.132.1, 1.173.2, 1.315.1, 1.424.1, and 1.431.1. Those antibodies were tested for binding to an $S^{17}$-$G^{66}$ peptide (SEQ ID NO: 11), a $D^{42}$-$E^{91}$ peptide (SEQ ID NO: 12), a $Q^{67}$-$M^{116}$ peptide (SEQ ID NO: 13), and N'-mANGPTL3T (SEQ ID NO: 7).

The results of that experiment are shown in Table 2.

None of the tested antibodies bound to the $S^{17}$-$G^{66}$ peptide. Antibodies 1.251.1, 1.173.1, 1.315.1, and 1.424.1 bound to both the $D^{42}$-$E^{91}$ peptide and N'-mANGPTL3T. Antibody 1.173.1 also bound to the $Q^{67}$-$M^{116}$ peptide. Antibodies 1.132.1 and 1.431.1 did not bind to any of the peptides tested or to N'-mANGPTL3T, which suggests that those antibodies bind to an epitope outside of the region between $S^{17}$ and $D^{240}$ of mANGPTL3.

Eight antibodies from cohort 3 were tested by antibody capture ELISA for binding to a synthetic peptide with the sequence of the SP1 region of ANGPTL3 (referred to as ANGPTL3 SP1) EPKSRFAMLDDVKILANGLLQLGHGL (SEQ ID NOS:9 and 10) and full-length HIS-tagged human ANGPTL3T: MFTIKLLLFIVPLVISSRIDQDNSSFD-SLSPEPKSRFAMLDDVKILANGLLQLG HGLKDFVH-KTKGQINDIFQKLNIFDQSFYDLSLQT-SEIKEEEKELRRTTYKLQ VKNEEVKNMSLELNSKLE-SLLEEKILLQQKVKYLEEQLTNLIQNQPETPEHPE VTSLKTFVEKQDN-SIKDLLQTVEDQYKQLNQQHSQIKEIEN-QLRRTSIQEPTE ISLSSKPRAPRTTPFLQLNEIRN-VKHDGIPAECTTIYNRGEHTSGMYAIRPSN SQVFHVYCDVISGSPWTLIQHRIDGSQN-FNETWENYKYGFGRLDGEFWLGL EKIYSIVKQSNYVLRIELED-WKDNKHYIEYSFYLGNHETNYTLHLVAITGNVPN AIPENKDLVFSTWDHKAKGHFNCP-EGYSGGWWWHDECGENNLNGKYNKP RAKSKPER-RRGLSWKSQNGRLYSIKSTKMLIHPTD-SESFEGHHHHHH (SEQ ID NO:4) and full-length human ANGPTL3 (using ANGPTL3T, produced as described above) (SEQ ID NO:3). Unrelated recombinant protein was used as a control.

The results of that experiment are shown in FIG. 9. Antibodies 4.1.1, 4.4.1, 4.8.1, and 4.8.3 bound to ANGPTL3 SP1 better than to full-length ANGPTL3T. Antibodies 4.7.1 and 4.9.1 bound to both ANGPTL3 SP1 and ANGPTL3T. Antibody 4.6.3 bound to full-length ANGPTL3T, but not to ANGPTL3 SP1. Finally, antibody 4.8.2 bound to all proteins tested, including the control protein.

Antibodies from cohort 4 were tested for binding to hANGPTL3T and hANGPTL3 SP1 peptide (data not shown). Antibodies 5.35 and 5.50 bound to both antigens and were selected for further analysis.

2. Alanine-scanning mutagenesis of SP1 peptide

The epitopes for antibodies 41.1, 4.8.3, 4.9.1, 5.35, and 5.50 were further defined using alanine-scanning mutagenesis of the SP1 peptide. The wild-type SP1 peptide has the sequence EPKSRFAMLDDVKILANGLLQLGHGL (SEQ ID NO: 9). A series of 26 mutants was made, in which each of the 26 amino acids of the wild-type SP1 peptide was changed to an alanine, as shown in Table 3:

TABLE 2

Antibody binding to ANGPTL3 peptides

| antibody | mouse ANGPTL3 peptide | | | N'-mANGPTL3T |
|---|---|---|---|---|
| | $S^{17}$-$G^{66}$ | $D^{42}$-$E^{91}$ | $Q^{67}$-$M^{116}$ | |
| 1.251.1 | − | + | − | + |
| 1.132.1 | − | − | − | − |
| 1.173.2 | − | + | + | + |
| 1.315.1 | − | + | − | + |
| 1.424.1 | − | + | − | + |
| 1.431.1 | − | − | − | − |

TABLE 3

Mutant SP1 peptides

| peptide | sequence | SEQ ID NO: |
|---|---|---|
| SP1 | EPKSRFAMLDDVKILANGLLQLGHGL | 9 |
| mutant 1 | APKSRFAMLDDVKILANGLLQLGHGL | 83 |
| mutant 2 | EAKSRFAMLDDVKILANGLLQLGHGL | 84 |
| mutant 3 | EPASRFAMLDDVKILANGLLQLGHGL | 85 |

TABLE 3-continued

Mutant SP1 peptides

| peptide | sequence | SEQ ID NO: |
|---|---|---|
| mutant 4 | EPKARFAMLDDVKILANGLLQLGHGL | 86 |
| mutant 5 | EPKSAFAMLDDVKILANGLLQLGHGL | 87 |
| mutant 6 | EPKSRFAMLDDVKILANGLLQLGHGL | 88 |
| "mutant 7" | EPKSRFAMLDDVKILANGLLQLGHGL | 9 |
| mutant 8 | EPKSRFAALDDVKILANGLLQLGHGL | 89 |
| mutant 9 | EPKSRFAMADDVKILANGLLQLGHGL | 90 |
| mutant 10 | EPKSRFAMLADVKILANGLLQLGHGL | 91 |
| mutant 11 | EPKSRFAMLDAVKILANGLLQLGHGL | 92 |
| mutant 12 | EPKSRFAMLDDAKILANGLLQLGHGL | 93 |
| mutant 13 | EPKSRFAMLDDVAILANGLLQLGHGL | 94 |
| mutant 14 | EPKSRFAMLDDVKALANGLLQLGHGL | 95 |
| mutant 15 | EPKSRFAMLDDVKIAANGLLQLGHGL | 96 |
| "mutant 16" | EPKSRFAMLDDVKALANGLLQLGHGL | 9 |
| mutant 17 | EPKSRFAMLDDVKILAAGLLQLGHGL | 97 |
| mutant 18 | EPKSRFAMLDDVKILANALLQLGHGL | 98 |
| mutant 19 | EPKSRFAMLDDVKILANGALQLGHGL | 99 |
| mutant 20 | EPKSRFAMLDDVKILANGLAQLGHGL | 100 |
| mutant 21 | EPKSRFAMLDDVKILANGLLALGHGL | 101 |
| mutant 22 | EPKSRFAMLDDVKILANGLLQAGHGL | 102 |
| mutant 23 | EPKSRFAMLDDVKILANGLLQLAHGL | 103 |
| mutant 24 | EPKSRFAMLDDVKILANGLLQLGAGL | 104 |
| mutant 25 | EPKSRFAMLDDVKILANGLLQLGHAL | 105 |
| mutant 26 | EPKSRFAMLDDVKILANGLLQLGHGA | 106 |

"Mutant 7" and "Mutant 16" "replaced" an alanine in the wild-type sequence with an alanine. Those "mutants" therefore had the wild-type SP1 peptide sequence and were not made.

Antibodies 4.7.1, 4.8.3, 4.9.1, 5.35, and 5.50 were tested by antibody capture ELISA for binding to the synthetic peptides shown in Table 3 (except for the "Mutant 7" and "Mutant 16" peptides), as follows. Alanine mutants were generated using injected for each antibody. Fed and fasted serum levels of triglycerides and cholesterol were measured after four days.

Figure 1:
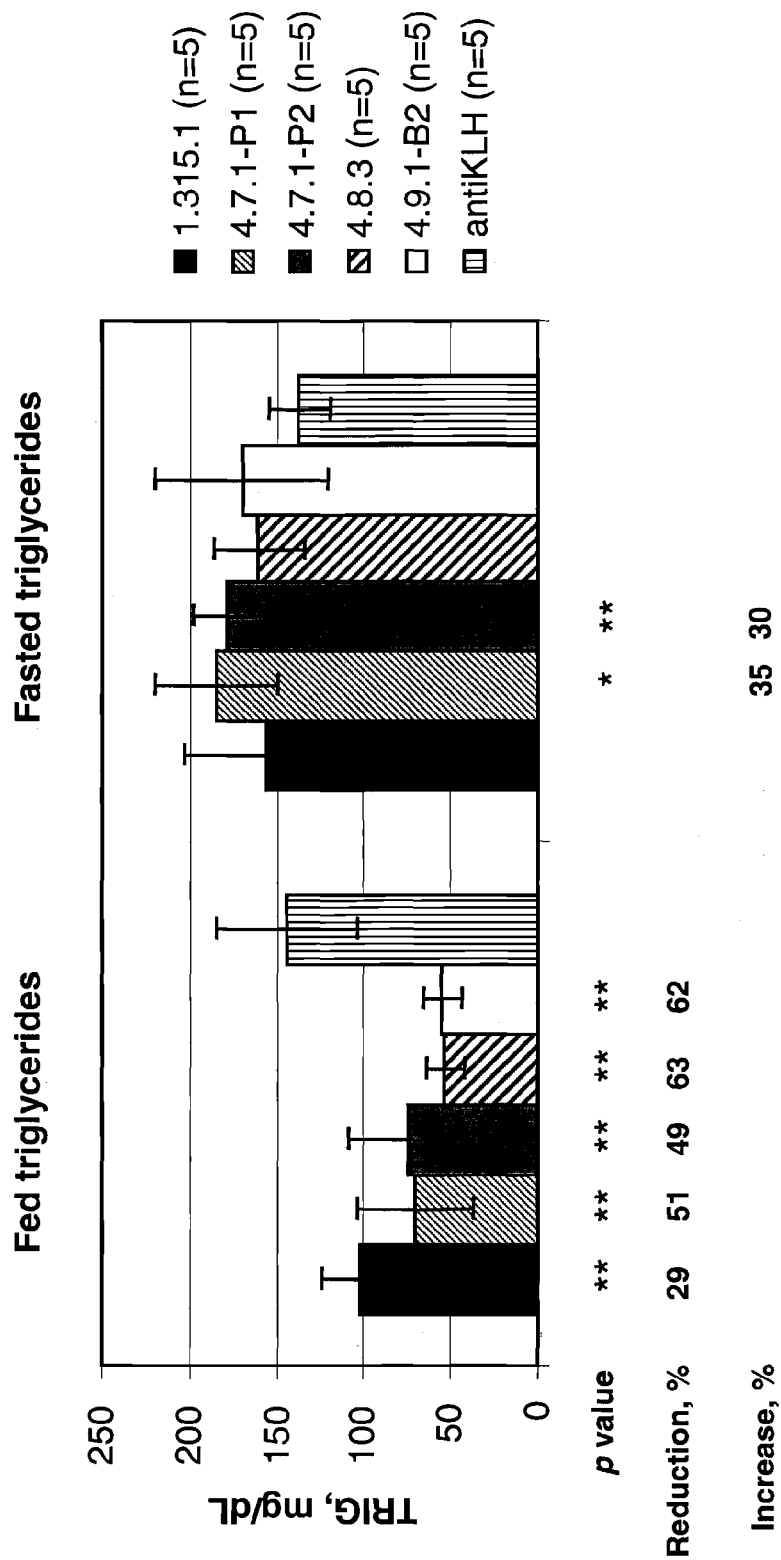
FIG. 1 shows fed and fasted serum triglyceride levels in mice 4 days after injection with antibodies 1.315.1, 4.7.1, 4.8.3, 4.9.1, and control antibody anti-KLH, as described in Example J.
Figure 2:
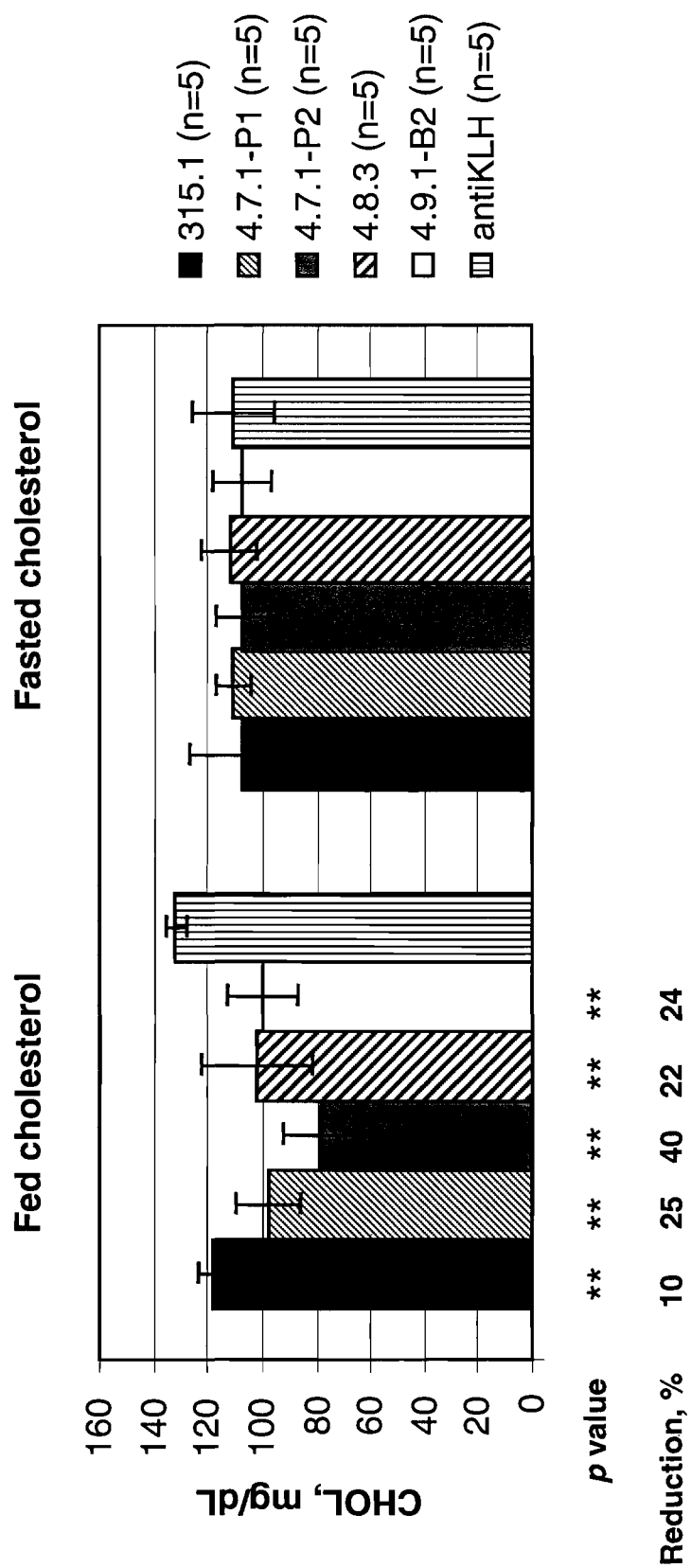
FIG. 2 shows fed and fasted serum cholesterol levels in mice 4 days after injection with antibodies 1.315.1, 4.7.1, 4.8.3, 4.9.1, and control antibody anti-KLH, as described in Example J.
Figure 3:
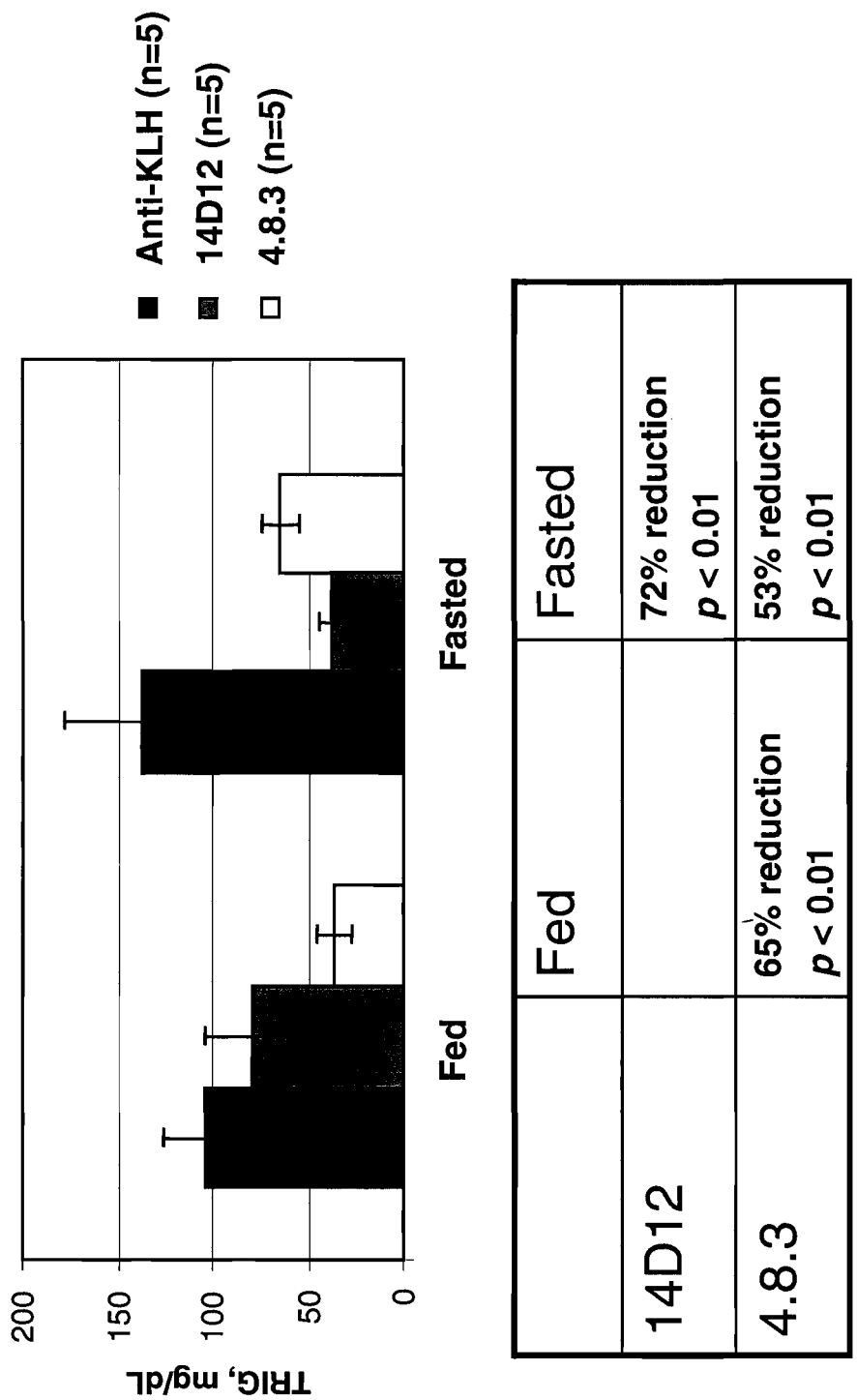
FIG. 3 shows fed and fasted serum triglyceride levels in mice 4 days after injection with anti-ANGPTL3 antibody 4.8.3, anti-ANGPTL4 antibody 14D12, and control antibody anti-KLH, as described in Example J.
Figure 4:
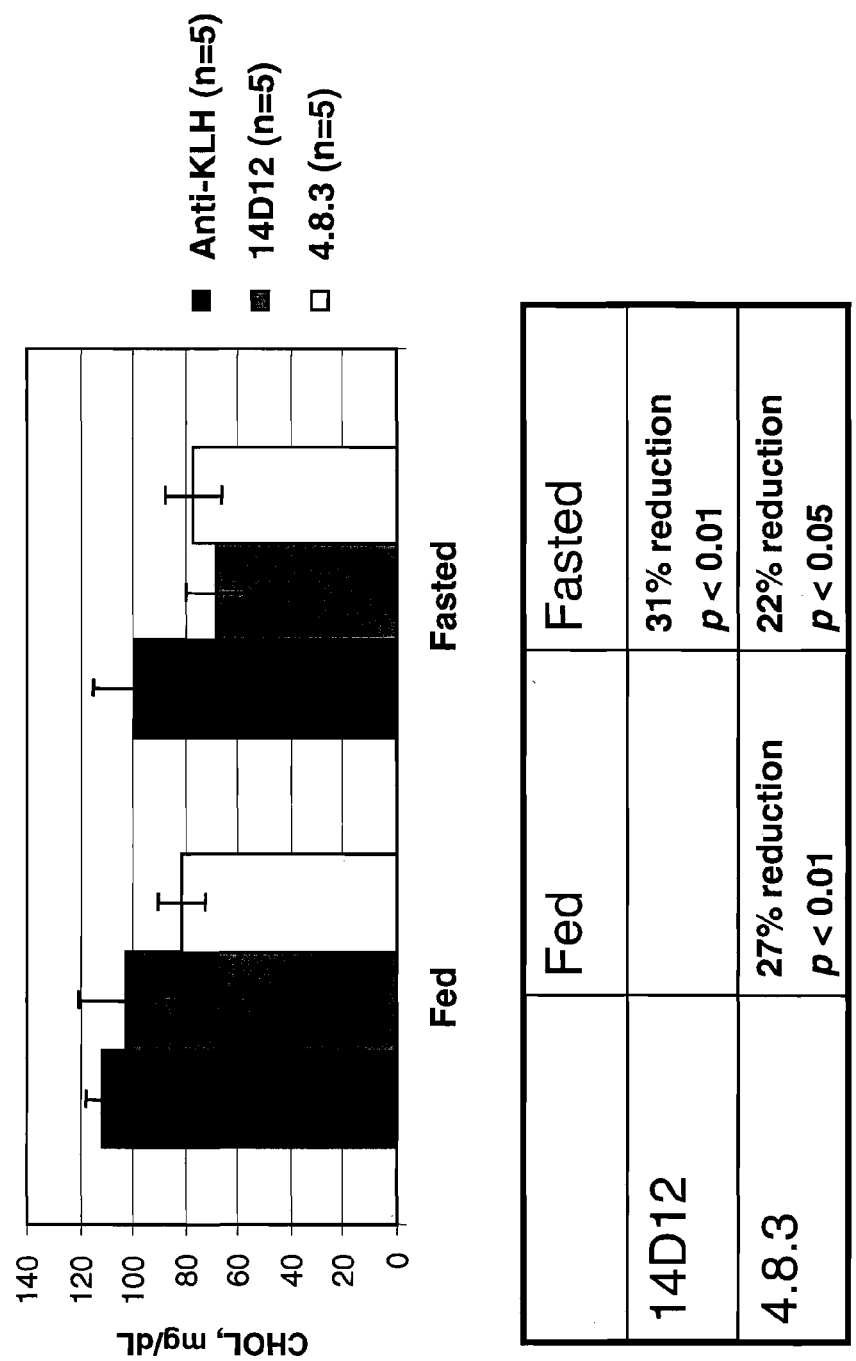
FIG. 4 shows fed and fasted serum cholesterol levels in mice 4 days after injection with anti-ANGPTL3 antibody 4.8.3, anti-ANGPTL4 antibody 14D12, and control antibody anti-KLH, as described in Example J.

The results of that experiment are shown in FIGS. 3 and 4. FIG. 3 shows fed and fasted serum triglyceride levels in mice administered anti-ANGPTL3 antibody 4.8.3, anti-ANGPTL4 antibody 14D12, or anti-KLH antibody. In that experiment, 4.8.3 reduced serum triglyceride levels by a statistically significant extent in both fed and fasted mice. Antibody 14D12, on the other hand, reduced serum triglyceride levels by a statistically significant extent only in fasted mice in that experiment.

FIG. 4 shows fed and fasted serum cholesterol levels in mice administered anti-ANGPTL3 antibody 4.8.3, anti-ANGPTL4 antibody 14D12, or anti-KLH antibody. In that experiment, 4.8.3 reduced serum cholesterol levels by a statistically significant extent in both fed and fasted mice. Antibody 14D12, on the other hand, reduced serum cholesterol levels by a statistically significant extent only in fasted mice in that experiment.

In the third experiment, 8 week old C57 albino mice fed a standard diet ("chow-fed" mice) were injected with 30 µg of a monoclonal antibody in a volume of 10 µl per gram of body weight. The anti-ANGPTL3 antibodies tested in that experiment were 4.7.1, 4.8.3, and 4.9.1. An anti-KLH antibody was administered as a control. In addition, anti-ANGPTL4 antibody 14D12 was tested for comparison. Ten mice were injected for each antibody. Fed and fasted serum levels of triglycerides and cholesterol were measured after four days.

Figure 5:
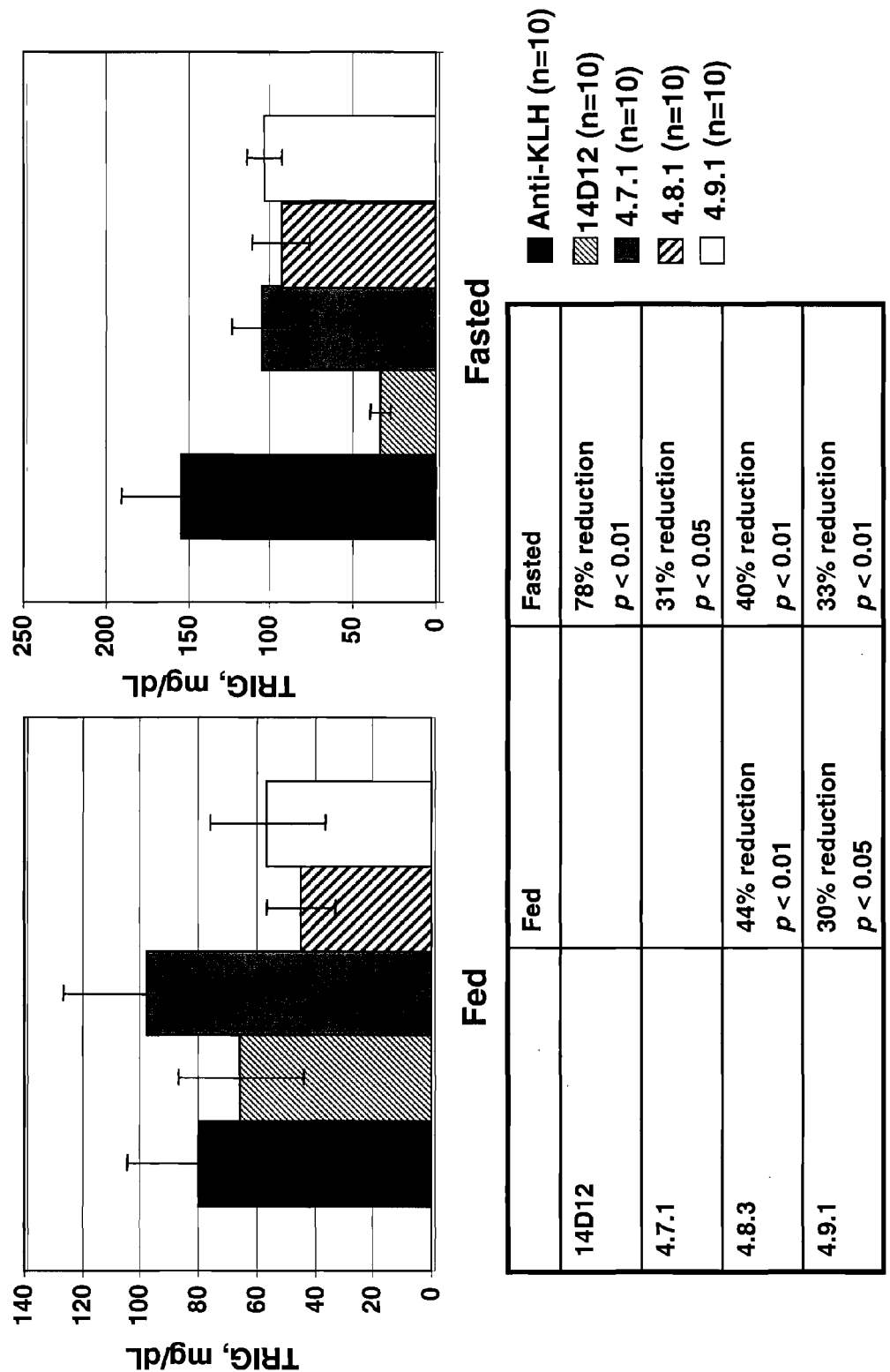
FIG. 5 shows fed and fasted serum triglyceride levels in mice 4 days after injection with anti-ANGPTL3 antibodies 4.7.1, 4.8.3, 4.9.1, anti-ANGPTL4 antibody 14D12, and control antibody anti-KLH, as described in Example J.
Figure 6:
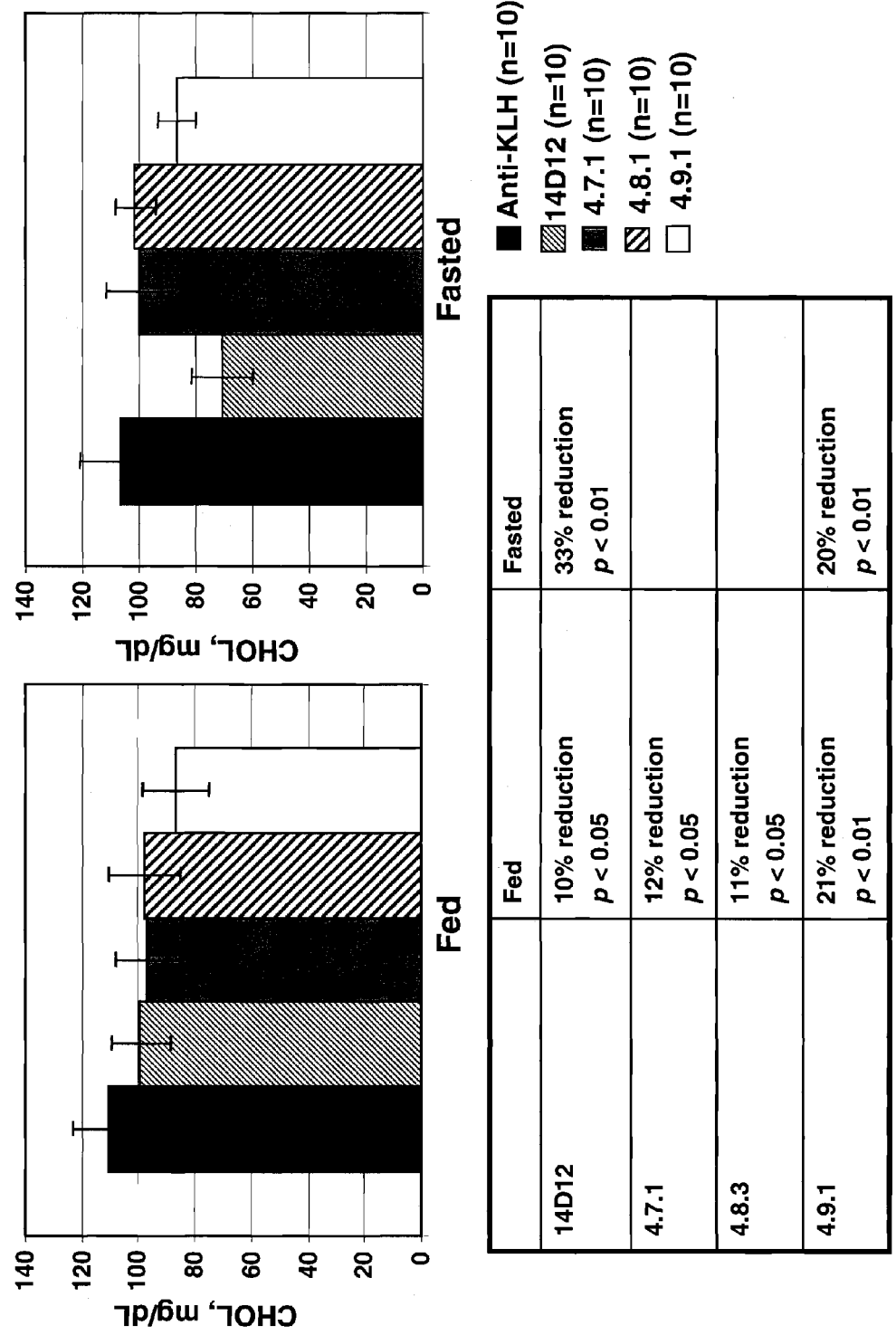
FIG. 6 shows fed and fasted serum cholesterol levels in mice 4 days after injection with anti-ANGPTL3 antibodies 4.7.1, 4.8.3, 4.9.1, anti-ANGPTL4 antibody 14D12, and control antibody anti-KLH, as described in Example J.

The results of that experiment are shown in FIGS. 5 and 6. FIG. 5 shows fed and fasted triglyceride levels after four days in mice administered 4.7.1, 4.8.3, 4.9.1, 14D12, and anti-KLH. Anti-ANGPTL3 antibodies 4.8.3 and 4.9.1 caused a statistically significant decrease in serum triglyceride levels in mice in the fed state in that experiment. The failure of antibody 4.7.1 to reduce triglycerides in the fed state may be due, in part, to it being an IgG2b antibody, which has a predicted half-life in serum of only 3 to 3.5 days. Anti-ANGPTL3 antibodies 4.7.1, 4.8.3, and 4.9.1, as well as anti-ANGPTL4 antibody 14D12 caused a decrease in serum triglyceride levels in mice in the fasted state in that experiment.

FIG. 6 shows fed and fasted cholesterol levels after four days in mice administered 4.7.1, 4.8.3, 4.9.1, 14D12, and anti-KLH. Anti-ANGPTL3 antibodies 4.7.1, 4.8.3, and 4.9.1, as well as anti-ANGPTL4 antibody 14D12 caused a decrease in serum cholesterol levels in mice in the fed state in that experiment. In that experiment, however, only anti-ANGPTL3 antibody 4.9.1 and anti-ANGPTL4 antibody 14 D12 caused a decrease in serum cholesterol levels in mice in the fasted state.

In the fourth experiment, 8 week old C57 albino mice fed a standard diet ("chow-fed" mice) were injected with 30 µg of a monoclonal antibody in a volume of 10 µl per gram of body weight. The anti-ANGPTL3 antibodies tested in that experiment were 1.125.1, 1.132.1, 1.173.2, 1.315.1, 1.424.1, and 1.431.1. An anti-KLH antibody was administered as a control. There were five mice in each group. Fed and fasted serum levels of triglycerides were measured after four days and after 8 days.

The results of that experiment are shown in FIG. 7. In that experiment, 1.315.1 reduced serum triglycerides by a statically significant extent after both 4 days and 8 days.

In a fifth experiment, 8 to 10 week old C57 albino mice fed a standard diet ("chow-fed" mice) were injected with 0 µg, 3 µg, 10 µg, 30 µg, or 90 µg of a monoclonal antibody in a volume of 10 µl per gram of body weight. The anti-ANGPTL3 antibodies tested in that experiment were 5.35 and 5.50. Five mice were injected for each antibody at each dose. Fed serum levels of triglycerides and cholesterol were measured after four days and after seven days.

The results of that experiment are shown in FIGS. 15 and 16. FIG. 15 shows serum triglycerides after four and seven days in mice injected with various amounts of antibodies 5.35 and 5.50. In that experiment, both antibodies 5.35 and 5.50 reduced serum triglycerides after four days in mice injected with 30 mg/kg or 90 mg/kg of antibody. Antibody 5.50 also reduced serum triglycerides after four days in mice injected with 3 mg/kg or 10 mg/kg of antibody in that experiment. Serum triglycerides were still reduced after seven days in mice injected with 10 mg/kg, 30 mg/kg, or 90 mg/kg of antibody 5.50 in that experiment, while only mice injected with 90 mg/kg of antibody 5.35 continued to have reduced serum triglycerides after seven days.

FIG. 16 shows serum cholesterol levels in mice injected with various amounts of antibodies 5.35 and 5.50. In that experiment, mice injected with 30 mg/kg or 90 mg/kg of antibody 5.35, or 10 mg/kg, 30 mg/kg, or 90 mg/kg of antibody 5.50 had reduced serum cholesterol levels after four days. Mice injected with 90 mg/kg of antibody 5.35 or 90 mg/kg of antibody 5.50 continued to have reduced serum cholesterol levels after seven days.

K. Administration Of monoclonal antibodies against ANGPTL3 in ApoE knockout mice ApoE knockout mice have been found to develop spontaneous hypercholesterolemia. See, e.g., Piedrahita et al. (1992) *Proc. Natl. Acad. Sci. USA* 89(10):4471-5; and Zhang et al. (1992) *Science* 258(5081):468-71. To determine if certain monoclonal antibodies against ANGPTL3 can reduce serum cholesterol and triglyceride levels in ApoE knockout mice, the following experiment was performed. Three groups of eight 14-week old ApoE knockout mice (Taconic Animal Models, strain B6.129P2-Apoe$^{tm1Unc}$ N11) were injected with 30 mg/kg anti-KLH, 30 mg/kg antibody 5.35, or 30 mg/kg antibody 5.50 intraperitoneally. Each mouse received one injection on day 0 and one injection on day 4. All mice were fed a standard diet ("chow-fed"). Fed serum triglyceride levels and fed cholesterol levels were determined in each mouse at day 0 (pre-injection), day 4, day 8, and day 12.

The results of that experiment are shown in FIG. 19. Antibody 5.35 reduced serum triglyceride levels by 36% by day 4. That reduction persisted through day 8, but disappeared by day 12. Antibody 5.50 reduced serum triglyceride levels by 60% by day 4. That reduction persisted through day 8, and serum triglycerides remained significantly reduced through day 12.

Antibody 5.35 reduced serum cholesterol levels by 17%, although that reduction was not achieved until day 8 in that experiment, and the reduction diminished somewhat by day 12. Antibody 5.50 reduced serum cholesterol levels by day 4, and continued to reduce the serum cholesterol levels through day 8 and day 12, to a total reduction of 30% at the time that experiment was ended.

Those results showed that antibodies 5.35 and 5.50 reduced both serum triglyceride levels and serum cholesterol levels in ApoE mice. Antibody 5.50 was more effective at reducing both serum triglyceride levels and serum cholesterol levels in that experiment, which may be due to the longer half-life of that antibody.

L. In vitro administration of monoclonal antibodies to ANGPTL3

The effect of mouse monoclonal anti-ANGPTL3 on LPL activity was tested using an in vitro assay. To obtain LPL-conditioned media, HEK293F cells (the FreeStyle™ 293 Expression System) (Invitrogen, Carlsbad, Calif.) were transfected with an LPL expression vector comprising DNA encoding LPL with a C-terminal FLAG tag in the IRES puro plasmid (Clontech, Mountain View, Calif.).

Transformed cells were grown in selection medium (FreeStyle™ 293 System medium (GIBCO BRL, Gaithersburg, Md.) supplemented with 1× Penicillin-Streptomycin-Glutamine (Invitrogen, Carlsbad, Calif.) and 2.4 µg/ml of puromycin). Cells were enumerated and pelleted by centrifugation. The resulting cell pellet was resuspended in fresh FreeStyle™ 293 medium containing 1× GPS, without puromycin) at a concentration of 1×10$^6$ cells/ml. Following a 48 hour incubation, conditioned medium containing LPL was harvested from the cells, distributed in 5 ml aliquots and then frozen at −70° C. until used.

LPL activity in conditioned medium was assayed by adding 200 mg/dL Intralipid® (Pharmacia & Upjohn), 12 mM Glucose, 5 units/ml heparin and 200 µl 5% mouse serum (as a source of Apo C-II) to aliquots of conditioned medium. That medium was then incubated at 37° C. Samples were harvested at 2 hours, 4 hours, and 6 hours and frozen immediately at −70° C. until assays were performed. LPL conditioned medium was assayed for LPL activity by measuring FFA levels using undiluted conditioned medium and dilutions of 1:2, 1:4, 1:8, 1:16, and 1:32. The FFA levels were determined at 2 hours, 4 hours and 6 hour using a Wako FFA kit (Wako Chemical USA, Inc., Richmond, Va.).

The ability of monoclonal antibodies to neutralize ANGPTL3 activity in an in vitro assay for LPL activity was also determined. The in vitro assay for LPL activity measures FFA levels using a Wako FFA kit (Wako Chemical USA, Inc., Richmond, Va.). Separate LPL activity assays were conducted in the presence of 25 nM mouse ANGPTL3 and four concentrations (0.8 µg/ml, 2 µg/ml, 10 µg/ml and 50 µg/ml) of each of 5 monoclonal antibodies (antibodies 4.9.1, 4.8.3, 1.315.1, 4.7.1, and 1.173.2). The results are shown in FIG. 12. For each antibody, neutralizing activity is demonstrated by the antibody's ability to increase LPL activity, i.e., to "rescue" LPL from inhibition by ANGPTL3. Rescuing activity was determined as the percentage increase in LPL activity in the presence of both ANGPTL3 and anti-ANGPTL3 antibody relative to LPL activity in the presence of ANGPTL3 alone. Four antibodies (4.9.1, 4.8.3, 1.315.1 and 4.7.1) were able to rescue LPL activity by over 50% depending on their concentration. This result indicated that those antibodies were able to rescue LPL activity by neutralizing ANGPTL3 activity. In contrast, antibody 1.173.2 did not demonstrate significant rescue of LPL activity and as such served as an internal negative control.

M. Binding affinity of monoclonal antibodies against ANGPTL3

The affinity constants of antibodies 4.7.1, 4.8.3, and 4.9.1 for N'-hANGPTL3T and hANGPTL3T and the affinity constants of antibodies 4.7.1, 4.9.1, 5.35, and 5.50 to the SP1 peptide were determined using a BIACORE® 3000 system (GE Healthcare, Uppsala, Sweden). The BIACORE® 3000 is a real-time biomolecular analysis system for detecting and quantifying protein-protein interactions using surface plasmon resonance technology. The following affinity constants were determined according to the manufacturer's instructions for the BIACORE® 3000 system: equilibrium dissociation constant ($K_D$), association rate constant ($k_{on}$), and dissociation rate constant ($k_{off}$).

Affinity constants of the 4.7.1, 4.8.3, and 4.9.1 antibodies for N'-hANGPTL3T and hANGPTL3T protein antigens were each determined as follows. The BIACORE CM5 chip surface was coated with a protein antigen by coupling either 10 µg/ml of N'-hANGPTL3T or 20 µg/ml of hANGPTL3T to the chip surface using an Amine Coupling Kit (Product No.: BR-1000-50, GE Healthcare, Uppsala Sweden). The association and dissociation phases, which are used to determine the $k_{on}$ and $k_{off}$ constants, were generated by first injecting a Fab fragment of the antibody (generated using a Fab Preparation Kit (Product No.: 44885, Pierce, Rockford, Ill. 61105) according to the manufacturer's instructions) into the BIACORE® 3000 system having a coated chip surface for 2 minutes at a flow rate of 30 µl/min. The concentrations of Fab fragment tested were 200 nM, 100 nM, 50 nM, 25 nM, 12.5 nM, 6.25 nM, 3.125 nM, 1.5 625 nM, 0.78125 nM, and 0 nM. The injection phase was used to determine the association rate constant, or $k_{on}$. Following each injection, the Fab fragment was dissociated from the protein antigen by flowing BIACORE HBS-EP buffer (Product No.: BR-1001-88, GE Healthcare, Uppsala Sweden) for 5 minutes over the antigen-Fab complex on the BIACORE CM5 chip surface. This dissociation phase was used to determine the dissociation rate constant, or $k_{off}$. Prior to the next injection, the BIACORE chip surface was regenerated by injecting 10 mM HCl at a flow rate of 100 µl/min for 30 seconds. BIACORE sensograms for data analysis were generated by subtracting the non-specific binding profile of a reference surface (immobilized with equivalent levels of unrelated proteins) from the Fab-specific binding profiles of 4.7.1, 4.8.3, and 4.9.1 surfaces. The affinity parameters, including the $K_D$, $k_{on}$, and $k_{off}$ values, were determined by globally fitting the association and dissociation data sets to 1:1 binding model with mass transfer correction using BIAevalution Software Version 3.0 (GE Healthcare, Uppsala Sweden).

Affinity constants of the 4.7.1, 4.9.1, 5.35, and 5.50 antibodies for the SP1 peptide antigen were each determined as follows. The BIACORE CM5 chip surface was coated with an anti-mouse IgG $F_c$ by coupling 90 µg/ml of ImmunoPure Goat Anti-Mouse IgG $F_c$ (Product No.: 31170, Pierce, Rockford, Ill. 61105) to the chip surface using an Amine Coupling Kit (Product No.: BR-1000-50, GE Healthcare, Uppsala Sweden). The antibody was then captured on the anti-mouse IgG $F_c$ BIACORE chip surface by injecting the antibody at a flow rate of 10 µl/min for 30 sec. The association and dissociation phases, which are used to determine $k_{on}$ and $k_{off}$ constants, were generated by first injecting the SP1 peptide into the BIACORE® 3000 system having an antibody-coated chip surface for 2 minutes at a flow rate of 30 µl/min. The concentrations of SP1 peptide tested were 200 nM, 100 nM, 50 nM, 25 nM, 12.5 nM, 6.25 nM, 3.125 nM, 1.5 625 nM, 0.78125 nM, and 0 nM. The injection phase was used to determine the association rate constant, or $k_{on}$. Following each injection, the SP1 peptide was dissociated from the antibody by flowing BIACORE HBS-EP buffer (Product No.: BR-1001-88, GE Healthcare, Uppsala Sweden) for 5 minutes over the peptide-antibody complex on the BIACORE CM5 chip surface. This dissociation phase was used to determine the dissociation rate constant, or $k_{off}$. Prior to the next injection, the BIACORE chip surface was regenerated by injecting 10 mM HCl at a flow rate of 100 µl/min for 30 seconds. BIACORE sensograms for data analysis were generated by subtracting the non-specific binding profile of a reference surface (capturing equivalent levels of unrelated mouse IgG) from the antigen-specific binding profiles of the 4.7.1, 4.9.1, 5.35, and 5.50 surfaces. The affinity parameters, including the $K_D$, $K_{on}$, and $k_{off}$ values, were determined by globally fitting the association and dissociation data sets to 1:1 binding model with mass transfer correction using BIAevalution Software Version 3.0 (GE Healthcare, Uppsala Sweden).

The results of that experiment are shown in Tables 4, 5, and 6. Each antibody was tested in duplicate, and the results for each experiment are shown.

TABLE 4

Antibody affinities for N'-hANGPTL3T.

| Antibody | $K_D$ (nM) | $k_{on}$ (M$^{-1}$sec$^{-1}$) | $k_{off}$(sec$^{-1}$) |
|---|---|---|---|
| 4.7.1 | 49.5 | $1.85 \times 10^5$ | $9.15 \times 10^{-3}$ |
| 4.7.1 | 77.5 | $1.16 \times 10^5$ | $8.99 \times 10^{-3}$ |
| 4.8.3 | 210 | $9.00 \times 10^4$ | $1.90 \times 10^{-2}$ |
| 4.8.3 | 251 | $1.09 \times 10^5$ | $2.75 \times 10^{-2}$ |
| 4.9.1 | 45.4 | $1.31 \times 10^5$ | $5.93 \times 10^{-3}$ |
| 4.9.1 | 55 | $1.33 \times 10^5$ | $7.34 \times 10^{-3}$ |

TABLE 5

Antibody affinities for hANGPTL3T.

| Antibody | $K_D$ (nM) | $k_{on}$ (M$^{-1}$sec$^{-1}$) | $k_{off}$(sec$^{-1}$) |
|---|---|---|---|
| 4.7.1 | 45.3 | $1.76 \times 10^5$ | $7.96 \times 10^{-3}$ |
| 4.7.1 | 117 | $8.12 \times 10^4$ | $9.53 \times 10^{-3}$ |
| 4.8.3 | 970 | $2.23 \times 10^4$ | $2.16 \times 10^{-2}$ |
| 4.8.3 | 450 | $6.00 \times 10^4$ | $2.73 \times 10^{-2}$ |
| 4.9.1 | 48.1 | $1.29 \times 10^5$ | $6.22 \times 10^{-3}$ |
| 4.9.1 | 45.2 | $1.72 \times 10^5$ | $7.77 \times 10^{-3}$ |

TABLE 6

Antibody affinities for SP1 peptide.

| Antibody | $K_D$ (nM) | $k_{on}$ (M$^{-1}$sec$^{-1}$) | $k_{off}$(sec$^{-1}$) |
|---|---|---|---|
| 4.7.1 | 26.1 | $2.09 \times 10^5$ | $5.46 \times 10^{-3}$ |
| 4.9.1 | 46.1 | $1.69 \times 10^5$ | $7.78 \times 10^{-3}$ |
| 5.35 | 1.80 | $8.35 \times 10^5$ | $1.5 \times 10^{-3}$ |
| 5.50 | 1.78 | $1.08 \times 10^6$ | $1.93 \times 10^{-3}$ |

N. In vivo pharmacokinetics of certain monoclonal antibodies Against ANGPTL3

To determine the pharmacokinetics of these antibodies (antibodies 4.7.1, 4.8.3, and 4.9.1) in vivo, each was administered separately to four different mice by intraperitoneal injection, at a dose of 30 mg per kg. At the time points indicated in FIG. 13, the mice were bled and serum was obtained. The levels of anti-ANGPTL3 antibody present in the serum was determined by comparing titers determined by antibody capture ELISA to a standard curve established using serial dilutions of the same antibody that was injected into the mouse in an antibody capture ELISA. The antibody capture ELISAs were performed as described in Example G. The results can be seen in FIG. 13.

To determine the pharmacokinetics of antibodies 5.35 and 5.50 in vivo, antibody levels were determined in the mice described in Example J, fifth experiment, at 4 days, 7 days, and 12 days after injection. The levels of anti-ANGPTL3 antibody present in the serum was determined by antibody capture ELISA using recombinant human ANGPTL3-coated plates. The concentration of antibody in the serum was determined by comparing to a standard curve established using serial dilutions of the same antibody that was injected into the mouse in an antibody capture ELISA. The ELISAs were performed as described in Example G.

The results of that experiment are shown in FIG. 17. In that experiment, antibody 5.50 had a longer half-life in vivo than antibody 5.35. The longer half-life correlated with the increased efficacy in vivo of antibody 5.50 compared to antibody 5.35 in the experiment discussed in Example J, and as shown in FIGS. 15 and 16.

The pharmacokinetics of antibodies 4.7.1, 4.9.1, 5.35, and 5.50 in C57 mice after a single injection of 30 mg/kg antibody is shown in FIG. 18. The antibody concentration was determined by antibody capture ELISA, performed as described in Example G. The concentration of antibody in the serum was determined by comparing to a standard curve established using serial dilutions of the same antibody that had been injected into the mouse in an antibody capture ELISA. In that experiment, antibodies 5.50 and 4.9.1 had approximately equivalent half-lives. In addition, the half-lives of antibodies 5.50 and 4.9.1 were longer than the half-lives of antibodies 5.35 and 4.7.1, which were approximately equivalent to each other in that experiment. Furthermore, the Cmax of antibodies 5.35 and 5.50 were approximately equivalent, and were greater than the Cmax of antibody 4.9.1, which in turn was greater than the Cmax of antibody 4.7.1, in that experiment.

O. Sequences of certain monoclonal antibodies against ANGPTL3

The heavy chain and light chain variable regions of antibodies 4.7.1, 4.8.3, 4.9.1, 5.35, and 5.50 were determined. The heavy chain variable region of antibody 4.7.1 is shown in SEQ ID NO: 19 (with the N-terminal signal peptide) and in SEQ ID NO: 20 (without the N-terminal signal peptide). The light chain variable region of antibody 4.7.1 is shown in SEQ ID NO: 27 (with the N-terminal signal peptide) and in SEQ ID NO: 28 (without the N-terminal signal peptide). The heavy chain variable region of antibody 4.8.3 is shown in SEQ ID NO: 21 (with the N-terminal signal peptide) and in SEQ ID NO: 22 (without the N-terminal signal peptide). The light chain variable region of antibody 4.83 is shown in SEQ ID NO: 29 (with the N-terminal signal peptide) and in SEQ ID NO: 30 (without the N-terminal signal peptide). The heavy chain variable region of antibody 4.9.1 is shown in SEQ ID NO: 23 (with the N-terminal signal peptide) and in SEQ ID NO: 24 (without the N-terminal signal peptide). The light chain variable region of antibody 4.9.1 is shown in SEQ ID NO: 31 (with the N-terminal signal peptide) and in SEQ ID NO: 32 (without the N-terminal signal peptide). The heavy chain variable region of antibody 5.35 is shown in SEQ ID NO: 63 (with the N-terminal signal peptide) and in SEQ ID NO: 64 (without the N-terminal signal peptide). The light chain variable region of antibody 5.35 is shown in SEQ ID NO: 67 (with the N-terminal signal peptide) and in SEQ ID NO: 68 (without the N-terminal signal peptide). The heavy chain variable region of antibody 5.50 is shown in SEQ ID NO: 65 (with the N-terminal signal peptide) and in SEQ ID NO: 66 (without the N-terminal signal peptide). The light chain variable region of antibody 5.50 is shown in SEQ ID NO: 69 (with the N-terminal signal peptide) and in SEQ ID NO: 70 (without the N-terminal signal peptide).

An alignment of the heavy chain variable regions of antibodies 4.7.1, 4.8.3, and 4.9.1 is shown in FIG. 10. The consensus sequence for the heavy chain variable regions is also shown (SEQ ID NO: 25). The consensus sequence for the heavy chain variable regions without the signal peptide is shown in Table 7 (SEQ ID NO: 26).

An alignment of the light chain variable regions of antibodies 4.7.1, 4.8.3, and 4.9.1 is shown in FIG. 11. The consensus sequence for the light chain variable regions is also shown (SEQ ID NO: 33). The consensus sequence for the light chain variable regions without the signal peptide is shown in Table 7 (SEQ ID NO: 34).

P. Humanization of certain monoclonal antibodies against ANGPTL3

The following protocol describes humanization of antibody 4.7.1. Antibodies 4.8.3, 4.9.1, 5.35, 5.50, and 1.315.1 can be humanized by the same method. The humanized version of antibody 4.7.1 is referred to as "hu4.7.1." The humanized versions of antibodies 4.8.3, 4.9.1, 5.35, 5.50, and 1.315.1, are referred to as "hu4.8.3," "hu4.9.1," "hu5.35," "hu5.50," and "hu1.315.1," respectively.

Human framework regions for each of the heavy chain and light chain are selected from a set of family-specific consensus human framework regions based on their homology to the mouse framework regions present in antibody 4.7.1. The selected human framework regions are diversified at specific amino acid positions to reflect framework diversity within the chosen family of V-genes. Polynucleotides encoding CDR1, CDR2, and CDR3 of the heavy chain of antibody 4.7.1 are cloned into the library of polynucleotides that encode the diversified human framework regions for the heavy chain. The resulting library is referred to as a humanized 4.7.1 heavy chain variable region library. Polynucleotides encoding CDR1, CDR2, and CDR3 of the light chain of antibody 4.7.1 are cloned into the library of polynucleotides that encode the diversified human framework regions for the light chain. The resulting library is referred to as a humanized 4.7.1 light chain variable region library. The humanized 4.7.1 heavy chain variable region library and the humanized 4.7.1 light chain variable region library are cloned into a phage display vector in a single chain Fv (scFv) format.

The scFv phage display library is then screened against the target antigen, e.g., human ANGPTL3, through 2-3 rounds of binding to select for high affinity scFvs. The scFvs are then expressed in soluble form and tested for target affinity and/or in vitro neutralizing potency. The heavy chain variable region and light chain variable region of the scFvs selected for suitable affinity and potency are then expressed as full-length IgGs or as scFv-CL-PEG (CL is the human constant light chain) and tested for in vivo activity, e.g., reduction in serum triglycerides and/or serum cholesterol in mice. PEG is attached through a cysteine on the CL group.

Q. Affinity maturation of certain monoclonal antibodies against ANGPTL3

The following protocol describes affinity maturation of antibody 4.7.1. Affinity maturation of antibodies 4.8.3, 4.9.1, 5.35, 5.50, and 1.315.1 can be carried out using the same method. Similarly, affinity maturation of hu4.7.1, hu4.8.3, hu4.9.1, hu5.35, hu5.50, and hu1.315.1 can be carried out using the same method.

A polynucleotide encoding the heavy chain of antibody 4.7.1 is subjected to random mutagenesis, e.g., using error-prone PCR. Error-prone PCR was performed using the GeneMorph® II Random Mutagenesis Kit (Stratagene, La Jolla, Calif.) according to the manufacturer's instructions.

A polynucleotide encoding the light chain of antibody 4.7.1 is also subjected to random mutagenesis, e.g., using error-prone PCR. Error-prone PCR was performed using the GeneMorph® II Random Mutagenesis Kit (Stratagene, La Jolla, Calif.) according to the manufacturer's instructions.

The randomly mutated heavy chain polynucleotide and the randomly mutated light chain polynucleotide are cloned into a phage display vector in a single chain Fv (scFv) format.

The scFv phage display library is then screened against the target antigen, e.g., human ANGPTL3, through 2-3 rounds of binding to select for high affinity scFvs. The scFvs are then expressed in soluble form and tested for target affinity and/or in vitro neutralizing potency. The heavy chain variable region and light chain variable region of the scFvs selected for suitable affinity and potency are then expressed as full-length IgGs or as scFv-CL-PEG, and tested for in vivo activity, e.g., reduction in serum triglycerides and/or serum cholesterol in mice.

The selected affinity matured antibodies can then be humanized as described above in Example P, if not already humanized.

While the above examples describe, inter alia, certain neutralizing monoclonal antibodies against mouse ANGPTL3 and the in vivo effects of those antibodies in mice, one skilled in the art would readily recognize that neutralizing monoclonal antibodies against human ANGPTL3 may be generated, and such antibodies would have the same or similar in vivo effects in humans. That conclusion is based, in part, on the observation that human and mouse ANGPTL3 are evolutionarily conserved proteins that share structural and functional features. Conklin, D., et al. (1999) *Genomics* 62:477-482. For example, human and mouse ANGPTL3 share about 76% amino acid sequence identity. Human and mouse ANGPTL3 also share common secondary structural elements, e.g., an N-terminal coiled-coil domain and a C-terminal fibrinogen-like domain. Furthermore, human ANGPTL3 has a similar function as mouse ANGPTL3, as demonstrated by the ability of human ANGPTL3 to raise serum lipid levels when overexpressed in mice. Koishi et al. (2002) *Nat. Genet.* 30(2):151-157.

It is generally recognized in the art that mice are routinely used as models for the treatment of various conditions and diseases using neutralizing antibodies. For example, neutralizing antibodies have been used to treat prion disease, diabetes, and inflammation in mice. See, e.g., White et al. (2003) *Nature* 422:80-83; Cailleau et al. (1997) *Diabetes* 46:937-940; and Lochner et al. (2002) *J. Immunol. Methods* 259:149-157. In the latter study, monoclonal antibodies that neutralize mouse IL-18 were raised in IL-18 deficient mice. Those mouse monoclonal antibodies were capable of suppressing lipopolysaccharide-induced inflammatory response in wild-type mice. Thus, one skilled in the art would conclude that the foregoing examples support the use of neutralizing monoclonal antibodies against human ANGPTL3 in the treatment of human medical conditions.

TABLE 7

Table of Sequences

| Description | SEQ ID NO: | Sequence |
|---|---|---|
| mouse ANGPTL3 (Accession No. NP_038941) | 1 | MHTIKLFLFV VPLVIASRVD PDLSSFDSAP SEPKSRFAML DDVKILANGL LQLGHGLKDF VHKTKGQIND IFQKLNIFDQ SFYDLSLRTN EIKEEEKELR RTTSTLQVKN EEVKNMSVEL NSKLESLLEE KTALQHKVRA LEEQLTNLIL SPAGAQEHPE VTSLKSFVEQ QDNSIRELLQ SVEEQYKQLS QQHMQIKEIE KQLRKTGIQE PSENSLSSKS RAPRTTPPLQ LNETENTEQD DLPADCSAVY NRGEHTSGVY TIKPRNSQGF NVYCDTQSGS PWTLIQHRKD GSQDFNETWE NYEKGFGRLD GEFWLGLEKI YAIVQQSNYI LRLELQDWKD SKHYVEYSFH LGSHETNYTL HVAEIAGNIP GALPEHTDLM FSTWNHRAKG QLYCPESYSG GWWWNDICGE NNLNGKYNKP RTKSRPERRR GIYWRPQSRK LYAIKSSKMM LQPTT |

TABLE 7-continued

Table of Sequences

| Description | SEQ ID NO: | Sequence |
|---|---|---|
| mANGPTL3T | 2 | MHTIKLFLFV VPLVIASRVD PDLSSFDSAP SEPKSRFAML<br>DDVKILANGL LQLGHGLKDF VHKTKGQIND IFQKLNIFDQ<br>SFYDLSLRTN EIKEEEKELR RTTSTLQVKN EEVKNMSVEL<br>NSKLESLLEE KTALQHKVRA LEEQLTNLIL SPAGAQEHPE<br>VTSLKSFVEQ QDNSIRELLQ SVEEQYKQLS QQHMQIKEIE<br>KQLRKTGIQE PSENSLSSKS RAPRTTPPLQ LNETENTEQD<br>DLPADCSAVY NRGEHTSGVY TIKPRNSQGF NVYCDTQSGS<br>PWTLIQHRKD GSQDFNETWE NYEKGFGRLD GEFWLGLEKI<br>YAIVQQSNYI LRLELQDWKD SKHYVEYSFH LGSHETNYTL<br>HVAEIAGNIP GALPEHTDLM FSTWNHRAKG QLYCPESYSG<br>GWWWNDICGE NNLNGKYNKP RTKSRPERRR GIYWRPQSRK<br>LYAIKSSKMM LQPTTGHHHHH H |
| human ANGPTL3<br>(Accession No.<br>NP_055310) | 3 | MFTIKLLLFI VPLVISSRID QDNSSFDSLS PEPKSRFAML<br>DDVKILANGL LQLGHGLKDF VHKTKGQIND IFQKLNIFDQ<br>SFYDLSLQTS EIKEEEKELR RTTYKLQVKN EEVKNMSLEL<br>NSKLESLLEE KILLQQKVKY LEEQLTNLIQ NQPETPEHPE<br>VTSLKTFVEK QDNSIKDLLQ TVEDQYKQLN QQHSQIKEIE<br>NQLRRTSIQE PTEISLSSKP RAPRTTPFLQ LNEIRNVKHD<br>GIPAECTTIY NRGEHTSGMY AIRPSNSQVF HVYCDVISGS<br>PWTLIQHRID GSQNFNETWE NYKYGFGRLD GEFWLGLEKI<br>YSIVKQSNYV LRIELEDWKD NKHYIEYSFY LGNHETNYTL<br>HLVAITGNVP NAIPENKDLV FSTWDHKAKG HFNCPEGYSG<br>GWWWHDECGE NNLNGKYNKP RAKSKPERRR GLSWKSQNGR<br>LYSIKSTKML IHPTDSESFE |
| hANGPTL3T | 4 | MFTIKLLLFI VPLVISSRID QDNSSFDSLS PEPKSRFAML<br>DDVKILANGL LQLGHGLKDF VHKTKGQIND IFQKLNIFDQ<br>SFYDLSLQTS EIKEEEKELR RTTYKLQVKN EEVKNMSLEL<br>NSKLESLLEE KILLQQKVKY LEEQLTNLIQ NQPETPEHPE<br>VTSLKTFVEK QDNSIKDLLQ TVEDQYKQLN QQHSQIKEIE<br>NQLRRTSIQE PTEISLSSKP RAPRTTPFLQ LNEIRNVKHD<br>GIPAECTTIY NRGEHTSGMY AIRPSNSQVF HVYCDVISGS<br>PWTLIQHRID GSQNFNETWE NYKYGFGRLD GEFWLGLEKI<br>YSIVKQSNYV LRIELEDWKD NKHYIEYSFY LGNHETNYTL<br>HLVAITGNVP NAIPENKDLV FSTWDHKAKG HFNCPEGYSG<br>GWWWHDECGE NNLNGKYNKP RAKSKPERRR GLSWKSQNGR<br>LYSIKSTKML IHPTDSESFE GHHHHHH |
| mouse Angptl3<br>(Accession No.<br>NM_013913)<br>(mRNA/cDNA) | 5 | TCAGGAGGGA GAAGTTCCAA ATTGCTTAAA ATTGAATAAT<br>TGAGACAAAA AATGCACACA ATTAAATTAT TCCTTTTTGT<br>TGTTCCTTTA GTAATTGCAT CCAGAGTGGA TCCAGACCTT<br>TCATCATTTG ATTCTGCACC TTCAGAGCCA AAATCAAGAT<br>TTGCTATGTT GGATGATGTC AAAATTTTAG CGAATGGCCT<br>CCTGCAGCTG GGTCATGGAC TTAAAGATTT TGTCCATAAG<br>ACTAAGGGAC AAATTAATGA CATATTTCAG AAACTCAACA<br>TATTTGATCA GTCTTTTTAT GACCTATCAC TTCGAACCAA<br>TGAAATCAAA GAAGAGGAAA AGGAGCTAAG AAGAACTACA<br>TCTACACTAC AAGTTAAAAA CGAGGAGGTG AAGAACATGT<br>CAGTAGAACT GAACTCAAAG CTTGAGAGTC TGCTGGAAGA<br>GAAGACAGCC TTCAACACA AGGTCAGGGC TTTGGAGGAG<br>CAGCTAACCA ACTTAATTCT AAGCCCAGCT GGGGCTCAGG<br>AGCACCCAGA AGTAACATCA CTCAAAAGTT TTGTAGAACA<br>GCAAGACAAC AGCATAAGAG AACTCCTCCA GAGTGTGGAA<br>GAACAGTATA AACAATTAAG TCAACAGCAC ATGCAGATAA<br>AAGAAATAGA AAAGCAGCTC AGAAAGACTG GTATTCAAGA<br>ACCCTCAGAA AATTCTCTTT CTTCTAAATC AAGAGCACCA<br>AGAACTACTC CCCCTCTTCA ACTGAACGAA ACAGAAAATA<br>CAGAACAAGA TGACCTTCCT GCCGACTGCT CTGCCGTTTA<br>TAACAGAGGC GAACATACAA GTGGCGTGTA CACTATTAAA<br>CCAAGAAACT CCCAAGGGTT TAATGTCTAC TGTGATACCC<br>AATCAGGCAG TCCATGGACA TTAATTCAAC ACCGGAAAGA<br>TGGCTCACAG GACTTCAACG AAACATGGGA AAACTACGAA<br>AAGGGCTTTG GGAGGCTCGA TGGAGAATTT TGGTTGGGCC<br>TAGAGAAGAT CTATGCTATA GTCCAACAGT CTAACTACAT<br>TTTACGACTC GAGCTACAAG ACTGGAAAGA CAGCAAGCAC<br>TACGTTGAAT ACTCCTTTCA CCTGGGCAGT CACGAAACCA<br>ACTACACGCT ACATGTGGCT GAGATTGCTG GCAATATCCC<br>TGGGGCCCTC CCAGAGCACA CAGACCTGAT GTTTTCTACA<br>TGGAATCACA GAGCAAAGGG ACAGCTCTAC TGTCCAGAAA<br>GTTACTCAGG TGGCTGGTGG TGGAATGACA TATGTGGAGA<br>AAACAACCTA AATGGAAAAT ACAACAAACC CAGAACCAAA<br>TCCAGACCAG AGAGAAGAAG AGGGATCTAC TGGAGACCTC<br>AGAGCAGAAA GCTCTATGCT ATCAAATCAT CCAAAATGAT |

TABLE 7-continued

Table of Sequences

| Description | SEQ ID NO: | Sequence |
|---|---|---|
| | | GCTCCAGCCC ACCACCTAAG AAGCTTCAAC TGAACTGAGA<br>CAAAATAAAA GATCAATAAA TTAAATATTA AAGTCCTCCC<br>GATCACTGTA GTAATCTGGT ATTAAAATTT TAATGGAAAG<br>CTTGAGAATT GAATTTCAAT TAGGTTTAAA CTCATTGTTA<br>AGATCAGATA TCACCGAATC AACGTAAACA AAATTTATCT<br>TTTTC |
| human Angptl3 (Accession No. NM_014495) (mRNA/cDNA) | 6 | TTCCAGAAGA AAACAGTTCC ACGTTGCTTG AAATTGAAAA<br>TCAAGATAAA AATGTTCACA ATTAAGCTCC TTCTTTTTAT<br>TGTTCCTCTA GTTATTCCT CCAGAATTGA TCAAGACAAT<br>TCATCATTTG ATTCTCTATC TCCAGAGCCA AAATCAAGAT<br>TTGCTATGTT AGACGATGTA AAAATTTTAG CCAATGGCCT<br>CCTTCAGTTG GACATGGTC TTAAAGACTT TGTCCATAAG<br>ACGAAGGGCC AAATTAATGA CATATTTCAA AAACTCAACA<br>TATTTGATCA GTCTTTTTAT GATCTATCGC TGCAAACCAG<br>TGAAATCAAA GAAGAAGAAA AGGAACTGAG AAGAACTACA<br>TATAAACTAC AAGTCAAAAA TGAAGAGGTA AAGAATATGT<br>CACTTGAACT CAACTCAAAA CTTGAAAGCC TCCTAGAAGA<br>AAAAATTCTA CTTCAACAAA AAGTGAAATA TTTAGAAGAG<br>CAACTAACTA ACTTAATTCA AAATCAACCT GAAACTCCAG<br>AACACCCAGA AGTAACTTCA CTTAAAACTT TTGTAGAAAA<br>ACAAGATAAT AGCATCAAAG ACCTTCTCCA GACCGTGGAA<br>GACCAATATA AACAATTAAA CCAACAGCAT AGTCAAATAA<br>AAGAAATAGA AAATCAGCTC AGAAGGACTA GTATTCAAGA<br>ACCCACAGAA ATTTCTCTAT CTTCCAAGCC AAGAGCACCA<br>AGAACTACTC CCTTTCTTCA GTTGAATGAA ATAAGAAATG<br>TAAAACATGA TGGCATTCCT GCTGAATGTA CCACCATTTA<br>TAACAGAGGT GAACATACAA GTGGCATGTA TGCCATCAGA<br>CCCAGCAACT CTCAAGTTTT TCATGTCTAC TGTGATGTTA<br>TATCAGGTAG TCCATGGACA TTAATTCAAC ATCGAATAGA<br>TGGATCACAA AACTTCAATG AAACGTGGGA GAACTACAAA<br>TATGGTTTTG GGAGGCTTGA TGGAGAATTT TGGTTGGGCC<br>TAGAGAAGAT ATACTCCATA GTGAAGCAAT CTAATTATGT<br>TTTACGAATT GAGTTGGAAG ACTGGAAAGA CAACAAACAT<br>TATATTGAAT ATTCTTTTTA CTTGGGAAAT CACGAAACCA<br>ACTATACGCT ACATCTAGTT GCGATTACTG GCAATGTCCC<br>CAATGCAATC CCGGAAAACA AAGATTTGGT GTTTTCTACT<br>TGGGATCACA AAGCAAAAGG ACACTTCAAC TGTCCAGAGG<br>GTTATTCAGG AGGCTGGTGG TGGCATGATG AGTGTGGAGA<br>AAACAACCTA AATGGTAAAT ATAACAAACC AAGAGCAAAA<br>TCTAAGCCAG AGAGGAGAAG AGGATTATCT TGGAAGTCTC<br>AAAATGGAAG GTTATACTCT ATAAAATCAA CCAAAATGTT<br>GATCCATCCA ACAGATTCAG AAAGCTTTGA ATGAACTGAG<br>GCAAATTTAA AAGGCAATAA TTTAAACATT AACCTCATTC<br>CAAGTTAATG TGGTCTAATA ATCTGGTATT AAATCCTTAA<br>GAGAAAGCTT GAGAAATAGA TTTTTTTTAT CTTAAAGTCA<br>CTGTCTATTT AAGATTAAAC ATACAATCAC ATAACCTTAA<br>AGAATACCGT TTACATTTCT CAATCAAAAT TCTTATAATA<br>CTATTTGTTT TAAATTTTGT GATGTGGGAA TCAATTTTAG<br>ATGGTCACAA TCTAGATTAT AATCAATAGG TGAACTTATT<br>AAATAACTTT TCTAAATAAA AAATTTAGAG ACTTTTATTT<br>TAAAGGCAT CATATGAGCT AATATCACAA CTTTCCCAGT<br>TTAAAAAACT AGTACTCTTG TTAAAACTCT AAACTTGACT<br>AAATACAGAG GACTGGTAAT TGTACAGTTC TTAAATGTTG<br>TAGTATTAAT TTCAAAACTA AAAATCGTCA GCACAGAGTA<br>TGTGTAAAAA TCTGTAATAC AAATTTTTAA ACTGATGCTT<br>CATTTTGCTA CAAAATAATT TGGAGTAAAT GTTTGATATG<br>ATTTATTTAT GAAACCTAAT GAAGCAGAAT TAAATACTGT<br>ATTAAAATAA GTTCGCTGTC TTTAAACAAA TGGAGATGAC<br>TACTAAGTCA CATTGACTTT AACATGAGGT ATCACTATAC<br>CTTATT |
| rN'-mANGPTL3T | 7 | SRVDPD LSSFDSAPSE PKSRFAMLDD VKILANGLLQ<br>LGHGLKDFVH KTKGQINDIF QKLNIFDQSF YDLSLRTNEI<br>KEEEKELRRT TSTLQVKNEE VKNMSVELNS KLESLLEEKT<br>ALQHKVRALE EQLTNLILSP AGAQEHPEVT SLKSFVEQQD<br>NSIRELLQSV EEQYKQLSQQ HMQIKEIEKQ LRKTGIQEPS<br>ENSLSSKSRA PRTTPPLQLN ETENTEQDLE HHHHHH |
| rN'-hANGPTL3T | 8 | DQDNSS FDSLSPEPKS RFAMLDDVKI LANGLLQLGH<br>GLKDFVHKTK GQINDIFQKL NIFDQSFYDL SLQTSEIKEE<br>EKELRRTTYK LQVKNEEVKN MSLELNSKLE SLLEEKILLQ<br>QKVKYLEEQL TNLIQNQPET PEHPEVTSLK TFVEKQDNSI<br>KDLLQTVEDQ YKQLNQQHSQ IKEIENQLRR TSIQEPTEIS<br>LSSKPRAPRT TPFLQLNEIR NVKHDGIPLE HHHHHH |

TABLE 7-continued

Table of Sequences

| Description | SEQ ID NO: | Sequence |
|---|---|---|
| mANGPTL3 SP1 region | 9 | EPKSRFAMLDDVKILANGLLQLGHGL |
| hANGPTL3 SP1 region | 10 | EPKSRFAMLDDVKILANGLLQLGHGL |
| $S^{17}$-$G^{66}$ peptide | 11 | SRVDPDLSSFDSAPSEPKSRFAMLDDVKILANGLLQLGHGLKD FVHKTKG |
| $D^{42}$-$E^{91}$ peptide | 12 | DVKILANGLLQLGHGLKDFVHKTKGQINDIFQKLNIFDQSFYD LSLRTNE |
| $Q^{67}$-$M^{116}$ peptide | 13 | QINDIFQKLNIFDQSFYDLSLRTNEIKEEEKELRRTTSTLQVK NEEVKNM |
| $I^{92}$-$L^{141}$ peptide | 14 | IKEEEKELRRTTSTLQVKNEEVKNMSVELNSKLESLLEEKTAL QHKVRAL |
| $S^{117}$-$S^{166}$ peptide | 15 | SVELNSKLESLLEEKTALQHKVRALEEQLTNLILSPAGAQEHP EVTSLKS |
| $E^{142}$-$Q^{191}$ peptide | 16 | EEQLTNLILSPAGAQEHPEVTSLKSFVEQQDNSIRELLQSVEE QYKQLSQ |
| $F^{167}$-$L^{216}$ peptide | 17 | FVEQQDNSIRELLQSVEEQYKQLSQQHMQIKEIEKQLRKTGIQ EPSENSL |
| $Q^{192}$-$D^{241}$ peptide | 18 | QHMQIKEIEKQLRKTGIQEPSENSLSSKSRAPRTTPPLQLNET ENTEQDD |
| 4.7.1 heavy chain variable region | 19 | MEWSWIFLFL LSGTAGVHSE VQLQQSGPEL VKPGASVKMS CKASGYTFTS YVMHWVKQKP GQGLEWIGYF NPYNDGTKYN EKFKGKATLT SDKSSSTAYM ELSSLTSEDS AVYYCAREGD YYGYFDYWGQ GTTLTVSSA |
| 4.7.1 heavy chain variable region without signal peptide | 20 | E VQLQQSGPEL VKPGASVKMS CKASGYTFTS YVMHWVKQKP GQGLEWIGYF NPYNDGTKYN EKFKGKATLT SDKSSSTAYM ELSSLTSEDS AVYYCAREGD YYGYFDYWGQ GTTLTVSSA |
| 4.8.3 heavy chain variable region | 21 | MEWSWIFLFL LSGTAGVHSE VQLQQSGPEL VKPGASVKMS CKASGYTFIS CVMHWVKQKP GQGLEWIGYI NPYNDGTKYN EKFKGKATLT SDKSSSTAYM ELSSLTSEDS AVYYCAREGD YYGYFDYWGQ GTTLTVSSA |
| 4.8.3 heavy chain variable region without signal peptide | 22 | E VQLQQSGPEL VKPGASVKMS CKASGYTFIS CVMHWVKQKP GQGLEWIGYI NPYNDGTKYN EKFKGKATLT SDKSSSTAYM ELSSLTSEDS AVYYCAREGD YYGYFDYWGQ GTTLTVSSA |
| 4.9.1 heavy chain variable region | 23 | MEWSWIFLFL LSGTAGVHSE VQLQQSGPEL VKPGASVKMS CKASGYTFTS YVMHWVKQKP GQGLEWIGYI NPYNDGTKYN ENFKGKATLT SDKSSSTAYM EFSSLTSEDS AVYYCAREGD YYGYFDYWGQ GTTLTVSSA |
| 4.9.1 heavy chain variable region without signal peptide | 24 | E VQLQQSGPEL VKPGASVKMS CKASGYTFTS YVMHWVKQKP GQGLEWIGYI NPYNDGTKYN ENFKGKATLT SDKSSSTAYM EFSSLTSEDS AVYYCAREGD YYGYFDYWGQ GTTLTVSSA |
| heavy chain variable region consensus | 25 | MEWSWIFLFL LSGTAGVHSE VQLQQSGPEL VKPGASVKMS CKASGYTFTS YVMHWVKQKP GQGLEWIGYI NPYNDGTKYN EKFKGKATLT SDKSSSTAYM ELSSLTSEDS AVYYCAREGD YYGYFDYWGQ GTTLTVSSA |
| heavy chain variable region consensus without signal peptide | 26 | E VQLQQSGPEL VKPGASVKMS CKASGYTFTS YVMHWVKQKP GQGLEWIGYI NPYNDGTKYN EKFKGKATLT SDKSSSTAYM ELSSLTSEDS AVYYCAREGD YYGYFDYWGQ GTTLTVSSA |
| 4.7.1 light chain variable region | 27 | MSSAQFLGLL LLCFQGTRCD IQMTQTTSSL SASLGDRVTI SCRASQDISN FLNWYQQKPD GTVKLLIYYT SRLHSGVPSR FSGSGSGTDY SLTISNLEQE DIATYFCQQG NTLPPTFGGG TKLEIKR |

TABLE 7-continued

Table of Sequences

| Description | SEQ ID NO: | Sequence |
|---|---|---|
| 4.7.1 light chain variable region without signal peptide | 28 | D IQMTQTTSSL SASLGDRVTI SCRASQDISN FLNWYQQKPD GTVKLLIYYT SRLHSGVPSR FSGSGSGTDY SLTISNLEQE DIATYFCQQG NTLPPTFGGG TKLEIKR |
| 4.8.3 light chain variable region | 29 | MSSAQFLGLL LLCFQGIRCE IQMTQTTSSL SASLGDRVTI SCWASQDINN YLNWYQQKPD GTVKLLIYYT SRLHSGVPSR FSGSGSGTDY SLTISNLKQE DIATYFCQQG NTLPPTFGGG TKLEIKR |
| 4.8.3 light chain variable region without signal peptide | 30 | E IQMTQTTSSL SASLGDRVTI SCWASQDINN YLNWYQQKPD GTVKLLIYYT SRLHSGVPSR FSGSGSGTDY SLTISNLKQE DIATYFCQQG NTLPPTFGGG TKLEIKR |
| 4.9.1 light chain variable region | 31 | MSSAQFLGLL LLCFQGARCD IQMTQTTSSL SASLGDRVTI SCRASQDIRN YLNWYQQKPD GTVKLLIYYT SRLHSGVPSR FSGSGSGTDY SLTISNLEQE DIATYFCQQG NTLPPTFGGG TKLEIKR |
| 4.9.1 light chain variable region without signal peptide | 32 | D IQMTQTTSSL SASLGDRVTI SCRASQDIRN YLNWYQQKPD GTVKLLIYYT SRLHSGVPSR FSGSGSGTDY SLTISNLEQE DIATYFCQQG NTLPPTFGGG TKLEIKR |
| light chain variable region consensus | 33 | MSSAQFLGLL LLCFQGXRCD IQMTQTTSSL SASLGDRVTI SCRASQDIXN YLNWYQQKPD GTVKLLIYYT SRLHSGVPSR FSGSGSGTDY SLTISNLEQE DIATYFCQQG NTLPPTFGGG TKLEIKR |
| light chain variable region consensus without signal peptide | 34 | D IQMTQTTSSL SASLGDRVTI SCRASQDIXN YLNWYQQKPD GTVKLLIYYT SRLHSGVPSR FSGSGSGTDY SLTISNLEQE DIATYFCQQG NTLPPTFGGG TKLEIKR |
| 4.7.1 heavy chain CDR1 | 35 | GYTFTSYVMH |
| 4.7.1 heavy chain CDR2 | 36 | YFNPYNDGTKYNEKFKG |
| 4.7.1 heavy chain CDR3 | 37 | EGDYYGYFDY |
| 4.8.3 heavy chain CDR1 | 38 | GYTFISCVMH |
| 4.8.3 heavy chain CDR2 | 39 | YINPYNDGTKYNEKFKG |
| 4.8.3 heavy chain CDR3 | 40 | EGDYYGYFDY |
| 4.9.1 heavy chain CDR1 | 41 | GYTFTSYVMH |
| 4.9.1 heavy chain CDR2 | 42 | YINPYNDGTKYNENFKG |
| 4.9.1 heavy chain CDR3 | 43 | EGDYYGYFDY |
| 4.7.1 light chain CDR1 | 44 | RASQDISNFLN |
| 4.7.1 light chain CDR2 | 45 | YTSRLHS |
| 4.7.1 light chain CDR3 | 46 | QQGNTLPPT |
| 4.8.3 light chain CDR1 | 47 | WASQDINNYLN |

TABLE 7-continued

Table of Sequences

| Description | SEQ ID NO: | Sequence |
|---|---|---|
| 4.8.3 light chain CDR2 | 48 | YTSRLHS |
| 4.8.3 light chain CDR3 | 49 | QQGNTLPPT |
| 4.9.1 light chain CDR1 | 50 | RASQDIRNYLN |
| 4.9.1 light chain CDR2 | 51 | YTSRLHS |
| 4.9.1 light chain CDR3 | 52 | QQGNTLPPT |
| heavy chain CDR1 consensus | 53 | GYTFTSYVMH |
| heavy chain CDR2 consensus | 54 | YINPYNDGTKYNEKFKG |
| heavy chain CDR3 consensus | 55 | EGDYYGYFDY |
| light chain CDR1 consensus | 56 | RASQDIXNYLN |
| light chain CDR2 consensus | 57 | YTSRLHS |
| light chain CDR3 consensus | 58 | QQGNTLPPT |
| mouse ANGPTL3 $S^{17}$-$D^{240}$ | 59 | SRVD PDLSSFDSAP SEPKSRFAML DDVKILANGL LQLGHGLKDF VHKTKGQIND IFQKLNIFDQ SFYDLSLRTN EIKEEEKELR RTTSTLQVKN EEVKNMSVEL NSKLESLLEE KTALQHKVRA LEEQLTNLIL SPAGAQHPE VTSLKSFVEQ QDNSIRELLQ SVEEQYKQLS QQHMQIKEIE KQLRKTGIQE PSENSLSSKS RAPRTTPPLQ LNETENTEQD |
| human ANGPTL3 $D^{20}$-$P^{243}$ | 60 | D QDNSSFDSLS PEPKSRFAML DDVKILANGL LQLGHGLKDF VHKTKGQIND IFQKLNIFDQ SFYDLSLQTS EIKEEEKELR RTTYKLQVKN EEVKNMSLEL NSKLESLLEE KILLQQKVKY LEEQLTNLIQ NQPETPEHPE VTSLKTFVEK QDNSIKDLLQ TVEDQYKQLN QQHSQIKEIE NQLRRTSIQE PTEISLSSKP RAPRTTPPLQ LNEIRNVKHD GIP |
| mouse ANGPTL3 $D^{42}$-$M^{116}$ | 61 | DVKILANGL LQLGHGLKDF VHKTKGQIND IFQKLNIFDQ SFYDLSLRTN EIKEEEKELR RTTSTLQVKN EEVKNM |
| SP2-KLH | 62 | EPKSRFAMLDDVKILANGLLQLGHGLC |
| 5.35 heavy chain variable region | 63 | MGRLTSSFLL LIVPAYVLSQ VTLKESGPGI LHPSQTLTLT CSFSGFSLNT FGLAVGWIRQ PSGKGLEWLG HIWWDDHKYY NGVLKSRLTI SKDSSKKQVF LRIANVDTAD TARYYCARLE TGTGFAYWGQ GTLVTVSAA |
| 5.35 heavy chain variable region without signal peptide | 64 | Q VTLKESGPGI LHPSQTLTLT CSFSGFSLNT FGLAVGWIRQ PSGKGLEWLG HIWWDDHKYY NGVLKSRLTI SKDSSKKQVF LRIANVDTAD TARYYCARLE TGTGFAYWGQ GTLVTVSAA |
| 5.50 heavy chain variable region | 65 | MGWSWIFLFL LSGTAGVLSE VQLQQSGPEL VKPGASVKIS CKASGFTFTD YYMNWVKQSH GESLEWIGDI NPNNGGTIYN QKFRGKATLT VDKSSSTAYM ELRSLTSEDS AVYYCVRLPW YFDVWGTGTT VTVSSA |
| 5.50 heavy chain variable region without signal peptide | 66 | E VQLQQSGPEL VKPGASVKIS CKASGFTFTD YYMNWVKQSH GESLEWIGDI NPNNGGTIYN QKFRGKATLT VDKSSSTAYM ELRSLTSEDS AVYYCVRLPW YFDVWGTGTT VTVSSA |
| 5.35 light chain variable region | 67 | MRCLAEFLGL LVLWIPGAIG DIVLTQSTPS VPVTPGESVS ISCRSSKSLL DSNGITYLYW FLQRPGQSPQ LLIYRMSKLA |

TABLE 7-continued

Table of Sequences

| Description | SEQ ID NO: | Sequence |
|---|---|---|
| | | SGVPDRFSGS GSETAFTLRI SRVEAEDVGV YYCMQPLEYP FTFGAGTKLE LNG |
| 5.35 light chain variable region without signal peptide | 68 | DIVLTQSTPS VPVTPGESVS ISCRSSKSLL DSNGITYLYW FLQRPGQSPQ LLIYRMSKLA SGVPDRFSGS GSETAFTLRI SRVEAEDVGV YYCMQPLEYP FTFGAGTKLE LNG |
| 5.50 light chain variable region | 69 | MKLPVRLLVL MFWIPASSSD VLMTQTPLSL PVSLGDQASI SCRSSQSILH SNGNTYLEWF LQKPGQSPKL LIYKVSNRFS GVPDRFSGSG SGTDFTLKIS RVEAEDLGVY YCFQGSHVPY TFGGGTKLEI KR |
| 5.50 light chain variable region without signal peptide | 70 | D VLMTQTPLSL PVSLGDQASI SCRSSQSILH SNGNTYLEWF LQKPGQSPKL LIYKVSNRFS GVPDRFSGSG SGTDFTLKIS RVEAEDLGVY YCFQGSHVPY TFGGGTKLEI KR |
| 5.35 heavy chain CDR1 | 71 | GFSLNTFGLAVG |
| 5.35 heavy chain CDR2 | 72 | HIWWDDHKYYNGVLKS |
| 5.35 heavy chain CDR3 | 73 | LETGTGFAY |
| 5.50 heavy chain CDR1 | 74 | GFTFTDYYMN |
| 5.50 heavy chain CDR2 | 75 | DINPNNGGTIYNQKFRG |
| 5.50 heavy chain CDR3 | 76 | LPWYFDV |
| 5.35 light chain CDR1 | 77 | RSSKSLLDSNGITYLY |
| 5.35 light chain CDR2 | 78 | RMSKLAS |
| 5.35 light chain CDR3 | 79 | MQPLEYPFT |
| 5.50 light chain CDR1 | 80 | RSSQSILHSNGNTYLE |
| 5.50 light chain CDR2 | 81 | KVSNRFS |
| 5.50 light chain CDR3 | 82 | FQGSHVPYT |
| mutant 1 | 83 | APKSRFAMLDDVKILANGLLQLGHGL |
| mutant 2 | 84 | EAKSRFAMLDDVKILANGLLQLGHGL |
| mutant 3 | 85 | EPASRFAMLDDVKILANGLLQLGHGL |
| mutant 4 | 86 | EPKARFAMLDDVKILANGLLQLGHGL |
| mutant 5 | 87 | EPKSAFAMLDDVKILANGLLQLGHGL |
| mutant 6 | 88 | EPKSRAAMLDDVKILANGLLQLGHGL |
| mutant 8 | 89 | EPKSRFAALDDVKILANGLLQLGHGL |
| mutant 9 | 90 | EPKSRFAMADDVKILANGLLQLGHGL |
| mutant 10 | 91 | EPKSRFAMLADVKILANGLLQLGHGL |
| mutant 11 | 92 | EPKSRFAMLDAVKILANGLLQLGHGL |
| mutant 12 | 93 | EPKSRFAMLDDAKILANGLLQLGHGL |

TABLE 7-continued

Table of Sequences

| Description | SEQ ID NO: | Sequence |
|---|---|---|
| mutant 13 | 94 | EPKSRFAMLDDVAILANGLLQLGHGL |
| mutant 14 | 95 | EPKSRFAMLDDVKALANGLLQLGHGL |
| mutant 15 | 96 | EPKSRFAMLDDVKIAANGLLQLGHGL |
| mutant 17 | 97 | EPKSRFAMLDDVKILAAGLLQLGHGL |
| mutant 18 | 98 | EPKSRFAMLDDVKILANALLQLGHGL |
| mutant 19 | 99 | EPKSRFAMLDDVKILANGALQLGHGL |
| mutant 20 | 100 | EPKSRFAMLDDVKILANGLAQLGHGL |
| mutant 21 | 101 | EPKSRFAMLDDVKILANGLLALGHGL |
| mutant 22 | 102 | EPKSRFAMLDDVKILANGLLQAGHGL |
| mutant 23 | 103 | EPKSRFAMLDDVKILANGLLQLAHGL |
| mutant 24 | 104 | EPKSRFAMLDDVKILANGLLQLGAGL |
| mutant 25 | 105 | EPKSRFAMLDDVKILANGLLQLGHAL |
| mutant 26 | 106 | EPKSRFAMLDDVKILANGLLQLGHGA |
| mouse ANGPTL4 (Accession No. NP_065606) | 107 | mrcaptagaa lvlcaatagl lsaqgrpaqp epprfaswde mnllahgllq lghglrehve rtrgqlgale rrmaacgnac qgpkgkdapf kdsedrvpeg qtpetlqslq tqlkaqnski qqlfqkvaqq qrylskqnlr iqnlqsqidl lapthldngv dktsrgkkls kmtqliglts nathlhrpar dcqelfqege rhsglfqiqp lgsppflvnc emtsdggwtv iqrrlngsvd fnqsweaykd gfgdpqgefw lglekmhsit gdrgsqlavq lqdwdgnakl lqfpihlgge dtayslqlte ptanelgatn vspnglslpf stwdqdhdlr gdlncaksls ggwwfgtcsh snlngqyfhs iprqrqerkk gifwktwkgr yyplqattll iqpmeataas |
| human ANGPTL4 (Accession No. NP_647475) | 108 | msgaptagaa lmlcaatavl lsaqggpvqs ksprfaswde mnvlahgllq lgqglrehae rtrsqlsale rrlsacgsac qgtegstdlp lapesrvdpe vlhslqtqlk aqnsriqqlf hkvaqqqrhl ekqhlriqhl qsqfglldhk hldhevakpa rrkrlpemaq pvdpahnvsr lhrlprdcqe lfqvgerqsg lfeiqpqgsp pflvnckmts dggwtviqrr hdgsvdfnrp weaykagfgd phgefwlgle kvhsitgdrn srlavqlrdw dgnaellqfs vhlggedtay slqltapvag qlgattvpps glsvpfstwd qdhdlrrdkn cakslsggww fgtcshsnln gqyfrsipqq rqklkkgifw ktwrgryypl qattmliqpm aaeaas |
| mouse ANGPTL4 SP1 region | 109 | QPEPPRFASW DEMNLLAHGL LQLGHGL |
| human ANGPTL4 SP1 region | 110 | SKSPRFASWD EMNVLAHGLL QLGQGL |

---

The invention claimed is:

1. A monoclonal antibody that binds to angiopoietin-like protein 3 (ANGPTL3) and neutralizes at least one activity of ANGPTL3, wherein the antibody binds to a peptide consisting of the amino acid sequence of SEQ ID NO: 9 with at least 3-fold greater affinity than the antibody binds to a peptide consisting of the amino acid sequence of SEQ ID NO: 86, 87, or 88.

2. The antibody of claim 1, wherein the antibody decreases the level of at least one serum lipid in vivo.

3. The antibody of claim 2, wherein the at least one serum lipid is selected from serum triglycerides, total cholesterol, and free fatty acids.

4. The antibody of claim 3, wherein the antibody decreases the level of at least two serum lipids in vivo.

5. The antibody of claim 1, wherein the antibody binds to mouse ANGPTL3 and human ANGPTL3.

6. The antibody of claim 1, wherein the antibody is selected from a mouse monoclonal antibody, a humanized monoclonal antibody, and a human monoclonal antibody.

7. The antibody of claim 1, wherein the antibody is an antibody fragment.

8. The antibody of claim 7, wherein the antibody fragment is selected from a scFv, a Fab, a Fab', and a F(ab')$_2$.

9. The monoclonal antibody of claim 1, wherein the heavy chain comprises a CDR1 as set forth in SEQ ID NO: 35, a CDR2 as set forth in SEQ ID NO: 36, and a CDR3 as set forth in SEQ ID NO: 37; and the light chain comprises a CDR1 as set forth in SEQ ID NO: 44, a CDR2 as set forth in SEQ ID NO: 45, and a CDR3 as set forth in SEQ ID NO: 46.

10. The monoclonal antibody of claim 1, wherein the heavy chain comprises a CDR1 as set forth in SEQ ID NO: 38, a CDR2 as set forth in SEQ ID NO: 39, and a CDR3 as set forth in SEQ ID NO: 40; and the light chain comprises a CDR1 as set forth in SEQ ID NO: 47, a CDR2 as set forth in SEQ ID NO: 48, and a CDR3 as set forth in SEQ ID NO: 49.

11. The monoclonal antibody of claim 1, wherein the heavy chain comprises a CDR1 as set forth in SEQ ID NO: 41, a CDR2 as set forth in SEQ ID NO: 42, and a CDR3 as set forth in SEQ ID NO: 43; and the light chain comprises a CDR1 as set forth in SEQ ID NO: 50, a CDR2 as set forth in SEQ ID NO: 51, and a CDR3 as set forth in SEQ ID NO: 52.

12. The monoclonal antibody of claim 1, wherein the heavy chain comprises a CDR1 as set forth in SEQ ID NO: 53, a CDR2 as set forth in SEQ ID NO: 54, and a CDR3 as set forth in SEQ ID NO: 55; and the light chain comprises a CDR1 as set forth in SEQ ID NO: 56, a CDR2 as set forth in SEQ ID NO: 57, and a CDR3 as set forth in SEQ ID NO: 58.

13. The monoclonal antibody of claim 1, wherein the heavy chain comprises a CDR1 as set forth in SEQ ID NO: 71, a CDR2 as set forth in SEQ ID NO: 72, and a CDR3 as set forth in SEQ ID NO: 73; and the light chain comprises a CDR1 as set forth in SEQ ID NO: 77, a CDR2 as set forth in SEQ ID NO: 78, and a CDR3 as set forth in SEQ ID NO: 79.

14. The monoclonal antibody of claim 1, wherein the heavy chain comprises a CDR1 as set forth in SEQ ID NO: 74, a CDR2 as set forth in SEQ ID NO: 75, and a CDR3 as set forth in SEQ ID NO: 76; and the light chain comprises a CDR1 as set forth in SEQ ID NO: 80, a CDR2 as set forth in SEQ ID NO: 81, and a CDR3 as set forth in SEQ ID NO: 82.

15. A pharmaceutical composition comprising the antibody of claim 1.

16. A method of treating a disorder of lipid metabolism comprising administering to a patient an effective amount of the pharmaceutical composition of claim 15, wherein the disorder of lipid metabolism is selected from hypertriglyceridemia and hypercholesterolemia.

17. A method of decreasing the level of one or more serum lipids comprising administering to a patient an effective amount of the pharmaceutical composition of claim 15.

\* \* \* \* \*

SEQUENCE LISTING

<160> NUMBER OF SEQ ID NOS: 112

<210> SEQ ID NO 1
<211> LENGTH: 455
<212> TYPE: PRT
<213> ORGANISM: Mus musculus

<400> SEQUENCE: 1

Met His Thr Ile Lys Leu Phe Leu Phe Val Val Pro Leu Val Ile Ala

-continued

```
1               5                    10                   15
Ser Arg Val Asp Pro Asp Leu Ser Ser Phe Asp Ser Ala Pro Ser Glu
                 20                  25                  30

Pro Lys Ser Arg Phe Ala Met Leu Asp Asp Val Lys Ile Leu Ala Asn
                 35                  40                  45

Gly Leu Leu Gln Leu Gly His Gly Leu Lys Asp Phe Val His Lys Thr
 50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Arg Thr Asn Glu Ile Lys Glu Glu Glu
                 85                  90                  95

Lys Glu Leu Arg Arg Thr Thr Ser Thr Leu Gln Val Lys Asn Glu Glu
                100                 105                 110

Val Lys Asn Met Ser Val Glu Leu Asn Ser Lys Leu Glu Ser Leu Leu
                115                 120                 125

Glu Glu Lys Thr Ala Leu Gln His Lys Val Arg Ala Leu Glu Glu Gln
                130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Gln Tyr Lys Gln Leu Ser Gln Gln
                180                 185                 190

His Met Gln Ile Lys Glu Ile Glu Lys Gln Leu Arg Lys Thr Gly Ile
                195                 200                 205

Gln Glu Pro Ser Glu Asn Ser Leu Ser Ser Lys Ser Arg Ala Pro Arg
                210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
                260                 265                 270

Tyr Cys Asp Thr Gln Ser Gly Ser Pro Trp Thr Leu Ile Gln His Arg
                275                 280                 285

Lys Asp Gly Ser Gln Asp Phe Asn Glu Thr Trp Glu Asn Tyr Glu Lys
                290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335

Asp Trp Lys Asp Ser Lys His Tyr Val Glu Tyr Ser Phe His Leu Gly
                340                 345                 350

Ser His Glu Thr Asn Tyr Thr Leu His Val Ala Glu Ile Ala Gly Asn
                355                 360                 365

Ile Pro Gly Ala Leu Pro Glu His Thr Asp Leu Met Phe Ser Thr Trp
                370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Gly Ile
                420                 425                 430
```

```
Tyr Trp Arg Pro Gln Ser Arg Lys Leu Tyr Ala Ile Lys Ser Ser Lys
            435                 440                 445

Met Met Leu Gln Pro Thr Thr
    450                 455

<210> SEQ ID NO 2
<211> LENGTH: 462
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95

Lys Glu Leu Arg Arg Thr Thr Ser Thr Leu Gln Val Lys Asn Glu Glu
            100                 105                 110

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
    130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
    210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
                325                 330                 335
```

```
Asp Trp Lys Asp Ser Lys His Tyr Val Glu Tyr Ser Phe His Leu Gly
            340                 345                 350

Ser His Glu Thr Asn Tyr Thr Leu His Val Ala Glu Ile Ala Gly Asn
        355                 360                 365

Ile Pro Gly Ala Leu Pro Glu His Thr Asp Leu Met Phe Ser Thr Trp
    370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Gly Ile
        420                 425                 430

Tyr Trp Arg Pro Gln Ser Arg Lys Leu Tyr Ala Ile Lys Ser Ser Lys
        435                 440                 445

Met Met Leu Gln Pro Thr Thr Gly His His His His His His
    450                 455                 460

<210> SEQ ID NO 3
<211> LENGTH: 460
<212> TYPE: PRT
<213> ORGANISM: Homo sapiens

<400> SEQUENCE: 3

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255
```

```
Ser Gly Met Tyr Ala Ile Arg Pro Ser Asn Ser Gln Val Phe His Val
        260                 265                 270

Tyr Cys Asp Val Ile Ser Gly Ser Pro Trp Thr Leu Ile Gln His Arg
            275                 280                 285

Ile Asp Gly Ser Gln Asn Phe Asn Glu Thr Trp Glu Asn Tyr Lys Tyr
        290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
        370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 4
<211> LENGTH: 467
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

Met Phe Thr Ile Lys Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160
```

-continued

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu Gly His His His
    450                 455                 460

His His His
465

<210> SEQ ID NO 5
<211> LENGTH: 1605
<212> TYPE: DNA
<213> ORGANISM: Mus musculus

<400> SEQUENCE: 5
tcaggaggga gaagttccaa attgcttaaa attgaataat tgagacaaaa aatgcacaca      60
attaaattat tccttttttgt tgttcccttta gtaattgcat ccagagtgga tccagacctt     120
tcatcatttg attctgcacc ttcagagcca aaatcaagat ttgctatgtt ggatgatgtc     180 aaaatttttag cgaatggcct cctgcagctg ggtcatggac ttaaagattt tgtccataag     240
actaagggac aaattaacga catatttcag aagctcaaca tatttgatca gtcttttttat     300 gacctatcac ttcgaaccaa tgaaatcaaa gaagaggaaa aggagctaag aagaactaca     360

```
tctacactac aagttaaaaa cgaggaggtg aagaacatgt cagtagaact gaactcaaag      420
cttgagagtc tgctggaaga aagacagcc cttcaacaca aggtcagggc tttggaggag      480
cagctaacca acttaattct aagcccagct ggggctcagg agcacccaga agtaacatca      540
ctcaaaagtt ttgtagaaca gcaagacaac agcataagag aactcctcca gagtgtggaa      600
gaacagtata acaattaag tcaacagcac atgcagataa agaaataga aaagcagctc       660 agaaagactg gtattcaaga accctcagaa aattctcttt cttctaaatc aagagcacca     720
agaactactc cccctcttca actgaacgaa acagaaaata cagaacaaga tgaccttcct     780
gccgactgct ctgccgttta taacagaggc gaacatacaa gtggcgtgta cactattaaa    840
ccaagaaact cccaagggtt taatgtctac tgtgataccc aatcaggcag tccatggaca    900
ttaattcaac accggaaaga tggctcacag gacttcaacg aaacatggga aaactacgaa    960
aagggctttg ggaggctcga tggagaattt tggttgggcc tagagaagat ctatgctata   1020
gtccaacagt ctaactacat tttacgactc gagctacaag actggaaaga cagcaagcac   1080
tacgttgaat actccttca cctgggcagt cacgaaacca actacacgct acatgtggct    1140
gagattgctg gcaatatccc tggggccctc ccagagcaca cagacctgat gttttctaca   1200
tggaatcaca gagcaagggg acagctctac tgtccagaaa gttactcagg tggctggtgg   1260
tggaatgaca tatgtggaga aaacaaccta aatggaaaat acaacaaacc cagaaccaaa   1320
tccagaccag agagaagaag agggatctac tggagacctc agagcagaaa gctctatgct   1380
atcaaatcat ccaaaatgat gctccagccc accacctaag aagcttcaac tgaactgaga   1440
caaaataaaa gatcaataaa ttaaatatta aagtcctccc gatcactgta gtaatctggt   1500
attaaaattt taatgaaaag cttgagaatt gaatttcaat taggtttaaa ctcattgtta   1560
agatcagata tcaccgaatc aacgtaaaca aaatttatct ttttc                   1605

<210> SEQ ID NO 6
<211> LENGTH: 2126
<212> TYPE: DNA
<213> ORGANISM: Homo sapiens

<400> SEQUENCE: 6
ttccagaaga aaacagttcc acgttgcttg aaattgaaaa tcaagataaa atgttcaca      60 attaagctcc ttcttttat tgttcctcta gttatttcct ccagaattga tcaagacaat    120
tcatcatttg attctctatc tccagagcca aaatcaagat ttgctatgtt agacgatgta    180
aaaattttag ccaatggcct ccttcagttg gacatggtc ttaaagactt tgtccataag    240
acgaagggcc aaattaatga catatttcaa aaactcaaca tatttgatca gtcttttat    300 gatctatcgc tgcaaaccag tgaaatcaaa gaagaagaaa aggaactgag aagaactaca   360
tataaactac aagtcaaaaa tgaagaggta aagaatatgt cacttgaact caactcaaaa   420
cttgaaagcc tcctagaaga aaaaattcta cttcaacaaa aagtgaaaata tttagaagag   480 caactaacta acttaattca aaatcaacct gaaactccag aacacccaga agtaacttca   540
cttaaaactt ttgtagaaaa acaagataat agcatcaaag accttctcca gaccgtggaa   600
gaccaatata acaattaaa ccaacagcat agtcaaataa agaaataga aatcagctc      660 agaaggacta gtattcaaga acccacagaa atttctctat cttccaagcc aagagcacca   720
agaactactc cctttcttca gttgaatgaa ataagaaatg taaaacatga tggcattcct   780
gctgaatgta ccaccatta taacagaggt gaacatacaa gtggcatgta tgccatcaga   840
cccagcaact ctcaagtttt tcatgtctac tgtgatgtta tatcaggtag tccatggaca   900
```

```
ttaattcaac atcgaataga tggatcacaa aacttcaatg aaacgtggga gaactacaaa    960
tatggttttg ggaggcttga tggagaattt tggttgggcc tagagaagat atactccata   1020
gtgaagcaat ctaattatgt tttacgaatt gagttggaag actggaaaga caacaaacat   1080
tatattgaat attcttttta cttgggaaat cacgaaacca actatacgct acatctagtt   1140
gcgattactg gcaatgtccc caatgcaatc ccggaaaaca aagatttggt gttttctact   1200
tgggatcaca aagcaaaagg acacttcaac tgtccagagg gttattcagg aggctggtgg   1260
tggcatgatg agtgtggaga aaacaaccta aatggtaaat ataacaaacc aagagcaaaa   1320
tctaagccag agaggagaag aggattatct tggaagtctc aaaatggaag gttatactct   1380
ataaaatcaa ccaaaatgtt gatccatcca acagattcag aaagctttga atgaactgag   1440
gcaaatttaa aaggcaataa tttaaacatt aacctcattc aagttaatg tggtctaata    1500
atctggtatt aaatccttaa gagaaagctt gagaaataga ttttttttat cttaaagtca   1560
ctgtctattt aagattaaac atacaatcac ataaccttaa agaataccgt ttacatttct   1620
caatcaaaat tcttataata ctatttgttt taaattttgt gatgtgggaa tcaattttag   1680
atggtcacaa tctagattat aatcaatagg tgaacttatt aaataacttt tctaaataaa   1740
aaatttagag acttttattt taaaaggcat catatgagct aatatcacaa ctttcccagt   1800
ttaaaaaact agtactcttg ttaaaactct aaacttgact aaatacagag gactggtaat   1860
tgtacagttc ttaaatgttg tagtattaat ttcaaaacta aaaatcgtca gcacagagta   1920
tgtgtaaaaa tctgtaatac aaatttttaa actgatgctt cattttgcta caaaataatt   1980
tggagtaaat gtttgatatg atttatttat gaaacctaat gaagcagaat taaatactgt   2040
attaaaataa gttcgctgtc tttaaacaaa tggagatgac tactaagtca cattgacttt   2100
aacatgaggt atcactatac cttatt                                         2126
```

<210> SEQ ID NO 7
<211> LENGTH: 232
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Ser Arg Val Asp Pro Asp Leu Ser Ser Phe Asp Ser Ala Pro Ser Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
        35                  40                  45

Lys Gly Gln Ile Asn Asp Ile Phe Gln Lys Leu Asn Ile Phe Asp Gln
    50                  55                  60

Ser Phe Tyr Asp Leu Ser Leu Arg Thr Asn Glu Ile Lys Glu Glu Glu
65                  70                  75                  80

Lys Glu Leu Arg Arg Thr Thr Ser Thr Leu Gln Val Lys Asn Glu Glu
                85                  90                  95

Val Lys Asn Met Ser Val Glu Leu Asn Ser Lys Leu Glu Ser Leu Leu
            100                 105                 110

Glu Glu Lys Thr Ala Leu Gln His Lys Val Arg Ala Leu Glu Glu Gln
        115                 120                 125

Leu Thr Asn Leu Ile Leu Ser Pro Ala Gly Ala Gln Glu His Pro Glu
    130                 135                 140

```
Val Thr Ser Leu Lys Ser Phe Val Glu Gln Gln Asp Asn Ser Ile Arg
145                 150                 155                 160

Glu Leu Leu Gln Ser Val Glu Glu Gln Tyr Lys Gln Leu Ser Gln Gln
                165                 170                 175

His Met Gln Ile Lys Glu Ile Glu Lys Gln Leu Arg Lys Thr Gly Ile
            180                 185                 190

Gln Glu Pro Ser Glu Asn Ser Leu Ser Ser Lys Ser Arg Ala Pro Arg
        195                 200                 205

Thr Thr Pro Pro Leu Gln Leu Asn Glu Thr Glu Asn Thr Glu Gln Asp
    210                 215                 220

Leu Glu His His His His His His
225                 230

<210> SEQ ID NO 8
<211> LENGTH: 232
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Asp Gln Asp Asn Ser Ser Phe Asp Ser Leu Ser Pro Glu Pro Lys Ser
1               5                   10                  15

Arg Phe Ala Met Leu Asp Asp Val Lys Ile Leu Ala Asn Gly Leu Leu
            20                  25                  30

Gln Leu Gly His Gly Leu Lys Asp Phe Val His Lys Thr Lys Gly Gln
        35                  40                  45

Ile Asn Asp Ile Phe Gln Lys Leu Asn Ile Phe Asp Gln Ser Phe Tyr
    50                  55                  60

Asp Leu Ser Leu Gln Thr Ser Glu Ile Lys Glu Glu Glu Lys Glu Leu
65                  70                  75                  80

Arg Arg Thr Thr Tyr Lys Leu Gln Val Lys Asn Glu Glu Val Lys Asn
                85                  90                  95

Met Ser Leu Glu Leu Asn Ser Lys Leu Glu Ser Leu Leu Glu Glu Lys
            100                 105                 110

Ile Leu Leu Gln Gln Lys Val Lys Tyr Leu Glu Glu Gln Leu Thr Asn
        115                 120                 125

Leu Ile Gln Asn Gln Pro Glu Thr Pro Glu His Pro Glu Val Thr Ser
    130                 135                 140

Leu Lys Thr Phe Val Glu Lys Gln Asp Asn Ser Ile Lys Asp Leu Leu
145                 150                 155                 160

Gln Thr Val Glu Asp Gln Tyr Lys Gln Leu Asn Gln Gln His Ser Gln
                165                 170                 175

Ile Lys Glu Ile Glu Asn Gln Leu Arg Arg Thr Ser Ile Gln Glu Pro
            180                 185                 190

Thr Glu Ile Ser Leu Ser Ser Lys Pro Arg Ala Pro Arg Thr Thr Pro
        195                 200                 205

Phe Leu Gln Leu Asn Glu Ile Arg Asn Val Lys His Asp Gly Ile Pro
    210                 215                 220

Leu Glu His His His His His His
225                 230

<210> SEQ ID NO 9
<211> LENGTH: 26
<212> TYPE: PRT
<213> ORGANISM: Mus musculus
```

```
<400> SEQUENCE: 9

Glu Pro Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 10
<211> LENGTH: 26
<212> TYPE: PRT
<213> ORGANISM: Homo sapiens

<400> SEQUENCE: 10

Glu Pro Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 11
<211> LENGTH: 50
<212> TYPE: PRT
<213> ORGANISM: Mus musculus

<400> SEQUENCE: 11

Ser Arg Val Asp Pro Asp Leu Ser Ser Phe Asp Ser Ala Pro Ser Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
        35                  40                  45

Lys Gly
    50

<210> SEQ ID NO 12
<211> LENGTH: 50
<212> TYPE: PRT
<213> ORGANISM: Mus musculus

<400> SEQUENCE: 12

Asp Val Lys Ile Leu Ala Asn Gly Leu Leu Gln Leu Gly His Gly Leu
1               5                   10                  15

Lys Asp Phe Val His Lys Thr Lys Gly Gln Ile Asn Asp Ile Phe Gln
            20                  25                  30

Lys Leu Asn Ile Phe Asp Gln Ser Phe Tyr Asp Leu Ser Leu Arg Thr
        35                  40                  45

Asn Glu
    50

<210> SEQ ID NO 13
<211> LENGTH: 50
<212> TYPE: PRT
<213> ORGANISM: Mus musculus

<400> SEQUENCE: 13

Gln Ile Asn Asp Ile Phe Gln Lys Leu Asn Ile Phe Asp Gln Ser Phe
1               5                   10                  15

Tyr Asp Leu Ser Leu Arg Thr Asn Glu Ile Lys Glu Glu Lys Glu
            20                  25                  30

Leu Arg Arg Thr Thr Ser Thr Leu Gln Val Lys Asn Glu Glu Val Lys
        35                  40                  45

Asn Met
```

-continued

<210> SEQ ID NO 14
<211> LENGTH: 50
<212> TYPE: PRT
<213> ORGANISM: Mus musculus

<400> SEQUENCE: 14

Ile Lys Glu Glu Glu Lys Glu Leu Arg Arg Thr Thr Ser Thr Leu Gln
1               5                   10                  15

Val Lys Asn Glu Glu Val Lys Asn Met Ser Val Glu Leu Asn Ser Lys
            20                  25                  30

Leu Glu Ser Leu Leu Glu Glu Lys Thr Ala Leu Gln His Lys Val Arg
        35                  40                  45

Ala Leu
    50

<210> SEQ ID NO 15
<211> LENGTH: 50
<212> TYPE: PRT
<213> ORGANISM: Mus musculus

<400> SEQUENCE: 15

Ser Val Glu Leu Asn Ser Lys Leu Glu Ser Leu Leu Glu Glu Lys Thr
1               5                   10                  15

Ala Leu Gln His Lys Val Arg Ala Leu Glu Glu Gln Leu Thr Asn Leu
            20                  25                  30

Ile Leu Ser Pro Ala Gly Ala Gln Glu His Pro Glu Val Thr Ser Leu
        35                  40                  45

Lys Ser
    50

<210> SEQ ID NO 16
<211> LENGTH: 50
<212> TYPE: PRT
<213> ORGANISM: Mus musculus

<400> SEQUENCE: 16

Glu Glu Gln Leu Thr Asn Leu Ile Leu Ser Pro Ala Gly Ala Gln Glu
1               5                   10                  15

His Pro Glu Val Thr Ser Leu Lys Ser Phe Val Glu Gln Gln Asp Asn
            20                  25                  30

Ser Ile Arg Glu Leu Leu Gln Ser Val Glu Gln Tyr Lys Gln Leu
        35                  40                  45

Ser Gln
    50

<210> SEQ ID NO 17
<211> LENGTH: 50
<212> TYPE: PRT
<213> ORGANISM: Mus musculus

<400> SEQUENCE: 17

Phe Val Glu Gln Gln Asp Asn Ser Ile Arg Glu Leu Leu Gln Ser Val
1               5                   10                  15

Glu Gln Gln Tyr Lys Gln Leu Ser Gln Gln His Met Gln Ile Lys Glu
            20                  25                  30

Ile Glu Lys Gln Leu Arg Lys Thr Gly Ile Gln Glu Pro Ser Glu Asn
        35                  40                  45

Ser Leu

-continued

```
<210> SEQ ID NO 18
<211> LENGTH: 50
<212> TYPE: PRT
<213> ORGANISM: Mus musculus

<400> SEQUENCE: 18

Gln His Met Gln Ile Lys Glu Ile Glu Lys Gln Leu Arg Lys Thr Gly
1               5                   10                  15

Ile Gln Glu Pro Ser Glu Asn Ser Leu Ser Ser Lys Ser Arg Ala Pro
            20                  25                  30

Arg Thr Thr Pro Pro Leu Gln Leu Asn Glu Thr Glu Asn Thr Glu Gln
        35                  40                  45

Asp Asp
    50

<210> SEQ ID NO 19
<211> LENGTH: 139
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 19

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Phe Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Glu Gly Asp Tyr Tyr Gly Tyr Phe Asp Tyr Trp
        115                 120                 125

Gly Gln Gly Thr Thr Leu Thr Val Ser Ser Ala
    130                 135

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 20

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45
```

```
Gly Tyr Phe Asn Pro Tyr Asn Asp Gly Thr Lys Tyr Asn Glu Lys Phe
            50                  55                  60

Lys Gly Lys Ala Thr Leu Thr Ser Asp Lys Ser Ser Thr Ala Tyr
 65                  70                  75                  80

Met Glu Leu Ser Ser Leu Thr Ser Glu Asp Ser Ala Val Tyr Tyr Cys
                 85                  90                  95

Ala Arg Glu Gly Asp Tyr Tyr Gly Tyr Phe Asp Tyr Trp Gly Gln Gly
                100                 105                 110

Thr Thr Leu Thr Val Ser Ser Ala
            115                 120
```

<210> SEQ ID NO 21
<211> LENGTH: 139
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 21

```
Met Glu Trp Ser Trp Ile Phe Leu Phe Leu Leu Ser Gly Thr Ala Gly
 1               5                  10                  15

Val His Ser Glu Val Gln Leu Gln Gln Ser Gly Pro Glu Leu Val Lys
                 20                  25                  30

Pro Gly Ala Ser Val Lys Met Ser Cys Lys Ala Ser Gly Tyr Thr Phe
             35                  40                  45

Ile Ser Cys Val Met His Trp Val Lys Gln Lys Pro Gly Gln Gly Leu
         50                  55                  60

Glu Trp Ile Gly Tyr Ile Asn Pro Tyr Asn Asp Gly Thr Lys Tyr Asn
 65                  70                  75                  80

Glu Lys Phe Lys Gly Lys Ala Thr Leu Thr Ser Asp Lys Ser Ser Ser
                 85                  90                  95

Thr Ala Tyr Met Glu Leu Ser Ser Leu Thr Ser Glu Asp Ser Ala Val
            100                 105                 110

Tyr Tyr Cys Ala Arg Glu Gly Asp Tyr Tyr Gly Tyr Phe Asp Tyr Trp
        115                 120                 125

Gly Gln Gly Thr Thr Leu Thr Val Ser Ser Ala
    130                 135
```

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

```
Glu Val Gln Leu Gln Gln Ser Gly Pro Glu Leu Val Lys Pro Gly Ala
 1               5                  10                  15

Ser Val Lys Met Ser Cys Lys Ala Ser Gly Tyr Thr Phe Ile Ser Cys
                 20                  25                  30

Val Met His Trp Val Lys Gln Lys Pro Gly Gln Gly Leu Glu Trp Ile
             35                  40                  45

Gly Tyr Ile Asn Pro Tyr Asn Asp Gly Thr Lys Tyr Asn Glu Lys Phe
         50                  55                  60

Lys Gly Lys Ala Thr Leu Thr Ser Asp Lys Ser Ser Ser Thr Ala Tyr
 65                  70                  75                  80

Met Glu Leu Ser Ser Leu Thr Ser Glu Asp Ser Ala Val Tyr Tyr Cys
```

```
                    85                  90                  95
Ala Arg Glu Gly Asp Tyr Tyr Gly Tyr Phe Asp Tyr Trp Gly Gln Gly
                100                 105                 110

Thr Thr Leu Thr Val Ser Ser Ala
        115                 120

<210> SEQ ID NO 23
<211> LENGTH: 139
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 23

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Asn Phe Lys Gly Lys Ala Thr Leu Thr Ser Asp Lys Ser Ser Ser
                85                  90                  95

Thr Ala Tyr Met Glu Phe Ser Ser Leu Thr Ser Glu Asp Ser Ala Val
            100                 105                 110

Tyr Tyr Cys Ala Arg Glu Gly Asp Tyr Tyr Gly Tyr Phe Asp Tyr Trp
        115                 120                 125

Gly Gln Gly Thr Thr Leu Thr Val Ser Ser Ala
    130                 135

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 24

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Asn Phe
    50                  55                  60

Lys Gly Lys Ala Thr Leu Thr Ser Asp Lys Ser Ser Ser Thr Ala Tyr
65                  70                  75                  80

Met Glu Phe Ser Ser Leu Thr Ser Glu Asp Ser Ala Val Tyr Tyr Cys
                85                  90                  95

Ala Arg Glu Gly Asp Tyr Tyr Gly Tyr Phe Asp Tyr Trp Gly Gln Gly
            100                 105                 110

Thr Thr Leu Thr Val Ser Ser Ala
        115                 120
```

<210> SEQ ID NO 25
<211> LENGTH: 139
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 25

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Ser Tyr Val Met His Trp Val Lys Gln Lys Pro Gly Gln Gly Leu
    50                  55                  60

Glu Trp Ile Gly Tyr Ile Asn Pro Tyr Asn Asp Gly Thr Lys Tyr Asn
65                  70                  75                  80

Glu Lys Phe Lys Gly Lys Ala Thr Leu Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Glu Gly Asp Tyr Tyr Gly Tyr Phe Asp Tyr Trp
        115                 120                 125

Gly Gln Gly Thr Thr Leu Thr Val Ser Ser Ala
    130                 135

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 26

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Asp Tyr Tyr Gly Tyr Phe Asp Tyr Trp Gly Gln Gly
            100                 105                 110

Thr Thr Leu Thr Val Ser Ser Ala
        115                 120

<210> SEQ ID NO 27
<211> LENGTH: 127
<212> TYPE: PRT
<213> ORGANISM: Artificial Sequence
<220> FEATURE:

<223> OTHER INFORMATION: Description of Artificial Sequence: Synthetic
      construct

<400> SEQUENCE: 27

```
Met Ser Ser Ala Gln Phe Leu Gly Leu Leu Leu Cys Phe Gln Gly
1               5                   10                  15

Thr Arg Cys Asp Ile Gln Met Thr Gln Thr Ser Ser Leu Ser Ala
            20                  25                  30

Ser Leu Gly Asp Arg Val Thr Ile Ser Cys Arg Ala Ser Gln Asp Ile
        35                  40                  45

Ser Asn Phe Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Pro Thr Phe Gly Gly Gly Thr Lys Leu Glu Ile Lys Arg
        115                 120                 125
```

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys Arg
            100                 105
```

<210> SEQ ID NO 29
<211> LENGTH: 127
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 29

```
Met Ser Ser Ala Gln Phe Leu Gly Leu Leu Leu Cys Phe Gln Gly
1               5                   10                  15

Ile Arg Cys Glu Ile Gln Met Thr Gln Thr Thr Ser Ser Leu Ser Ala
            20                  25                  30

Ser Leu Gly Asp Arg Val Thr Ile Ser Cys Trp Ala Ser Gln Asp Ile
        35                  40                  45
```

```
Asn Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Ser Asn
                85                  90                  95

Leu Lys Gln Glu Asp Ile Ala Thr Tyr Phe Cys Gln Gln Gly Asn Thr
            100                 105                 110

Leu Pro Pro Thr Phe Gly Gly Gly Thr Lys Leu Glu Ile Lys Arg
        115                 120                 125

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 30

Glu Ile Gln Met Thr Gln Thr Thr Ser Ser Leu Ser Ala Ser Leu Gly
 1               5                  10                  15

Asp Arg Val Thr Ile Ser Cys Trp Ala Ser Gln Asp Ile Asn Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Lys Gln
 65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys Arg
            100                 105

<210> SEQ ID NO 31
<211> LENGTH: 127
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Met Ser Ser Ala Gln Phe Leu Gly Leu Leu Leu Leu Cys Phe Gln Gly
 1               5                  10                  15

Ala Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Arg Asn Tyr Leu Asn Trp Tyr Gln Gln Lys Pro Asp Gly Thr Val Lys
 50                  55                  60

Leu Leu Ile Tyr Tyr Thr Ser Arg Leu His Ser Gly Val Pro Ser Arg
 65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110
```

-continued

Leu Pro Pro Thr Phe Gly Gly Gly Thr Lys Leu Glu Ile Lys Arg
            115                 120                 125

<210> SEQ ID NO 32
<211> LENGTH: 108
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 32

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys Arg
            100                 105

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (17)..(17)
<223> OTHER INFORMATION: Variable amino acid
<220> FEATURE:
<221> NAME/KEY: MOD_RES
<222> LOCATION: (49)..(49)
<223> OTHER INFORMATION: Variable amino acid

<400> SEQUENCE: 33

Met Ser Ser Ala Gln Phe Leu Gly Leu Leu Leu Cys Phe Gln Gly
1               5                   10                  15

Xaa Arg Cys Asp Ile Gln Met Thr Gln Thr Thr Ser Ser Leu Ser Ala
            20                  25                  30

Ser Leu Gly Asp Arg Val Thr Ile Ser Cys Arg Ala Ser Gln Asp Ile
        35                  40                  45

Xaa Asn Tyr Leu Asn Trp Tyr Gln Gln Lys Pro Asp Gly Thr Val Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Pro Thr Phe Gly Gly Gly Thr Lys Leu Glu Ile Lys Arg
        115                 120                 125

<210> SEQ ID NO 34

```
<211> LENGTH: 108
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (30)..(30)
<223> OTHER INFORMATION: Variable amino acid

<400> SEQUENCE: 34

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Xaa Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys Arg
            100                 105

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Tyr Thr Phe Thr Ser Tyr Val Met His
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Tyr Phe Asn Pro Tyr Asn Asp Gly Thr Lys Tyr Asn Glu Lys Phe Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Glu Gly Asp Tyr Tyr Gly Tyr Phe Asp Tyr
1               5                   10

<210> SEQ ID NO 38
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Tyr Thr Phe Ile Ser Cys Val Met His
1               5                   10

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Ile Asn Pro Tyr Asn Asp Gly Thr Lys Tyr Asn Glu Lys Phe Lys
1               5                   10                  15

Gly

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Gly Asp Tyr Tyr Gly Tyr Phe Asp Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gly Tyr Thr Phe Thr Ser Tyr Val Met His
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Tyr Ile Asn Pro Tyr Asn Asp Gly Thr Lys Tyr Asn Glu Asn Phe Lys
1               5                   10                  15

Gly

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 43

Glu Gly Asp Tyr Tyr Gly Tyr Phe Asp Tyr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ala Ser Gln Asp Ile Ser Asn Phe Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Thr Ser Arg Leu His Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Gln Gly Asn Thr Leu Pro Pro Thr
1               5

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Ala Ser Gln Asp Ile Asn Asn Tyr Leu Asn
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Thr Ser Arg Leu His Ser
1               5

<210> SEQ ID NO 49
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 49

Gln Gln Gly Asn Thr Leu Pro Pro Thr
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Gln Asp Ile Arg Asn Tyr Leu Asn
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Tyr Thr Ser Arg Leu His Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Gln Gly Asn Thr Leu Pro Pro Thr
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 53

Gly Tyr Thr Phe Thr Ser Tyr Val Met His
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 54

Tyr Ile Asn Pro Tyr Asn Asp Gly Thr Lys Tyr Asn Glu Lys Phe Lys
1               5                   10                  15

Gly

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 55

```
Glu Gly Asp Tyr Tyr Gly Tyr Phe Asp Tyr
1               5                   10
```

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)..(7)
<223> OTHER INFORMATION: Variable amino acid

<400> SEQUENCE: 56

```
Arg Ala Ser Gln Asp Ile Xaa Asn Tyr Leu Asn
1               5                   10
```

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 57

```
Tyr Thr Ser Arg Leu His Ser
1               5
```

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 58

```
Gln Gln Gly Asn Thr Leu Pro Pro Thr
1               5
```

<210> SEQ ID NO 59
<211> LENGTH: 224
<212> TYPE: PRT
<213> ORGANISM: Mus musculus

<400> SEQUENCE: 59

```
Ser Arg Val Asp Pro Asp Leu Ser Ser Phe Asp Ser Ala Pro Ser Glu
1               5                   10                  15
Pro Lys Ser Arg Phe Ala Met Leu Asp Asp Val Lys Ile Leu Ala Asn
                20                  25                  30
Gly Leu Leu Gln Leu Gly His Gly Leu Lys Asp Phe Val His Lys Thr
            35                  40                  45
Lys Gly Gln Ile Asn Asp Ile Phe Gln Lys Leu Asn Ile Phe Asp Gln
```

```
            50                  55                  60
Ser Phe Tyr Asp Leu Ser Leu Arg Thr Asn Glu Ile Lys Glu Glu
 65                  70                  75                  80

Lys Glu Leu Arg Arg Thr Thr Ser Thr Leu Gln Val Lys Asn Glu Glu
                 85                  90                  95

Val Lys Asn Met Ser Val Glu Leu Asn Ser Lys Leu Glu Ser Leu Leu
                100                 105                 110

Glu Glu Lys Thr Ala Leu Gln His Lys Val Arg Ala Leu Glu Glu Gln
                115                 120                 125

Leu Thr Asn Leu Ile Leu Ser Pro Ala Gly Ala Gln Glu His Pro Glu
130                 135                 140

Val Thr Ser Leu Lys Ser Phe Val Glu Gln Gln Asp Asn Ser Ile Arg
145                 150                 155                 160

Glu Leu Leu Gln Ser Val Glu Gln Tyr Lys Gln Leu Ser Gln Gln
                165                 170                 175

His Met Gln Ile Lys Glu Ile Glu Lys Gln Leu Arg Lys Thr Gly Ile
                180                 185                 190

Gln Glu Pro Ser Glu Asn Ser Leu Ser Ser Lys Ser Arg Ala Pro Arg
                195                 200                 205

Thr Thr Pro Pro Leu Gln Leu Asn Glu Thr Glu Asn Thr Glu Gln Asp
210                 215                 220

<210> SEQ ID NO 60
<211> LENGTH: 224
<212> TYPE: PRT
<213> ORGANISM: Homo sapiens

<400> SEQUENCE: 60

Asp Gln Asp Asn Ser Ser Phe Asp Ser Leu Ser Pro Glu Pro Lys Ser
 1               5                  10                  15

Arg Phe Ala Met Leu Asp Asp Val Lys Ile Leu Ala Asn Gly Leu Leu
                20                  25                  30

Gln Leu Gly His Gly Leu Lys Asp Phe Val His Lys Thr Lys Gly Gln
                35                  40                  45

Ile Asn Asp Ile Phe Gln Lys Leu Asn Ile Phe Asp Gln Ser Phe Tyr
 50                  55                  60

Asp Leu Ser Leu Gln Thr Ser Glu Ile Lys Glu Glu Lys Glu Leu
 65                  70                  75                  80

Arg Arg Thr Thr Tyr Lys Leu Gln Val Lys Asn Glu Glu Val Lys Asn
                85                  90                  95

Met Ser Leu Glu Leu Asn Ser Lys Leu Glu Ser Leu Leu Glu Glu Lys
                100                 105                 110

Ile Leu Leu Gln Gln Lys Val Lys Tyr Leu Glu Glu Gln Leu Thr Asn
                115                 120                 125

Leu Ile Gln Asn Gln Pro Glu Thr Pro Glu His Pro Glu Val Thr Ser
130                 135                 140

Leu Lys Thr Phe Val Glu Lys Gln Asp Asn Ser Ile Lys Asp Leu Leu
145                 150                 155                 160

Gln Thr Val Glu Asp Gln Tyr Lys Gln Leu Asn Gln Gln His Ser Gln
                165                 170                 175

Ile Lys Glu Ile Glu Asn Gln Leu Arg Arg Thr Ser Ile Gln Glu Pro
                180                 185                 190

Thr Glu Ile Ser Leu Ser Ser Lys Pro Arg Ala Pro Arg Thr Thr Pro
                195                 200                 205

Phe Leu Gln Leu Asn Glu Ile Arg Asn Val Lys His Asp Gly Ile Pro
```

<210> SEQ ID NO 61
<211> LENGTH: 75
<212> TYPE: PRT
<213> ORGANISM: Mus musculus

<400> SEQUENCE: 61

Asp Val Lys Ile Leu Ala Asn Gly Leu Leu Gln Leu Gly His Gly Leu
1               5                   10                  15

Lys Asp Phe Val His Lys Thr Lys Gly Gln Ile Asn Asp Ile Phe Gln
            20                  25                  30

Lys Leu Asn Ile Phe Asp Gln Ser Phe Tyr Asp Leu Ser Leu Arg Thr
        35                  40                  45

Asn Glu Ile Lys Glu Glu Lys Glu Leu Arg Arg Thr Thr Ser Thr
    50                  55                  60

Leu Gln Val Lys Asn Glu Glu Val Lys Asn Met
65                  70                  75

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Pro Lys Ser Arg Phe Ala Met Leu Asp Asp Val Lys Ile Leu Ala
1               5                   10                  15

Asn Gly Leu Leu Gln Leu Gly His Gly Leu Cys
            20                  25

<210> SEQ ID NO 63
<211> LENGTH: 139
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 63

Met Gly Arg Leu Thr Ser Ser Phe Leu Leu Ile Val Pro Ala Tyr
1               5                   10                  15

Val Leu Ser Gln Val Thr Leu Lys Glu Ser Gly Pro Gly Ile Leu His
            20                  25                  30

Pro Ser Gln Thr Leu Thr Leu Thr Cys Ser Phe Ser Gly Phe Ser Leu
        35                  40                  45

Asn Thr Phe Gly Leu Ala Val Gly Trp Ile Arg Gln Pro Ser Gly Lys
    50                  55                  60

Gly Leu Glu Trp Leu Gly His Ile Trp Trp Asp His Lys Tyr Tyr
65                  70                  75                  80

Asn Gly Val Leu Lys Ser Arg Leu Thr Ile Ser Lys Asp Ser Ser Lys
                85                  90                  95

Lys Gln Val Phe Leu Arg Ile Ala Asn Val Asp Thr Ala Asp Thr Ala
            100                 105                 110

Arg Tyr Tyr Cys Ala Arg Leu Glu Thr Gly Thr Gly Phe Ala Tyr Trp
        115                 120                 125

Gly Gln Gly Thr Leu Val Thr Val Ser Ala Ala
    130                 135

-continued

<210> SEQ ID NO 64
<211> LENGTH: 120
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 64

Gln Val Thr Leu Lys Glu Ser Gly Pro Gly Ile Leu His Pro Ser Gln
1               5                   10                  15

Thr Leu Thr Leu Thr Cys Ser Phe Ser Gly Phe Ser Leu Asn Thr Phe
            20                  25                  30

Gly Leu Ala Val Gly Trp Ile Arg Gln Pro Ser Gly Lys Gly Leu Glu
        35                  40                  45

Trp Leu Gly His Ile Trp Trp Asp Asp His Lys Tyr Tyr Asn Gly Val
    50                  55                  60

Leu Lys Ser Arg Leu Thr Ile Ser Lys Asp Ser Ser Lys Gln Val
65                  70                  75                  80

Phe Leu Arg Ile Ala Asn Val Asp Thr Ala Asp Thr Ala Arg Tyr Tyr
                85                  90                  95

Cys Ala Arg Leu Glu Thr Gly Thr Gly Phe Ala Tyr Trp Gly Gln Gly
            100                 105                 110

Thr Leu Val Thr Val Ser Ala Ala
        115                 120

<210> SEQ ID NO 65
<211> LENGTH: 136
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 65

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Phe Thr Phe
        35                  40                  45

Thr Asp Tyr Tyr Met Asn Trp Val Lys Gln Ser His Gly Glu Ser Leu
    50                  55                  60

Glu Trp Ile Gly Asp Ile Asn Pro Asn Asn Gly Gly Thr Ile Tyr Asn
65                  70                  75                  80

Gln Lys Phe Arg Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Val Arg Leu Pro Trp Tyr Phe Asp Val Trp Gly Thr Gly
        115                 120                 125

Thr Thr Val Thr Val Ser Ser Ala
    130                 135

<210> SEQ ID NO 66
<211> LENGTH: 117
<212> TYPE: PRT
<213> ORGANISM: Artificial Sequence
<220> FEATURE:
<223> OTHER INFORMATION: Description of Artificial Sequence: Synthetic -continued construct

<400> SEQUENCE: 66

Glu Val Gln Leu Gln Gln Ser Gly Pro Glu Leu Val Lys Pro Gly Ala
1               5                   10                  15

Ser Val Lys Ile Ser Cys Lys Ala Ser Gly Phe Thr Phe Thr Asp Tyr
            20                  25                  30

Tyr Met Asn Trp Val Lys Gln Ser His Gly Glu Ser Leu Glu Trp Ile
        35                  40                  45

Gly Asp Ile Asn Pro Asn Asn Gly Gly Thr Ile Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Leu Pro Trp Tyr Phe Asp Val Trp Gly Thr Gly Thr Thr Val
            100                 105                 110

Thr Val Ser Ser Ala
        115

<210> SEQ ID NO 67
<211> LENGTH: 133
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 67

Met Arg Cys Leu Ala Glu Phe Leu Gly Leu Leu Val Leu Trp Ile Pro
1               5                   10                  15

Gly Ala Ile Gly Asp Ile Val Leu Thr Gln Ser Thr Pro Ser Val Pro
            20                  25                  30

Val Thr Pro Gly Glu Ser Val Ser Ile Ser Cys Arg Ser Ser Lys Ser
        35                  40                  45

Leu Leu Asp Ser Asn Gly Ile Thr Tyr Leu Tyr Trp Phe Leu Gln Arg
    50                  55                  60

Pro Gly Gln Ser Pro Gln Leu Leu Ile Tyr Arg Met Ser Lys Leu Ala
65                  70                  75                  80

Ser Gly Val Pro Asp Arg Phe Ser Gly Ser Gly Ser Glu Thr Ala Phe
                85                  90                  95

Thr Leu Arg Ile Ser Arg Val Glu Ala Glu Asp Val Gly Val Tyr Tyr
            100                 105                 110

Cys Met Gln Pro Leu Glu Tyr Pro Phe Thr Phe Gly Ala Gly Thr Lys
        115                 120                 125

Leu Glu Leu Asn Gly
    130

<210> SEQ ID NO 68
<211> LENGTH: 113
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 68

Asp Ile Val Leu Thr Gln Ser Pro Ser Val Pro Val Thr Pro Gly
1               5                   10                  15

Glu Ser Val Ser Ile Ser Cys Arg Ser Ser Lys Ser Leu Leu Asp Ser
            20                  25                  30

Asn Gly Ile Thr Tyr Leu Tyr Trp Phe Leu Gln Arg Pro Gly Gln Ser
            35                  40                  45

Pro Gln Leu Leu Ile Tyr Arg Met Ser Lys Leu Ala Ser Gly Val Pro
50                      55                  60

Asp Arg Phe Ser Gly Ser Gly Ser Glu Thr Ala Phe Thr Leu Arg Ile
65                  70                  75                  80

Ser Arg Val Glu Ala Glu Asp Val Gly Val Tyr Tyr Cys Met Gln Pro
                85                  90                  95

Leu Glu Tyr Pro Phe Thr Phe Gly Ala Gly Thr Lys Leu Glu Leu Asn
                100                 105                 110

Gly

<210> SEQ ID NO 69
<211> LENGTH: 132
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 69

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
            35                  40                  45

Leu His Ser Asn Gly Asn Thr Tyr Leu Glu Trp Phe Leu Gln Lys Pro
50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Tyr Thr Phe Gly Gly Gly Thr Lys Leu
            115                 120                 125

Glu Ile Lys Arg
        130

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 70

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Phe Leu Gln Lys Pro Gly Gln Ser
            35                  40                  45

Pro Lys Leu Leu Ile Tyr Lys Val Ser Asn Arg Phe Ser Gly Val Pro
50                  55                  60

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Phe Ser Leu Asn Thr Phe Gly Leu Ala Val Gly
1               5                   10

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Ile Trp Trp Asp Asp His Lys Tyr Tyr Asn Gly Val Leu Lys Ser
1               5                   10                  15

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Leu Glu Thr Gly Thr Gly Phe Ala Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Thr Phe Thr Asp Tyr Tyr Met Asn
1               5                   10

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Ile Asn Pro Asn Asn Gly Gly Thr Ile Tyr Asn Gln Lys Phe Arg
```

-continued

```
1               5                   10                  15
Gly

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Leu Pro Trp Tyr Phe Asp Val
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Ser Ser Lys Ser Leu Leu Asp Ser Asn Gly Ile Thr Tyr Leu Tyr
1               5                   10                  15

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Met Ser Lys Leu Ala Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met Gln Pro Leu Glu Tyr Pro Phe Thr
1               5

<210> SEQ ID NO 80
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Ser Ser Gln Ser Ile Leu His Ser Asn Gly Asn Thr Tyr Leu Glu
1               5                   10                  15

<210> SEQ ID NO 81
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 81

Lys Val Ser Asn Arg Phe Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Gln Gly Ser His Val Pro Tyr Thr
1               5

<210> SEQ ID NO 83
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Pro Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Ala Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 85
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Glu Pro Ala Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 86
<211> LENGTH: 26
<212> TYPE: PRT
<213> ORGANISM: Artificial Sequence
<220> FEATURE:
<223> OTHER INFORMATION: Description of Artificial Sequence: Synthetic

```
<400> SEQUENCE: 86

Glu Pro Lys Ala Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 87
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Pro Lys Ser Ala Phe Ala Met Leu Asp Asp Val Lys Ile Leu Ala
1               5                   10                  15

Asn Gly Leu Leu Gln Leu Gly His Gly Leu
            20                  25

<210> SEQ ID NO 88
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Pro Lys Ser Arg Ala Ala Met Leu Asp Asp Val Lys Ile Leu Ala
1               5                   10                  15

Asn Gly Leu Leu Gln Leu Gly His Gly Leu
            20                  25

<210> SEQ ID NO 89
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Pro Lys Ser Arg Phe Ala Ala Leu Asp Asp Val Lys Ile Leu Ala
1               5                   10                  15

Asn Gly Leu Leu Gln Leu Gly His Gly Leu
            20                  25

<210> SEQ ID NO 90
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Pro Lys Ser Arg Phe Ala Met Ala Asp Asp Val Lys Ile Leu Ala
1               5                   10                  15

Asn Gly Leu Leu Gln Leu Gly His Gly Leu
            20                  25

<210> SEQ ID NO 91
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Glu Pro Lys Ser Arg Phe Ala Met Leu Ala Asp Val Lys Ile Leu Ala
1               5                   10                  15

Asn Gly Leu Leu Gln Leu Gly His Gly Leu
            20                  25

<210> SEQ ID NO 92
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Glu Pro Lys Ser Arg Phe Ala Met Leu Asp Ala Val Lys Ile Leu Ala
1               5                   10                  15

Asn Gly Leu Leu Gln Leu Gly His Gly Leu
            20                  25

<210> SEQ ID NO 93
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Pro Lys Ser Arg Phe Ala Met Leu Asp Asp Ala Lys Ile Leu Ala
1               5                   10                  15

Asn Gly Leu Leu Gln Leu Gly His Gly Leu
            20                  25

<210> SEQ ID NO 94
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Pro Lys Ser Arg Phe Ala Met Leu Asp Asp Val Ala Ile Leu Ala
1               5                   10                  15

Asn Gly Leu Leu Gln Leu Gly His Gly Leu
            20                  25

<210> SEQ ID NO 95
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Glu Pro Lys Ser Arg Phe Ala Met Leu Asp Asp Val Lys Ala Leu Ala
1               5                   10                  15
```

Asn Gly Leu Leu Gln Leu Gly His Gly Leu
            20                  25

<210> SEQ ID NO 96
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Glu Pro Lys Ser Arg Phe Ala Met Leu Asp Asp Val Lys Ile Ala Ala
1               5                   10                  15

Asn Gly Leu Leu Gln Leu Gly His Gly Leu
            20                  25

<210> SEQ ID NO 97
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Pro Lys Ser Arg Phe Ala Met Leu Asp Asp Val Lys Ile Leu Ala
1               5                   10                  15

Ala Gly Leu Leu Gln Leu Gly His Gly Leu
            20                  25

<210> SEQ ID NO 98
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Pro Lys Ser Arg Phe Ala Met Leu Asp Asp Val Lys Ile Leu Ala
1               5                   10                  15

Asn Ala Leu Leu Gln Leu Gly His Gly Leu
            20                  25

<210> SEQ ID NO 99
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Glu Pro Lys Ser Arg Phe Ala Met Leu Asp Asp Val Lys Ile Leu Ala
1               5                   10                  15

Asn Gly Ala Leu Gln Leu Gly His Gly Leu
            20                  25

<210> SEQ ID NO 100
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 100

Glu Pro Lys Ser Arg Phe Ala Met Leu Asp Asp Val Lys Ile Leu Ala
1               5                   10                  15

Asn Gly Leu Ala Gln Leu Gly His Gly Leu
            20                  25

<210> SEQ ID NO 101
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Pro Lys Ser Arg Phe Ala Met Leu Asp Asp Val Lys Ile Leu Ala
1               5                   10                  15

Asn Gly Leu Leu Ala Leu Gly His Gly Leu
            20                  25

<210> SEQ ID NO 102
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Glu Pro Lys Ser Arg Phe Ala Met Leu Asp Asp Val Lys Ile Leu Ala
1               5                   10                  15

Asn Gly Leu Leu Gln Ala Gly His Gly Leu
            20                  25

<210> SEQ ID NO 103
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Glu Pro Lys Ser Arg Phe Ala Met Leu Asp Asp Val Lys Ile Leu Ala
1               5                   10                  15

Asn Gly Leu Leu Gln Leu Ala His Gly Leu
            20                  25

<210> SEQ ID NO 104
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Glu Pro Lys Ser Arg Phe Ala Met Leu Asp Asp Val Lys Ile Leu Ala
1               5                   10                  15

Asn Gly Leu Leu Gln Leu Gly Ala Gly Leu
            20                  25

<210> SEQ ID NO 105
<211> LENGTH: 26
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 105

Glu Pro Lys Ser Arg Phe Ala Met Leu Asp Asp Val Lys Ile Leu Ala
1               5                   10                  15

Asn Gly Leu Leu Gln Leu Gly His Ala Leu
            20                  25

<210> SEQ ID NO 106
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Glu Pro Lys Ser Arg Phe Ala Met Leu Asp Asp Val Lys Ile Leu Ala
1               5                   10                  15

Asn Gly Leu Leu Gln Leu Gly His Gly Ala
            20                  25

<210> SEQ ID NO 107
<211> LENGTH: 410
<212> TYPE: PRT
<213> ORGANISM: Mus musculus

<400> SEQUENCE: 107

Met Arg Cys Ala Pro Thr Ala Gly Ala Ala Leu Val Leu Cys Ala Ala
1               5                   10                  15

Thr Ala Gly Leu Leu Ser Ala Gln Gly Arg Pro Ala Gln Pro Glu Pro
            20                  25                  30

Pro Arg Phe Ala Ser Trp Asp Glu Met Asn Leu Leu Ala His Gly Leu
        35                  40                  45

Leu Gln Leu Gly His Gly Leu Arg Glu His Val Glu Arg Thr Arg Gly
    50                  55                  60

Gln Leu Gly Ala Leu Glu Arg Arg Met Ala Ala Cys Gly Asn Ala Cys
65                  70                  75                  80

Gln Gly Pro Lys Gly Lys Asp Ala Pro Phe Lys Asp Ser Glu Asp Arg
                85                  90                  95

Val Pro Glu Gly Gln Thr Pro Gly Thr Leu Gln Ser Leu Gln Thr Gln
            100                 105                 110

Leu Lys Ala Gln Asn Ser Lys Ile Gln Gln Leu Phe Gln Lys Val Ala
        115                 120                 125

Gln Gln Gln Arg Tyr Leu Ser Lys Gln Asn Leu Arg Ile Gln Asn Leu
    130                 135                 140

Gln Ser Gln Ile Asp Leu Leu Ala Pro Thr His Leu Asp Asn Gly Val
145                 150                 155                 160

Asp Lys Thr Ser Arg Gly Lys Lys Leu Ser Lys Met Thr Gln Leu Ile
                165                 170                 175

Gly Leu Thr Ser Asn Ala Thr His Leu His Arg Pro Ala Arg Asp Cys
            180                 185                 190

Gln Glu Leu Phe Gln Glu Gly Glu Arg His Ser Gly Leu Phe Gln Ile
        195                 200                 205

Gln Pro Leu Gly Ser Pro Pro Phe Leu Val Asn Cys Glu Met Thr Ser
    210                 215                 220
```

```
Asp Gly Gly Trp Thr Val Ile Gln Arg Arg Leu Asn Gly Ser Val Asp
225                 230                 235                 240

Phe Asn Gln Ser Trp Glu Ala Tyr Lys Asp Gly Phe Gly Asp Pro Gln
            245                 250                 255

Gly Glu Phe Trp Leu Gly Leu Glu Lys Met His Ser Ile Thr Gly Asp
        260                 265                 270

Arg Gly Ser Gln Leu Ala Val Gln Leu Gln Asp Trp Asp Gly Asn Ala
    275                 280                 285

Lys Leu Leu Gln Phe Pro Ile His Leu Gly Gly Glu Asp Thr Ala Tyr
290                 295                 300

Ser Leu Gln Leu Thr Glu Pro Thr Ala Asn Glu Leu Gly Ala Thr Asn
305                 310                 315                 320

Val Ser Pro Asn Gly Leu Ser Leu Pro Phe Ser Thr Trp Asp Gln Asp
            325                 330                 335

His Asp Leu Arg Gly Asp Leu Asn Cys Ala Lys Ser Leu Ser Gly Gly
        340                 345                 350

Trp Trp Phe Gly Thr Cys Ser His Ser Asn Leu Asn Gly Gln Tyr Phe
    355                 360                 365

His Ser Ile Pro Arg Gln Arg Gln Glu Arg Lys Lys Gly Ile Phe Trp
370                 375                 380

Lys Thr Trp Lys Gly Arg Tyr Tyr Pro Leu Gln Ala Thr Thr Leu Leu
385                 390                 395                 400

Ile Gln Pro Met Glu Ala Thr Ala Ala Ser
            405                 410

<210> SEQ ID NO 108
<211> LENGTH: 406
<212> TYPE: PRT
<213> ORGANISM: Homo sapiens

<400> SEQUENCE: 108

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190
```

```
Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 109
<211> LENGTH: 27
<212> TYPE: PRT
<213> ORGANISM: Mus musculus

<400> SEQUENCE: 109

Gln Pro Glu Pro Pro Arg Phe Ala Ser Trp Asp Glu Met Asn Leu Leu
1               5                   10                  15

Ala His Gly Leu Leu Gln Leu Gly His Gly Leu
            20                  25

<210> SEQ ID NO 110
<211> LENGTH: 26
<212> TYPE: PRT
<213> ORGANISM: Homo sapiens

<400> SEQUENCE: 110

Ser Lys Ser Pro Arg Phe Ala Ser Trp Asp Glu Met Asn Val Leu Ala
1               5                   10                  15

His Gly Leu Leu Gln Leu Gly Gln Gly Leu
            20                  25

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 111
```

```
His His His His His His
1               5

<210> SEQ ID NO 112
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Pro Lys Ser Arg Phe Ala Met Leu Asp Asp Val Lys Ile Leu Ala
1               5                   10                  15

Asn Gly Leu Leu Gln Leu Gly His Gly Leu
            20                  25
```